United States Patent
Song et al.

(10) Patent No.: US 12,040,054 B2
(45) Date of Patent: Jul. 16, 2024

(54) GLOBAL ANCESTRY DETERMINATION SYSTEM

(71) Applicant: Ancestry.com DNA, LLC, Lehi, UT (US)

(72) Inventors: Shiya Song, San Mateo, CA (US); Keith D. Noto, San Francisco, CA (US); Yong Wang, Foster City, CA (US)

(73) Assignee: ANCESTRY.COM DNA, LLC, Lehi, UT (US)

( * ) Notice: Subject to any disclaimer, the term of this patent is extended or adjusted under 35 U.S.C. 154(b) by 1100 days.

(21) Appl. No.: 15/931,009

(22) Filed: May 13, 2020

(65) Prior Publication Data

US 2020/0286579 A1 Sep. 10, 2020

Related U.S. Application Data

(63) Continuation of application No. 16/567,957, filed on Sep. 11, 2019, now Pat. No. 10,692,587.

(60) Provisional application No. 62/858,820, filed on Jun. 7, 2019, provisional application No. 62/752,523, filed on Oct. 30, 2018, provisional application No. 62/743,448, filed on Oct. 9, 2018, provisional application No. 62/729,840, filed on Sep. 11, 2018.

(51) Int. Cl.
| | | |
|---|---|---|
| *G16B 5/20* | (2019.01) | |
| *C12Q 1/6827* | (2018.01) | |
| *G06F 17/18* | (2006.01) | |
| *G06N 5/01* | (2023.01) | |
| *G06N 7/01* | (2023.01) | |
| *G16B 5/00* | (2019.01) | |
| *G16B 20/20* | (2019.01) | |
| *G16B 20/40* | (2019.01) | |
| *G16B 30/00* | (2019.01) | |
| *G16B 40/00* | (2019.01) | |
| *G16B 50/10* | (2019.01) | |
| *G16H 10/40* | (2018.01) | |
| *G16H 10/60* | (2018.01) | |
| *G06N 20/00* | (2019.01) | |

(52) U.S. Cl.
CPC ............ *G16B 5/20* (2019.02); *C12Q 1/6827* (2013.01); *G06N 5/01* (2023.01); *G06N 7/01* (2023.01); *G16B 5/00* (2019.02); *G16B 20/20* (2019.02); *G16B 20/40* (2019.02); *G16B 30/00* (2019.02); *G16B 40/00* (2019.02); *G16B 50/10* (2019.02); *G16H 10/40* (2018.01); *G16H 10/60* (2018.01); *G06F 17/18* (2013.01); *G06N 20/00* (2019.01)

(58) Field of Classification Search
CPC ........ G16B 30/00; G16B 40/20; G16B 40/00; G16B 20/00; G16B 20/20; G16B 20/40; G16B 30/10; G16B 45/00; G16B 5/20; G16B 5/00; G16B 50/00; G16B 50/10; G16B 50/30; C12Q 1/6869; C12Q 2537/165; C12Q 2600/156; C12Q 2600/172; C12Q 1/68; G06N 20/00; G06N 7/01; G06N 3/08; G06N 3/09; G06N 3/02; G16H 50/70; G06F 17/18; G06F 16/29; G06F 16/9024; G06T 11/206; G06T 2200/24; G06V 10/82

See application file for complete search history.

(56) References Cited

U.S. PATENT DOCUMENTS

| | | |
|---|---|---|
| 9,213,944 B1 | 12/2015 | Do et al. |
| 9,213,947 B1 | 12/2015 | Do et al. |
| 9,836,576 B1 | 12/2017 | Do et al. |
| 9,910,962 B1 | 3/2018 | Fakhrai-Rad et al. |
| 10,223,498 B2 | 3/2019 | Han et al. |
| 10,558,930 B2 | 2/2020 | Noto et al. |
| 10,692,587 B2 * | 6/2020 | Song ................. G16B 40/30 |
| 2004/0267458 A1 | 12/2004 | Judson et al. |
| 2005/0255508 A1 | 11/2005 | Casey et al. |

(Continued)

FOREIGN PATENT DOCUMENTS

| | | |
|---|---|---|
| CN | 106846029 A | 6/2017 |
| WO | WO 2014/151088 | 9/2014 |

(Continued)

OTHER PUBLICATIONS

Durand et al (2014) reducing pervasive false-positive identical by descent segments detected by large scale pedigree analysis. Mol Biol Evol. vol. 31 No. 8 p. 2212-2222. (Year: 2014).*

(Continued)

*Primary Examiner* — Mary K Zeman
(74) *Attorney, Agent, or Firm* — Fenwick & West LLP

(57) ABSTRACT

An input genotype is divided into a plurality of windows, each including a sequence of SNPs. For each window, a diploid HMM is computed based on genotypes and/or phased haplotypes to determine a probability of a haplotype sequence being associated with a particular label. For example, the diploid HMM for a window is used to determine the emission probability that the window corresponds to a set of labels. An inter-window HMM, with a set of states for each window, is computed. Labels are assigned to the input genotype based on the inter-window HMM. Upper and lower bounds are estimated to produce a range of likely percentage values an input can be assigned to a given label. Confidence values are determined indicating a likelihood that an individual inherits DNA from a certain population. Maps are generated with polygons representing regions where a measure of ethnicity of population falls within specific ranges.

20 Claims, 23 Drawing Sheets

(56) References Cited

U.S. PATENT DOCUMENTS

| | | | |
|---|---|---|---|
| 2008/0228043 | A1 | 9/2008 | Kenedy et al. |
| 2010/0256917 | A1 | 10/2010 | McVean et al. |
| 2013/0085728 | A1 | 4/2013 | Tang et al. |
| 2013/0163860 | A1 | 6/2013 | Suzuki et al. |
| 2013/0297221 | A1 | 11/2013 | Johnson et al. |
| 2014/0045705 | A1 | 2/2014 | Bustamante et al. |
| 2014/0067355 | A1 | 3/2014 | Noto et al. |
| 2014/0194300 | A1 | 7/2014 | Song et al. |
| 2015/0106115 | A1 | 4/2015 | Hu et al. |
| 2016/0350479 | A1 | 12/2016 | Han et al. |
| 2017/0017752 | A1 | 1/2017 | Noto et al. |
| 2017/0262577 | A1 | 9/2017 | Ball et al. |
| 2017/0329904 | A1 | 11/2017 | Naughton et al. |
| 2019/0114219 | A1 | 4/2019 | Do et al. |
| 2020/0005899 | A1 | 1/2020 | Nicula et al. |
| 2020/0160202 | A1* | 5/2020 | Noto ................. G16B 40/20 |
| 2020/0286579 | A1* | 9/2020 | Song ................. G16H 10/60 |
| 2021/0134387 | A1* | 5/2021 | McMaster-Schraiber ................. G06N 3/045 |

FOREIGN PATENT DOCUMENTS

| | | |
|---|---|---|
| WO | WO 2015/051006 | 4/2015 |
| WO | WO 2016/061568 A1 | 4/2016 |
| WO | WO 2018/129413 A1 | 7/2018 |

OTHER PUBLICATIONS

23andMe Inc., "Ancestry Composition: 23andMe's State-of-the-Art Geographic Ancestry Analysis," 2015, ten pages, [Online] Retrieved from the Wayback Machine <URL: https://web.archive.org/web/20150905120544/https://www.23andme.com/ancestry_composition_guide/).

Brooks, R.R. et al., "Behavior Detection Using Confidence Intervals of Hidden Markov Models," IEEE Transactions on Systems, Man, and Cybernetics—Part B: Cybernetics, vol. 39, No. 6, Dec. 2009, pp. 1484-1492.

European Patent Office, Extended European Search Report, European Patent Application No. 19859999.5, dated Jun. 15, 2022, eight pages.

European Patent Office, Extended European Search Report, European Patent Application No. 19849462.7, dated Apr. 5, 2022, eight pages.

Hoggart, C.J. et al., "Design and analysis of admixture mapping studies," The American Journal of Human Genetics 74.5, Apr. 14, 2004, pp. 965-978.

Krogh, A. S., "Hidden Markov models for labeled sequences," Proceedings of the 12th IAPR International Conference on Pattern Recognition: Conference B: Computer Vision & Image Processing, vol. 2, 1994, pp. 140-144.

Liu, E.Y. et al., "MaCH-Admix: Genotype Imputation for Admixed Populations," Genet Epidemiol 37(1), Jan. 2013, pp. 25-37.

Lu, C. et al., "A Normalized Statistical Metric Space for Hidden Markov Models," IEEE Transactions on Cybernetics, vol. 43, No. 3, Jun. 2013, pp. 806-819.

Silva, M.C. et al., "Development of two multiplex mini-sequencing panels of ancestry informative SNPs for studies in Latin Americans: an application to populations of the State of Minas Gerais (Brazil)," Genetics and Molecular Research 9(4), Oct. 19, 2010, pp. 2069-2085.

Joshi, S. et al., "Identifiable Phenotyping using Constrained Non-Negative Matrix Factorization," Proceedings of the 1st Machine Learning for Healthcare Conference, PMLR vol. 56, Aug. 2016, pp. 17-41.

Khodabandelou, G. et al., "Genome Functional Annotation using Deep Convolutional Neural Network," PLoS, May 25, 2018, pp. 1-31.

PCT International Search Report and Written Opinion, PCT Application No. PCT/IB2021/050275, dated Apr. 1, 2021, 14 pages.

Browning, S. R., "Rapid and Accurate Haplotype Phasing and Missing-Data Inference for Whole-Genome Association Studies by Use of Localized Haplotype Clustering," The American Journal of Human Genetics, Nov. 2007, vol. 81, 14 pages.

Browning, B. L., "A Fast, Powerful method for Detecting Identity by Descent," The American Journal of Human Genetics, Feb. 11, 2011, vol. 88, pp. 173-182.

Browning, B.I. et al., "Detecting Identity by Descent and Estimating Genotype Error Rates in Sequence Data," The American Journal of Human Genetics, Nov. 7, 2013, pp. 840-851.

Browning, B.L., "A Unified Approach to Genotype Imputation and Haplotype-Phase Inference for Large Data Sets of Trios and Unrelated Individuals," The American Journal of Human Genetics, Feb. 13, 2009, vol. 84, pp. 210-223.

Browning, B.L., "Genotype Imputation with Millions of Reference Samples," The American Journal of Human Genetics, Jan. 7, 2016, vol. 98, pp. 116-126.

Browning, S.R. et al., "Haplotype phasing: Existing methods and new developments," Nat Rev Genet, Apr. 1, 2012, vol. 12, No. 10, pp. 703-714.

Browning, S.R., "Multilocus Association Mapping Using Variable-Length Markov Chains, " The American Journal of Human Genetics, Jun. 2006, vol. 78, pp. 903-913.

De Roos, A.P.W., "Genomic selection in dairy cattle," PHD Thesis at Wageningen University, 2011, 185 pages.

Ghahramani, Z. "An Introduction to Hidden Markov Models and Bayesian Networks," International Journal of Pattern recognition and Artificial Intelligence, 2001, vol. 15, No. 1, pp. 9-42.

Halperin, E. et al., "Haplotype reconstruction from genotype data using Imperfect Phylogeny," Bioinformatics, 2004, vol. 20, No. 12, pp. 1842-1849.

Han, E. et al., "Clustering of 770,000 genomes reveals post-colonial population structure of North America," Nature communications, 2017, vol. 8, pp. 1-12.

Howie, B. N. et al., "A Flexible and Accurate Genotype Imputation Method for the Next Generation of Genome-Wide Association Studies," PLoS Genetics, Jun. 2009, vol. 5, No. 6, pp. 1-15.

Li, N. et al., "Modeling Linkage disequilibrium and Identifying Recombination Hotspots Using Single-Nucleotide Polymorphism Data," the Genetics Society of America, 2003, vol. 165, pp. 2213-2233.

Li, Y. et al., "MaCH: Using Sequence and Genotype Data to Estimate haplotypes and Unobserved Genotypes," Genetic Epidemiology, 2010, vol. 34, pp. 816-834.

Ma, P. et al., "Comparison of different methods for imputing genome-wide marker genotypes in Swedish and Finnish Red Cattle," J. Dairy Sci., 2013, vol. 96, pp. 4666-4677.

Maples, B.K. et al., "RFMix: A discriminative modeling approach for rapid and robust local-ancestry inference," The American Journal of Human Genetics, 2013, Vo. 93, No. 2, pp. 278-288.

McPeek, M. S. et al., "Assessment of Linkage Disequilibrium by the Decay of Haplotype Sharing with Application to Fine-Scale Genetic Mapping," American Journal of Human Genetics, 1999, vol. 65, pp. 858-875.

Montesinos-Lopez, O. A. et al., 'Prediction of multiple-trait and multiple-environment genomic data using recommender systems', G3: Genes, Genomes, Genetics, Jan. 2018, vol. 8, pp. 131-147.

Moreno-Estrada, A. et al., Reconstructing the Population Genetic History of the Caribbean, PLoS Genetics, Nov. 2013, vol. 9, No. 11, pp. 1-19.

Noto, K. et al., "322 Polly: A novel approach for estimating local and global admixture proportion based on rich haplotype models," ASHG 2015 Abstracts, The American Society of Human Genetics 65th Annual Meeting, Oct. 2015, 184 pages.

PCT International Search Report and Written Opinion, PCT Application No. PCT/IB2019/057667, dated Jan. 10, 2020, 10 pages.

PCT International Search Report and Written Opinion, PCT Application No. PCT/IB2019/056939, dated Jan. 3, 2020, 11 pages.

Rabiner, L.R., "A Tutorial on Hidden Markov Models and Selected Applications in Speech Recognition," Proceedings of the IEEE, Feb. 1989, vol. 77, No. 2, pp. 257-286.

(56) References Cited

OTHER PUBLICATIONS

Ron, D., "On the Learnability and Usage of Acyclic Probabilistic Finite Automata," Journal of Computer and System Sciences, 1998, vol. 56, pp. 133-152.

Scheet, P. et al., "A Fast and Flexible Statistical model for Large-Scale Population Genotype Data: Applications to Inferring Missing Genotypes and Hplotypic Phase," The American Journal of Human Genetics, Apr. 2006, vol. 78, pp. 629-644.

Stephens, M. et al., "Accounting for Decay of Linkage Disequilibrium in Haplotype Inference and Missnig-Data Imputation," American Journal of Human Genetics, 2005, vol. 76, pp. 449-462.

Sundquist, A. et al., "Effect of genetic divergence in identifying ancestral origin using HAPAA," Genome Res., Mar. 18, 2008, vol. 18, pp. 676-682.

Tang, H. et al., "Reconstructing Genetic Ancestry Blocks in Admixed Individuals," The American journal of Human Genetics, Jul. 2006, vol. 79, pp. 1-12.

The 1000 Genomes Project Consortium, "A global reference for human genetic variation," Macmillan Publishers Limited, Nature, Oct. 1, 2015, vol. 526, No. 7571, pp. 68-74.

Williams, A.L. et al., "Phasing of Many Thousands of Genotyped Samples," The American Journal of Human Genetics, Aug. 10, 2012, vol. 91, pp. 238-251.

Yoon, B.J., "Hidden Markov Models and their Applications in Biological Sequence Analysis," Current Genomics, 2009, vol. 10, pp. 402-415.

Zeng, X. et al., 'Probability-based collaborative filtering model for predicting gene-disease associations', BMC Medical Genomics, 2017, vol. 10, No. 76, pp. 45-53.

Zhao, H. et al., "Haplotype analusis in population genetics and association studies," Pharmacogenomics, 2003, vol. 4, No. 2, pp. 171-178.

Alexander, D.H., et al., "Fast model-based estimation of ancestry in unrelated individuals," Genome research, 2009, vol. 19, No. 9, pp. 1655-1664.

Ball, C. et al., "Ancestry DNA Matching White Paper," Ancestry.com., 2016, [Online] [Retrieved Sep. 18, 2019], Retrieved from the internet, URL: <<https://www.ancestry.com/corporate/sites/default/files/AncestryDNA-Matching-White-Paper.pdf>>, Last updated Mar. 31, 2016, pp. 1-46.

Baran, Y. et al., "Fast and accurate inference of local ancestry in Latino populations." Bioinformatics, 2012, vol. 28, No. 10, pp. 1359-1367.

Bastian, M. et al., "Gephi: an open source software for exploring and manipulating networks," Third international AAAI conference on weblogs and social media, 2009, 361-362.

Bercovici, S. et al., "Ancestry inference in complex admixtures via variable-length Markov chain linkage models," Annual International Conference on Research in Computational Molecular Biology, Springer, Berlin, Heidelberg, 2012, vol. 7262, pp. 12-28.

Brisbin, A. et al. "PCAdmix: principal components-based assignment of ancestry along each chromosome in individuals with admixed ancestry from two or more populations," Human biology, 2012, vol. 84, No. 4, 343-364.

Browning, B.L. et al., "Efficient multilocus association testing for whole genome association studies using localized haplotype clustering," Genetic Epidemiology, Jan. 1, 2007, vol. 31, No. 5, pp. 365-375.

Cann, H.M. et al., "A human genome diversity cell line panel," Science, 2002, vol. 296, No. 5566, pp. 261-262.

Cavalli-Sforza, L.L. "The human genome diversity project: past, present and future," Nature Reviews Genetics, 2005, vol. 6, No. 4.

Eronen, L. et al., "A Markov chain approach to reconstruction of long haplotypes," Pacific Symposium on Biocomputing, Jan. 1, 2004, 12 pages.

European Patent Office, Extended European Search Report, European Patent Application No. 16823964, dated Apr. 3, 2019, 14 pages.

Gravel, S., "Population genetics models of local ancestry," Genetics, 2012, vol. 191, No. 2, pp. 607-619.

Guan, Y., "Detecting structure of haplotypes and local ancestry," Genetics, 2014, vol. 196, No. 3, pp. 625-642.

Harvard.edu, "Plink . . . Whole genome assocaition analysis toolset," [Online] [Retrieved Sep. 19, 2019], Last edited Jan. 25, 2017, Retrieved from the internet ,URL:<<http://zzz.bwh.harvard.edu/plink/>>, 4 pages.

Hellenthal, G. et al., "A genetic atlas of human admixture history," Science, 2014, vol. 343, No. 6172, pp. 747-751.

Horton, R. et al., "Variation Analysis and Gene Annotation of Eight MHC Haplotypes: the MHC Halotype Project," Immunogenetics, 2008, Vo. 60, pp. 1-18.

International HapMap Consortium, "A haplotype map of the human genome," Nature, 2005, vol. 437, No. 27, pp. 1299-1320.

International HapMap Consortium, "A second generation human haplotype map of over 3.1 million SNPs," Nature, 2007, vol. 449, No. 7164, pp. 1-30.

Itan, Y. et al., "The origins of lactase persistence in Europe," PLoS computational biology, 2009, vol. 5, No. 8, pp. 1-13.

Jackson, J.E., "A user's guide to principal components," vol. 587. John Wiley & Sons, 2005.

Ke, X. et al. "Singleton SNPs in the human genome and implications for genome-wide association studies," European Journal of Human Genetics, 2008, vol. 16, No. 4, 10 pages.

Lawson, D.J. et al., "Inference of population structure using dense haplotype data," PLoS genetics, 2012, vol. 8, No. 1, pp. 1-16.

Li, Y. et al., "Genotype Imputation," Ann. Rev. Genomics Hum. Genet., 2009, vol. 10, pp. 387-406.

Loh, P.R. et al., "Inferring admixture histories of human populations using linkage disequilibrium," Genetics, 2013, vol. 193, No. 4, pp. 1233-1254.

Ma, Y. et al. "Accurate inference of local phased ancestry of modern admixed populations," Scientific reports, 2014, vol. 4, No. 5800 , pp. 1-5.

Noto, K. et al., "A novel approach for estimating local and global admicture proportion based on rich haplotype models," Invited Talk at the American Society of Human Genetics (ASHG) annual meeting, Baltimore, MD, Oct. 2015, 6 pages.

Noto, K., et al. "Underdog: a fully-supervised phasing algorithm that learns from hundreds of thousands of samples and phases in minutes. Invited Talk," 64th Annual Meeting of the American Society of Human Genetics, 2014.

Paşaniuc, B. et al., "Imputation-based local ancestry inference in admixed populations," International Symposium on Bioinformatics Research and Applications, Springer, Berlin, Heidelberg, 2009, pp. 221-233.

Paşaniuc, B. et al. "Inference of locus-specific ancestry in closely related populations," Bioinformatics, 2009, vol. 25, No. 12, p. i213-i221.

Patterson, N. et al., "Population structure and eigenanalysis," PLoS genetics, 2006, vol. 2, No. 12, pp. 2074-2093.

PCT International Notification of Transmittal of the International Search Report and the Written Opinion, PCT Patent Application, PCT/IB2019/057667, dated Sep. 11, 2019, 10 pages.

PCT International Search Report and Written Opinion, PCT Application No. PCT/IB2016/054180, dated Oct. 18, 2016, 11 pages.

Price, A.L. et al., "Sensitive detection of chromosomal segments of distinct ancestry in admixed populations," PLoS genetics, Jun. 2009, vol. 5, No. 6, pp. 1-18.

Pritchard, J.K. et al., "Inference of population structure using multilocus genotype data," Genetics Society of America, 2000, vol. 155, No. 2, pp. 945-959.

Purcell, S. et al., "PLINK: a tool set for whole-genome association and population-based linkage analyses," The American journal of human genetics, 2007, vol. 81, No. 3, pp. 559-575.

Ranciaro, A. et al., "Genetic origins of lactase persistence and the spread of pastoralism in Africa," The American Journal of Human Genetics, 2014, vol. 94, No. 4, pp. 496-510.

Roach, J.C. et al., "Analysis of genetic inheritance in a family quartet by whole-genome sequencing," Science, 2010, vol. 328, No. 5978, pp. 636-639.

Sankararaman, S. et al., "Estimating local ancestry in admixed populations," The American Journal of Human Genetics, 2008, vol. 82, No. 2, pp. 290-303.

(56) References Cited

OTHER PUBLICATIONS

Sturm, R.A. et al., "A single SNP in an evolutionary conserved region within intron 86 of the HERC2 gene determines human blue-brown eye color," The American Journal of Human Genetics, 2008, vol. 82, No. 2, pp. 424-431.
Wikipedia, "Inverse distance weighting," [Online] [Retrieved Sep. 18. 2019], Last edited Mar. 4, 2019, Retrieved from the internet, URL :<<https://en.wikipedia.org/wiki/Inverse_distance_weighting>>.
United States Office Action, U.S. Appl. No. 16/567,957, dated Dec. 10, 2019, 11 pages.

\* cited by examiner

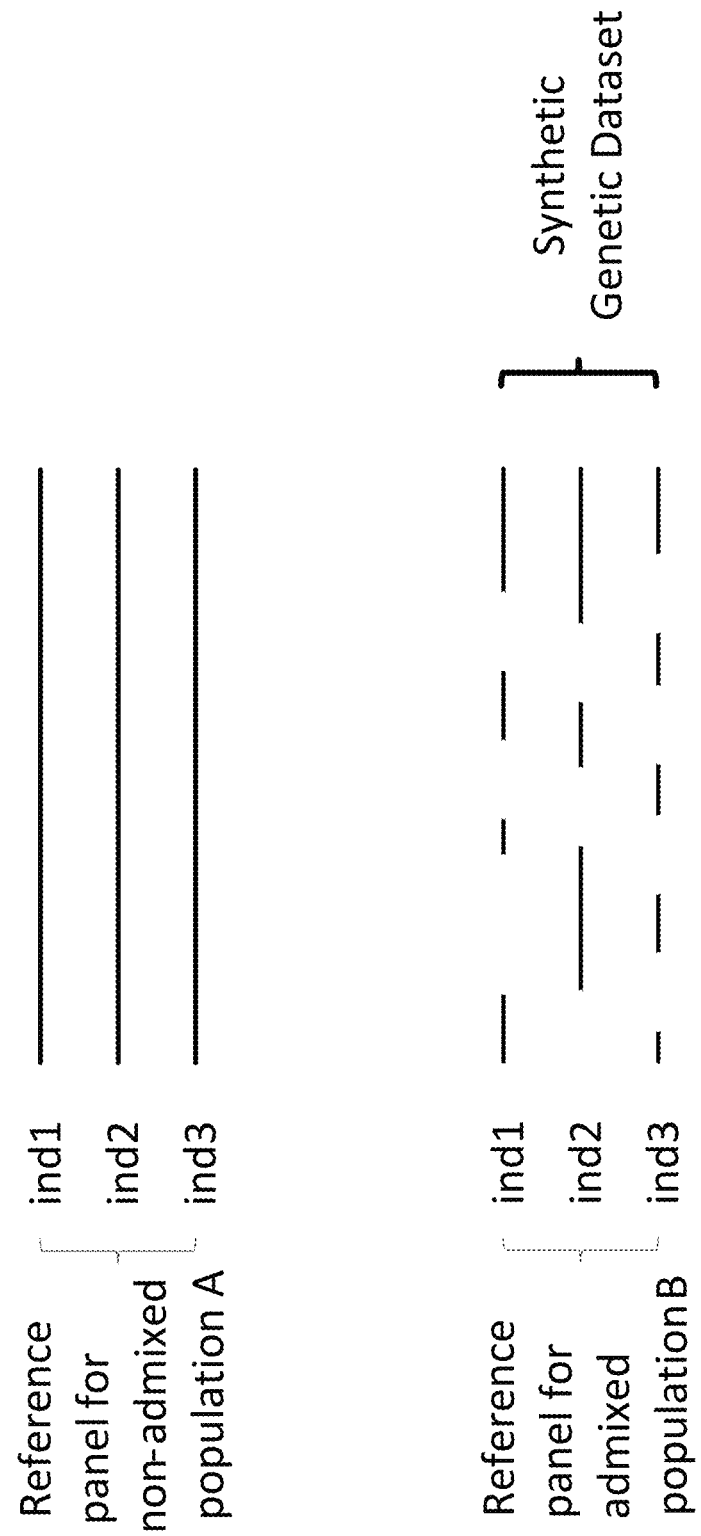

GLOBAL ANCESTRY DETERMINATION SYSTEM

CROSS-REFERENCE TO RELATED APPLICATIONS

The present application is a continuation application of prior, co-pending U.S. application Ser. No. 16/567,957, filed on Sep. 11, 2019, which claims the benefit of U.S. Provisional Patent Applications No. 62/729,840 filed on Sep. 11, 2018, 62/743,448 filed on Oct. 9, 2018, 62/752,523 filed on Oct. 30, 2018, and 62/858,820 filed on Jun. 7, 2019, which are all hereby incorporated by reference in their entirety. PCT Application No. PCT/IB2019/057667, filed on Sep. 11, 2019, is also incorporated by reference in its entirety.

FIELD

The disclosed embodiments relate to assigning labels to an input sample genotype. In particular, the disclosed embodiments relate to using hidden Markov models that efficiently and accurately determine labels for the input sample genotype.

BACKGROUND

Although humans are, genetically speaking, almost entirely identical, small differences in human DNA are responsible for much of the variation between individuals. For example, a sequence variation at one position in DNA between individuals is known as a single-nucleotide polymorphism (SNP). Stretches of DNA inherited together from a single parent are referred to as haplotypes (e.g., one haplotype inherited from the mother and another haplotype inherited from the father).

A subset of the SNPs in an individual's genome may be detected with SNP genotyping. Through SNP genotyping, the pair of alleles for a SNP at a given location in each haplotype may be identified. For example, a genotype at a SNP locus may be identified as heterozygous (i.e., one allele of each type), homozygous (i.e., both alleles of a same type), or unknown. SNP genotyping identifies the pair of alleles for a given genotype, but does not identify which allele corresponds to which haplotype, i.e., SNP genotyping does not identify the homomorphic chromosome (of the homomorphic pair) to which each allele corresponds. Thus, successful SNP genotyping produces an unordered pair of alleles, where each allele corresponds to one of two haplotypes.

In general, most of the SNPs of a haplotype that correspond to a particular chromosome are sourced from a single chromosome from a parent. However, some of the SNPs from the haplotype may correspond to the parent's other homomorphic chromosome due to chromosomal crossover. Because the genetic information in a particular chromosome of an individual mostly corresponds to a single chromosome of a parent, sequences of SNPs tend to stay relatively intact across generations.

SUMMARY

The computer implemented system and method described herein assign to an input sample genotype dataset one or more labels from a set of labels. Labels may be, for example, ethnicity labels indicating an ancestral origin group. Labels are assigned to the input sample genotype datasets by computing two types of hidden Markov models (HMMs): within-window diploid HMMs and an inter-window HMM.

Each diploid HMM is based on the SNPs in a window of one of the chromosomes of the input sample genotype dataset. The output from diploid HMMs may be used to build an inter-window HMM that includes a set of states corresponding to each window across the chromosomes of the input sample genotype dataset. Each state may be graphically by a node in the HMM.

The diploid HMM is computed by accessing the input sample genotype dataset from a memory and dividing it into a number of windows, where each window includes a sequence of SNPs from the input sample genotype. A diploid HMM is computed for each window based on the sequence of SNPs in that window. Each diploid state in a diploid HMM for a window may correspond to a pair of haploid states for the window, where each haploid state corresponds to a different haplotype cluster from a haploid Markov model (MM) for the window. The haploid MM is a probabilistic model of haplotypes for each window. For each diploid state in a diploid HMM of a window, a diploid state probability indicating the likelihood that the input sample genotype corresponds to the diploid state is calculated.

For each window, a label pair probability distribution may be calculated based on the annotations for the window and the diploid state probabilities of the input sample genome for the diploid HMM of the window. In some embodiments, a label may be used to denote an ethnic origin. The label pair probability distribution for a window may map each pair of ordered labels (one label for each of two constituent haplotypes for a window) to the probability that the SNPs in the window correspond to the pair of labels. A set of annotations may be accessed, each annotation corresponding to a haploid state from a window and a label from the set of labels, where the labels include the origin groups under consideration. An annotation for a haploid state indicates the probability that a haplotype of the label (e.g., a haplotype for an individual in the origin group correspond to the label) corresponds to that haploid state. Each annotation for a label may be calculated from a set of reference samples that correspond to the labels.

An inter-window HMM may be computed or built based on the label pair probability distributions. The inter-window HMM includes a plurality of node groups. Each node group represents a window that corresponds to a segment of genetic data. In each node group, there are a plurality of nodes. Each node in a particular node group represents one of various possible states of the window. The plurality of nodes represent different possible states of the window. Each state includes a first parent label, a second parent label, and a switch label representing a switching of order of the first parent label and the second parent label to account for potential switch errors in the phased haplotypes. Each node is associated with an emission probability that represents a likelihood of a particular pair of haplotypes corresponding to the window given the first parent label, the second parent label, and the switch label for each state. The inter-window HMM also includes a plurality of edges. Each edge connects a first node of a first node group to a second node of a second node group. Each edge is associated with a transition probability that represents a likelihood of transition from the first node to the second node.

The inter-window HMM may be computed, built, trained, and updated. For example, transition probabilities of the inter-window HMM may be learned based on expectation-maximization. Using a pair of phased haplotype datasets that are derived from phasing of the input genotype dataset of the individual, a Viterbi path of the inter-window HMM can be determined using a Viterbi algorithm. In other implementations, other types of paths and algorithms may be used instead of Viterbi. The nodes traversed by the Viterbi path each is associated with a first parent label and a second parent label. The composition of the plurality of labels of the nodes can be determined. For example, the distribution of each label in terms of percentage may be determined. The results can be presented as a form of information of the ethnical origins of the individual.

In an embodiment, a method may include identifying a plurality of admixed individuals. Each identified admixed individual may have at least one ancestor from a target geographical region. The method may also include retrieving genetic datasets of the plurality of identified admixed individuals. The method may further include identifying, from the retrieved genetic datasets, a plurality of genetic segments that are inherited from a target ethnic origin. At least a first genetic segment may be identified from a first admixed individual of the plurality of identified admixed individuals and a second genetic segment may be identified from a second admixed individual of the plurality of identified admixed individuals. The first and second genetic segments may be different segments. The method may further include creating a synthetic genetic dataset from a combination of the plurality of identified genetic segments that are inherited from the target ethnic origin. The synthetic genetic dataset may include at least the first and second genetic segments. The synthetic genetic dataset may be a representative of the target ethnic origin in the target geographical region.

According to an embodiment, data representing a directed acyclic graph comprising a plurality of node groups is generated based on a genotype dataset of a sample corresponding to an individual. A node group represents a window that corresponds to one of the genetic segments of the identified individual. Each node group comprises a plurality of nodes, each node having a pair of labels. Each label represents an ethnic origin. A reference path traversing the directed acyclic graph and a plurality of sampled paths traversing the directed acyclic graph are determined. A confidence interval around an estimated proportion of an ethnicity of the genotype dataset of the sample is determined as follows. A mean and a standard deviation of the estimated proportion of the ethnicity is determined from the plurality of sampled paths. A score is initialized based on the mean, the standard deviation, the reference path, and one or more parameters based on the genotype datasets of the reference panel. The score is optimized by determining values of the one or more parameters. The confidence interval is determined using the mean, the standard deviation, and the values of the one or more parameters that optimize the score. A confidence that a probability of the estimated proportion of the ethnicity being larger than zero is classified into one of a plurality of confidence levels as follows. A vector of quantiles of the estimated portion of the ethnicity from the plurality of sampled paths is determined. The probability that the proportion of the ethnicity is larger than zero is predicted using the vector of quantiles and the reference path. The confidence interval and the classified confidence level along with the ethnicity proportion are sent for display.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

These and other features, aspects, and advantages of the present invention will become better understood with regard to the following description, and accompanying drawings, where:

FIG. 1B illustrates differences in reference panels for non-admixed population and admixed population.

Figure 1A:
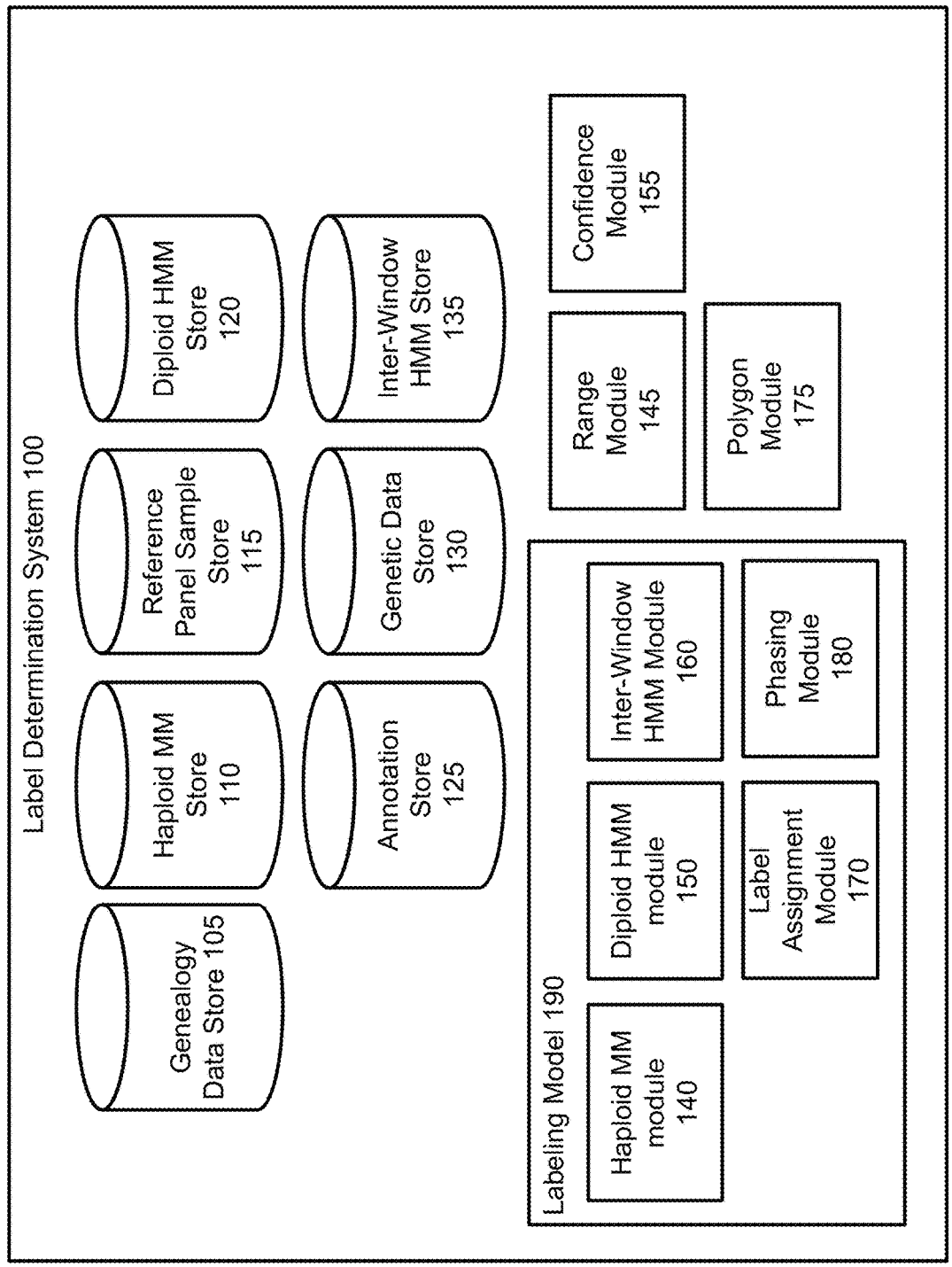
FIG. 1A is a block diagram of a label determination system for training and utilizing a model for assigning labels to a genotype, according to one embodiment.

Note that for purposes of clarity, only one of each item corresponding to a reference numeral is included in most figures, but when implemented multiple instances of any or all of the depicted modules may be employed, as will be appreciated by those of skill in the art.

DETAILED DESCRIPTION

Genetic Data Overview

Individuals may provide deoxyribonucleic acid (DNA) samples (e.g., saliva, skin cells, blood, or other biological matter) for analysis of their genetic data. In one embodiment, an individual uses a sample collection kit to provide a sample from which genetic data can be reliably extracted according to conventional methods. A DNA extraction service can receive the sample and genotype the genetic data, for example by extracting the DNA from the sample and identifying values of SNPs present within the DNA. The result may be referred to as a genotype dataset of the individual. In this disclosure, the result may be an input genotype dataset for further processing based on various processes described in further details below. The genotype dataset is often a diploid genotype. A DNA quality control and matching preparation service may assess data quality of the diploid genotype by checking various attributes such as genotyping call rate, genotyping heterozygosity rate, and agreement between genetic and self-reported gender. The genotype dataset (sometimes also referred to as genotype, or input sample genotype dataset X) is sent (e.g., transmitted through a network) to a label determination system 100. The label determination may receive the genotype from the DNA extraction service or from the DNA quality control and matching preparation service and may store the genotype (e.g., in a database).

A genotype dataset of an individual may include a plurality of SNPs (e.g., say L SNPs). The genotype dataset may be analyzed with focuses on a set of targeted sites of SNPs (e.g., known variable locations of DNA in human genome). Since most SNPs manifest as one of two possible allelic variations within a population (e.g., an SNP may be adenine (A) in some individuals, but cytosine (C) in others), an allele for a particular SNP of a genotype may be referenced by either 0 or 1 (e.g., 0 for A and 1 for C) without loss of generality. Furthermore, although described herein are as using biallelic SNPs (i.e., SNPs that can take on two possible alleles), the methods and systems described herein may be generalized to include multiallelic SNPs (e.g., triallelic SNPs). Additionally, instead of using individual alleles as the basic unit of a genotype dataset, the methods and systems herein may use "mini haplotypes" consisting of multiple alleles as the basic units of data.

A pair of alleles for an SNP in a genotype dataset of an individual may be received without information indicating the homomorphic chromosome to which each allele corresponds. Thus, genotyping data may include in a sequence of L SNPs, each of which contains an unordered pair of values: (0,0) (i.e., homozygous 0), (0,1) (i.e., heterozygous), or (1,1) (i.e., homozygous 1). The first binary value in a pair may be associated with a first parent value and the second binary value may be associated with a second parent value, or vice versa. In some instances, genotyping a particular SNP fails, in which case the alleles for that SNP may be missing. Herein, a genotype dataset may be represented as $G=(G_1, G_2, \ldots, G_L)$, where each $G_i$ (for $i \in \{1, \ldots, L\}$) is an SNP that has a value of either (0,0), (0,1), (1,1), or missing data.

A genotype dataset G may be divided in W windows, where each window w (for $w \in \{1, \ldots, W\}$) is a sequence of SNPs (i.e., a sub-sequence of G). Each window may include a set of sites of SNPs. The sites may correspond to consecutive DNA sequence locations in human chromosome (i.e., every consecutive location of a DNA sequence is a targeted site), but may also be selected sites in which neighboring sites that do not necessarily correspond to neighboring locations in the DNA sequence (e.g., a first SNP site may be at a position A in a DNA sequence while a second SNP site may be at B in the DNA sequence that is hundreds of base pair apart from the position A). In one specific example, each window w includes about 2,000 SNP sites so that the portion of the sequence G corresponding to a window has about 2,000 binary values. The windows may overlap (i.e., share one or more sites of SNPs). For example, a first window may include the first 2,000 sites of SNPs in a chromosome while a second window may include 1,500th to 3,000th sites of SNPs in the chromosome. In one embodiment, a limitation may be imposed such that no window w includes SNPs from more than one chromosome (i.e., from more than one pair of homomorphic chromosomes). For this disclosure, a start point of each window w may be denoted as an SNP index $S_w$ and the length of the window may be denoted as $D_w$. Thus, the sequence of SNPs of the genotype G in window w is $(G_{S_w}, \ldots, G_{(S_w+D_w-1)})$. Using a phasing algorithm, the genotype G can be phased into a pair of phased haplotype datasets H1 and H2 and the entire sequence can be represented as (H11, H12), (H21, H22), (H31, H32), etc., where Hi1 and Hi2 represent i-th SNP.

In some embodiments, genetic composition (e.g., ethnicity composition) of an individual may be determined based on assigning the windows of an input genotype dataset with different labels, such as ethnicity labels. Labels could be any classification labels such as genetic classification labels. In one embodiment, a label corresponds to ancestry from a historical population (e.g., ethnic group). For example, each ethnic group and corresponding label may correspond to a geographic area which the given population historically inhabited. Example areas may be North Africa, Scandinavia, South Asia, etc. For example, a computing system may assign a pair of labels (one being a first parent label such as a patrilineal label and another corresponding to a second parent label such as a matrilineal label) to each window. The labels may be selected from a set of K labels. For example, in the case where the labels are related to ethnic origin, the set of K labels may be African, Asian, European, etc. or be German, Korean, Mexican, etc., depending on the granularity of the classification. A label is an identification of some sequences of haplotypes that are genetically similar Based on the assigned labels, information of the ethnic origin of the individual may be determined. For example, if 80% of the windows are assigned with a European label, the computing system may provide a statement that the individual is of European origin as an example of information of ethnic origin. The information of ethnic origin may also include statistics of the labels. For example, the computing system may provide a detailed breakdown of the ancestry origins (e.g., 75% European, 20% Asian, and 5% African) of the individual based on the individual's genotype dataset.

The length $D_w$ of each window w may be selected so that each window w likely to corresponds to only a single pair of labels. For example, the length $D_w$ of each window w may be selected so as to have a length of 1-10 centimorgans (cM) or less. The details of labeling of each window w will be discussed in further details below in association with FIG. 4.

Label Assignment Process Overview

In accordance with an embodiment, a process to characterize a genotype dataset of an individual as a composition of different classifications is conducted through a label assignment process that makes use of different Markov models. A specific example of label assignment is the determination of a composition of ethnicity origins of the individual by assigning different first parent and second parent ethnicity labels to the individual. The genotype dataset is divided into a plurality of segments (which may be called windows). Each window corresponds to a DNA locus that includes a set of SNP sites. Based on the pair of first and second parent ethnicity labels associated with each window, the total compositions of labels of the genotype dataset can be counted. For example, if there are 580 European first parent ethnicity labels assigned to a total of 1000 windows of a genotype data, the genotype data is determined to have about 58% European origin on the first parent side (e.g., on the father side).

The precise assignment of labels to a genotype dataset is conducted by determining a statistically most likely path (commonly referred to as a Viterbi path) of a machine learning model that might be referred to as an inter-window Hidden Markov Model (HMM). In some embodiments, the Viterbi path and a selection (e.g., 1000) of other multiple statistically likely paths (but not as likely as the Viterbi path) that traverse the inter-window HMM are sampled and are used to determine the statistical confidence of the Viterbi path and the final label assignments.

An inter-window HMM includes certain components. First, the inter-window HMM includes hidden states and observations. A hidden state in an HMM may be graphically represented by a node.

In an inter-window HMM in accordance with an embodiment, a hidden state may be a possible condition of the window. Put differently, a window may take one of multiple possible hidden states while different windows may take different hidden states. In the inter-window HMM in accordance with an embodiment, a state is defined by three labels. The first two labels are a first parent label and a second parent label and these two labels are ordered. In other words, for a given inter-window HMM, either the first parent label is consistently first or the second parent label is consistently first among the states. Hence, a first pair of labels of "European, Asian" represents one of the possible states in a window while a second pair of labels of "Asian, European" represent another possible state that is different from the first pair of labels. Each window associated with a particular genotype dataset may take a different state (i.e., different DNA segments of an individual are assigned with different states that have different pairs of ethnicity labels).

The third label that defines a hidden state is a switch label, which represents that, for a particular state, the order of the first parent label and second parent label in the HMM is switched compared to the actual labels in the sample. Put differently, a switching occurs when the HMM assumes a window having a pair of labels in a particular order, but the actual genotype sample at that window has the same pair of labels, but in a reversed order. For example, a label such as "first parent-European, second parent-Asian, switched" means the correct label in the genotype sample is "first parent-Asian, second parent-European." A switch label is used because, in order for first parent label and second parent label to be considered separately, the genotype dataset needs to be phased to generate a pair of haplotype datasets. However, existing phasing methods are often not perfect. The switch label is used to account for the probability that the phasing is incorrect for a particular window.

An observation associated with a hidden state is a possible observable trait, condition, or value in a sample dataset. In an inter-window HMM in accordance with an embodiment, an observation may be the genotype sequence or phased haplotype sequence pair associated with a window. A hidden state is "hidden" because the state is not immediately apparent given the sample dataset. For example, the label "Asian, European, Not-Switched" for a particular window is not immediately apparent given only the sample genotype dataset or the phased pair of haplotype datasets at the particular window. Simply put, when a sequence of SNPs of a sample is ATGCTATAGC . . . , whether such sequence is inherited from an Asian ancestor, a European ancestor, or another ancestor is not immediately apparent.

Second, the inter-window HMM includes emission probabilities and transition probabilities. A particular hidden state is related to a particular observation by an emission probability. The relationships between different hidden states and different observations might have different values of emission probabilities. A particular hidden state of one window is related to another hidden state of the next window by a transition probability. Graphically, the hidden states in the HMM are represented by nodes that are arranged in node groups (each node group corresponds to a window and the nodes within a node group represent different possible states). An edge that connects two nodes represents a transition with a transition probability.

An emission probability is a probability of an observation being manifested given a particular hidden state. In the inter-window HMM in accordance with an embodiment, an emission probability may represent a likelihood that a particular pair of phased haplotypes is observed in the sample datasets given a particular pair of labels is assigned to the window. Simply put, an emission probability determines what the likelihood is when the sample has the haplotype sequence pairs, for example, "ATGCTATAGC . . . " and "ATGGTATAGC . . . " given the window is assigned with, for example, the labels "Asian, European, not-switched." The emission probability represents how likely the DNA in a window comes from an ethnic origin.

An emission probability is associated with each hidden state and is determined based on genotype datasets of reference panels. A reference panel is a collection of individuals' genotype datasets who are known members of an ethnical population. For example, a Germanic reference panel includes genotype datasets of known Germans. The determination of an emission probability is specific to a particular hidden state with two ethnicity labels and involves a series of steps that include a creation of a haploid Markov Model (MM) and a creation of a diploid Hidden Markov model (HMM) using the reference panels associated with the labels of the particular hidden state. The details of computing a haploid MM and a diploid HMM for each hidden state are discussed in details in association with FIGS. 2 and 3. A series of computations to determine an emission probability may include determinations of one or more intermediate values such as annotations, annotation products, and label pair probabilities. The process of how those values are generated using the haploid MM and diploid HMM in order to determine the emission probability is discussed in details in association with FIG. 5. At a high level, the determination of an emission probability includes comparing a sample genotype dataset of interest to one or more reference panels to determine the likelihood that the pair of haplotypes presented in each window of the sample genotype dataset comes from the populations of the reference panels.

A transition probability is a probability that a hidden state of a first node group is transitioned to a hidden state of the next node group. In the inter-window HMM in accordance with an embodiment, a transition probability may represent, when a set of labels (e.g., "Asian, European, Not-Switched") is assigned to a window, the likelihood that another set of labels (e.g., same labels "Asian, European, Not-Switched" or different labels "Asian, Asian, Not-Switched") should be assigned to the next window. Humans often inherit a large chunk of DNA from an ancestor. Hence, changes in ethnicity labels are less likely when two windows are next to each other. The ethnicity labels of a window depend on the ethnicity labels of the previous window. The transition probability represents such dependence.

It should be noted that "transition" and "switch" represent different concepts in this disclosure. Transition may refer to a change of one or more of the three labels in a hidden state from one window to the next window. Graphically, in a HMM, a transition is represented by an edge, which is a path going from one node of a node group to another node of the next node group. In contrast, switching is related to a potential incorrect phasing for the haplotypes pair in a particular window. Switching occurs when the HMM assumes that a window is at a state with a pair of labels in a particular order, but the actual genotype sample at that window has the same pair of labels, but in a reversed order. In the HMM, a switch label is one of the label values in a node while a transition is represented by an edge in the HMM.

Transition probabilities associated with different edges are determined based on the training of the inter-window HMM until the HMM converges or after a predetermined number of iterations. The training set of the HMM may be sampled from different reference panels such that the training set includes a mix of different ethnicity. In some cases, when a genotype dataset needs to be analyzed, the genotype dataset can first be used to further train the HMM (e.g., as an additional sample of the training set). The determination of transition probabilities is described in further details in FIG. 6.

After the emission probabilities and transition probabilities are determined, the label assignment of a genotype dataset is determined by running a Viterbi algorithm known in the art using the genotype dataset to determine the statistically most likely path of the inter-window HMM (the Viterbi path). The path selects one node for each window (meaning a pair of ethnicity labels are assigned to each window).

Figure 2:
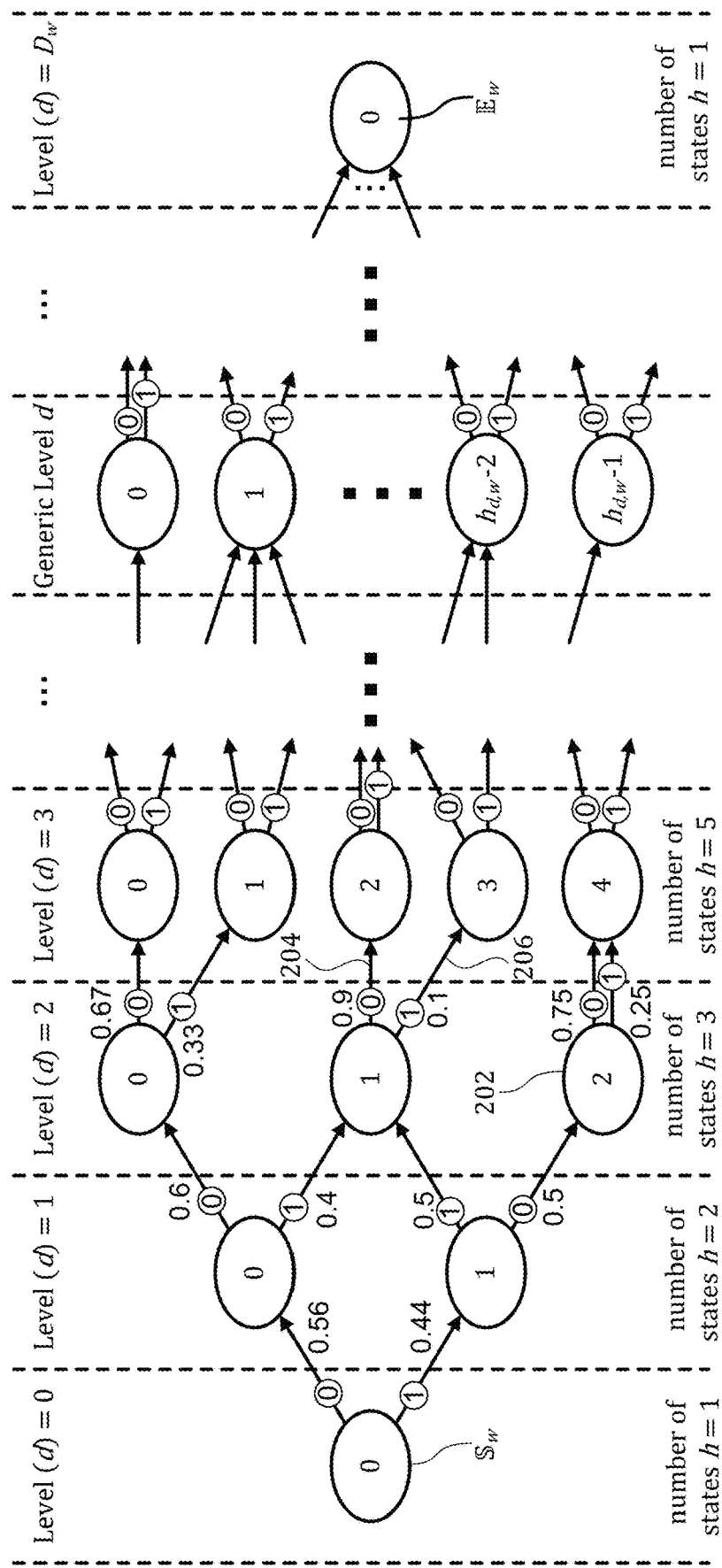
FIG. 2 is an example of a haplotype MM, according to an embodiment.
Figure 3:
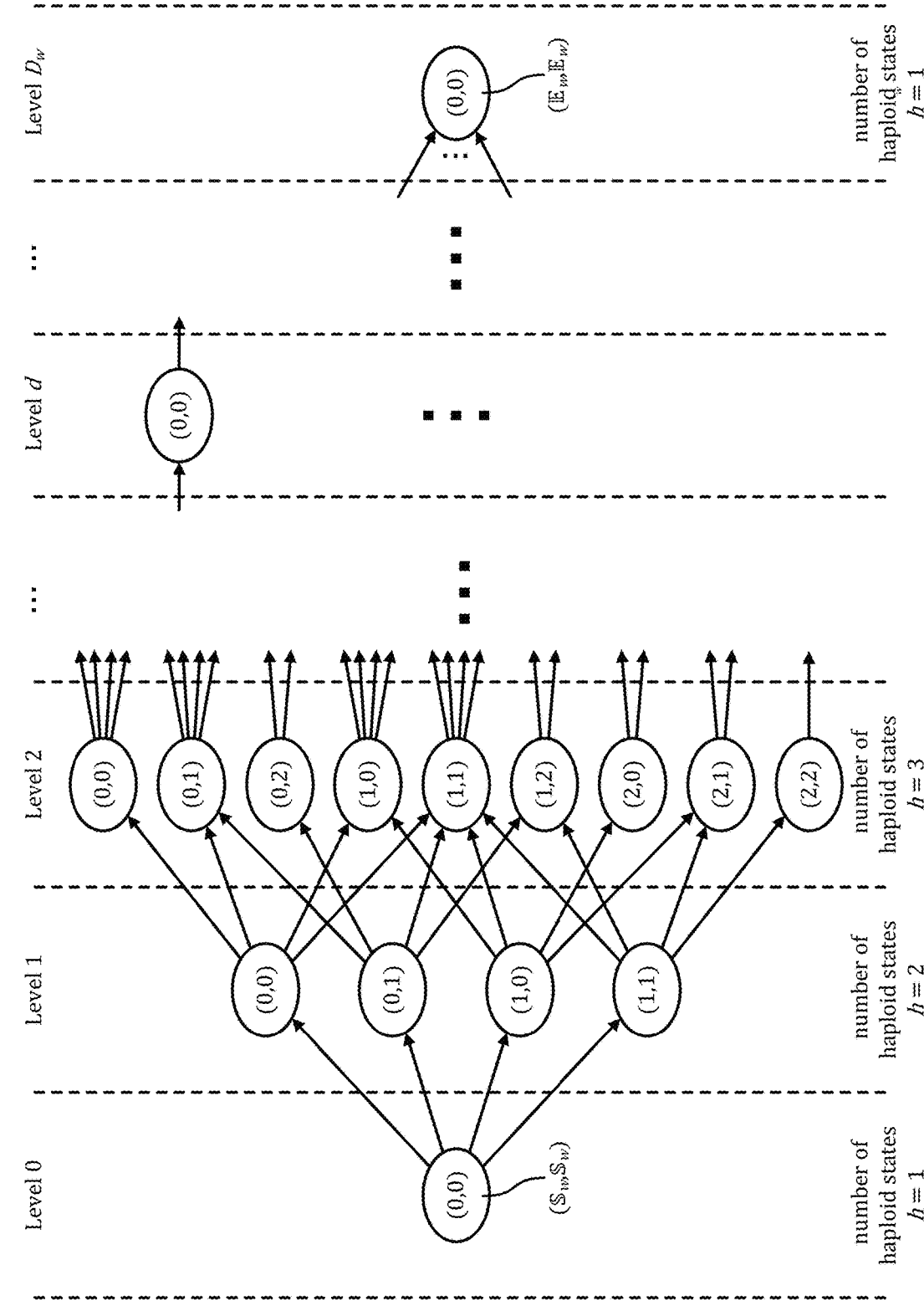
FIG. 3 is an example of a diploid HMM, according to an embodiment.
Figure 4:
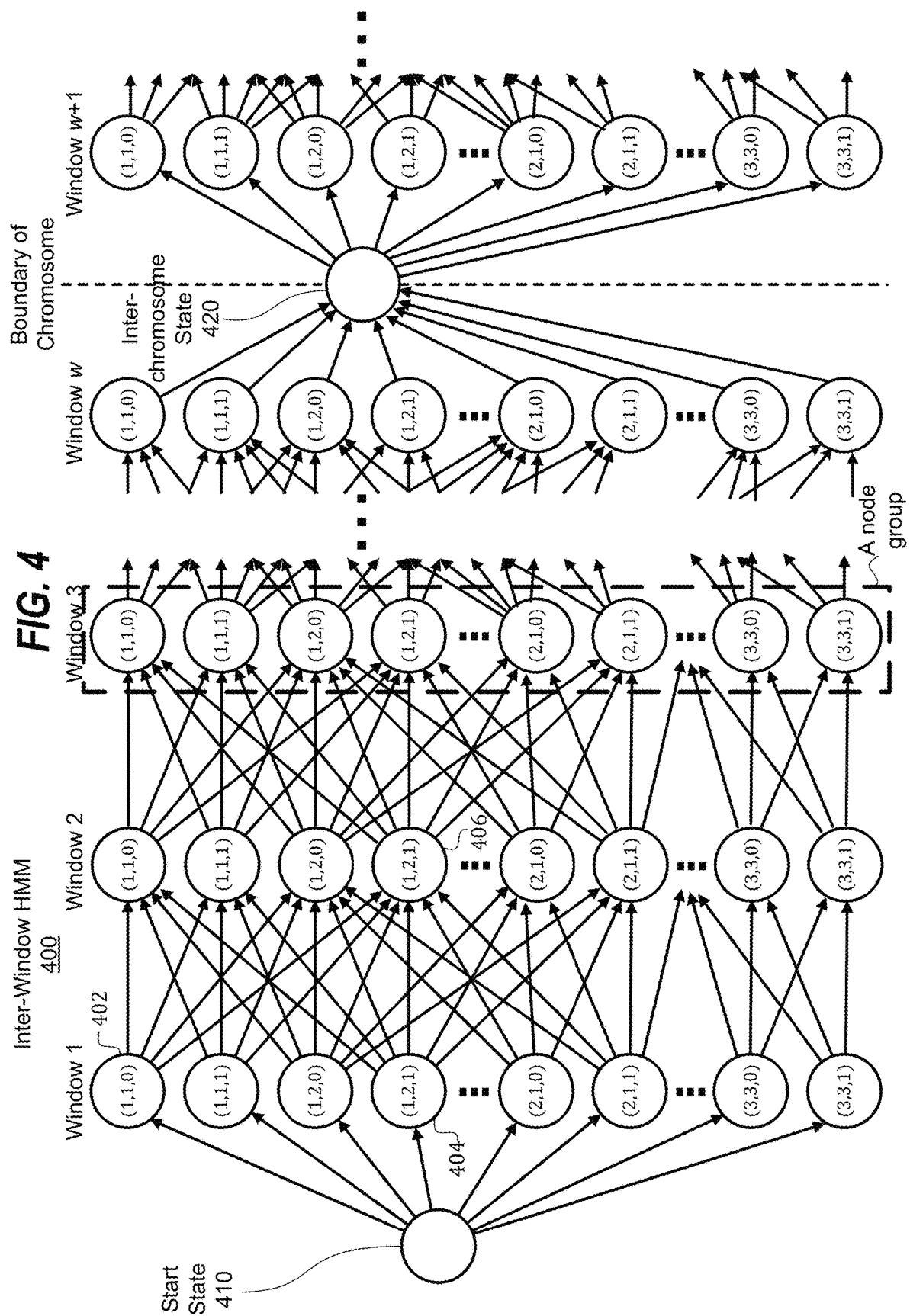
FIG. 4 is an example of an inter-window HMM, according to an embodiment.

Without loss of generality, different Markov models are first described in FIGS. 2-4 and the process of determining emission probabilities, transition probabilities, and label assignments are described afterward in FIGS. 5-8.

System Overview

FIG. 1A is a block diagram of an online system, which can be a label determination system 100 for training and utilizing a model to assign labels to a genotype dataset, according to one embodiment. The label determination system 100 trains and uses models to probabilistically determine the labels to which an input genotype sample corresponds. The label determination system 100 may be a computing system including one or more processors, one or more computer memories, and an interface for communicating through a network. In one example embodiment, the label determination system 100 includes a genealogy data store 105, a haploid MM store 110, a reference panel sample store 115, a diploid HMM store 120, an annotation store 125, a genetic data store 130, and an inter-window HMM store 135, a range module 145, a confidence module 155, and a polygon module 175. The label determination system 100 can build and train a labeling model 190. The labeling model 190 includes various components (which may also be referred to as sub-models or modules) such as a haploid MM module 140, a diploid HMM module 150, an inter-window HMM module 160, a label assignment module 170, and a phasing module 180. In various embodiments, the labeling model 190 may include additional or fewer modules.

An online system, such as the label determination system 100, may maintain user data and genealogical data in the genealogy data store 105. The genealogy data store 105 stores user data for each user of the online system. The amount and type of data stored for each user in the genealogy data store 105 may vary based on the information provided by the corresponding user. Users may provide data via the user interface of a user device. The user interface may be a website or mobile application of the online system. For example, the user may be prompted in an element of a user interface to answer questions related to the user that can be processed to obtain genealogic and survey data. Examples of genealogical data include names (first, last, middle, suffixes), birth locations, date of birth, date of death, marriage information, kinships, family history, and the like. In some instances, family history can take the form of a pedigree of that individual (e.g., the recorded relationships in the family). The pedigree information associated with a user comprises one or more specified nodes. Each specified node in the pedigree represents either the individual or an ancestor of the individual corresponding to a stored DNA sample. Therefore, the pedigree includes the individual and ancestors who have passed down genetic material to the associated individual. The nodes in a pedigree may include personal information of the person (e.g., ancestor) represented by the node. For example, the personal information may include the geographical region in which the person was born. Other personal information may also take the form of various types of genealogical information.

Genealogical data may describe genetic connections among users of the online system. Genealogical data that are obtained from a public record source such as census records may be stored in the genealogy data store 105. Those records may include birth records, death records, marriage records, and census records. Genealogical data in the form of survey data include information about an individual's phenotypes, such as physical traits (e.g., height, hair, skin pigmentation, freckling, bitter taste, earlobe type, iris patterns, male pattern baldness, hair curl), wellness phenotypes (e.g., lactose tolerance, caffeine consumption, malaria resistance, norovirus resistance, muscle performance, alcohol flush), and personal preferences (e.g., likes and dislikes). The genealogy data store 105 may also include information inferred from the genetic data stored in the genetic data store 130 and information received from the individuals. For example, information related to which individuals are genetically related, how they are related, how many generations back they share common ancestors, percent IBD shared, which communities the individual is a part of, variants the individual carries, and the like.

Genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Genetic data store 130 maintains genetic datasets of individuals. Genetic data may contain whole or portions of individual's genome and corresponding metadata. The data stored in the genetic data store 130 may store one or more genetic datasets linked to a user. In various embodiments, the genetic data store 130 stores a pointer to a location associated with the genealogy data store 105 associated with the individual. A genetic dataset may take different forms. In one embodiment, a genetic dataset may take the form of base pair sequence of the DNA sequence of an individual. A genetic dataset may include a whole genome of the individual (e.g., obtained from a whole-genome sequencing) or some parts of genetic loci. In another embodiment, a genetic dataset may take the form of sequences of target SNP sites and allele sites. The genetic dataset may be in the form of a diploid data and may be phased into two sets of haploid data. The diploid data may also be referred to as genotype data while the phased haploid data may be referred to as haplotype data.

In some embodiments, the label determination system 100 may operate in a training stage and a label assignment stage. The training stage may be performed once to train the labeling model 190 that includes sub-models. For example, a haploid MM for each window w stored in the haploid MM store 110 may be trained to calculate the annotations stored in the annotation store 125 for each label k and window w. The training stage is often based on more than a single particular input sample genotype dataset. For example, a collection of training samples may be used. After the training stage, the label determination system 100 may assign labels to an input sample genotype dataset X during the label assignment stage. Assigning labels to the sample genotype dataset X uses the haploid MMs and the annotations initialized during the training phase. In some embodiments, after the training stage for the labeling model 190 has been performed once, labels may be continuously assigned to different input genotype datasets. In other embodiments, after the labeling model 190 is initially trained, the label determination system 100 may continuously improve and update various components of the labeling model 190 by treating previously labeled input genotype datasets that were themselves labeled by the labeling model 190 as additional training samples.

The reference panel sample store 115 may include a collection of reference panel samples. Each reference panel sample may be a genetic dataset that is representative of a particular genetic community. For example, a Japanese reference panel sample may be representative of the genetic data of people of Japanese origin. Each ethnic origin may include more than one reference panel datasets. By comparing a window of genetic data of a target individual to different reference panel samples, the reference panel samples may be used to provide possible ethnic origin labels to the window of genetic data and may also assign a probability that the window of genetic data is inherited from a particular genetic community. This process of assigning labels and determining probabilities may be referred to as annotating.

The phasing module 180 phases diploid genetic dataset into a pair of haploid genetic datasets. An individual's haplotype may refer to a collection of alleles (e.g., a sequence of alleles) that are inherited from a parent. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP site of a pair of chromosomes but may not be able to distinguish which allele belongs to which specific chromosome. The phasing module 180 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing module 180 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as training sample because the correct phasing of the child is almost certain by comparing the child's genotypes to the parent's genetic datasets. The haplotype-cluster model may be generated iteratively along with the phasing process with a large number of unphased genotype datasets.

By way of example, the phasing module 180 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing module 180 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/591,099, entitled "Haplotype Phasing Models," filed on Oct. 19, 2015, describes one possible embodiment of haplotype phasing.

The phasing module 180 may probabilistically separate the input sample genotype X into its constituent haplotypes based on the assigned labels. In one embodiment, a pair of labels for each window w is assigned based on the Viterbi path through the inter-window HMM. Phasing (i.e., separating the input sample genotype X into haplotypes) may be performed based on diploid HMMs 300 for each window w modified by the annotations $A_w$ for the assigned labels. For example, the diploid HMM for the input sample genotype X may be modified so that the probability of the diploid state $(u_1,u_2)$ in the window w is given by $A_w(u_1,p) \times A_w(u_2,q)$. The SNPs in the window w may be phased into the constituent haplotypes by determining the Viterbi path through the modified diploid HMM. In this way, the genome X may be phased so as to maximize the agreement with the label assignment. The haplotypes may also be combined across windows. For example, if the labels (p,q) were assigned to window w and the labels (p,q') were assigned to window w+1, then the sequence of alleles in the phased haplotype corresponding to label p in window w may be combined with the sequence of alleles in the phased haplotype corresponding to label p in window w+1. Similarly, the sequence of alleles in the phased haplotype corresponding to label q in window w may be combined with those of label q' in window w+1.

FIG. 1B illustrates differences between a non-admixed reference panel sample and an admixed reference panel sample. Reference panel samples may include two different types, depending on whether a population is unadmixed or admixed. For a non-admixed population, an entire genetic dataset of an individual may constitute a reference panel sample. For example, for population A, which is assumed to a non-admixed population, genetic datasets of individual 1, individual 2, and individual 3 may be three different reference panel samples that represent the genetic data of the population A. For population B, which is assumed to be an admixed population, a genetic dataset of an individual includes genetic segments that are inherited from different possible ethnic origins. For example, for a Hispanic population, the genetic dataset may include genetic segments of Native American origin, European origin, African origin, etc. For a particular ethnicity, various admixed individuals may have different genetic segments that are inherited from a particular ethnic origin. The online system may combine genetic segments of multiple admixed individuals to form a synthetic genetic dataset. For example, a reference panel sample for an admixed population may include a first genetic segment from a first admixed individual, a second genetic segment from a second admixed individual, etc. The first genetic segment and the second genetic segment are different segments.

The reference panel sample store 115 may include different reference panel samples for various ethnic origins of admixed individuals originated from the same geographical region. A synthetic reference panel formed by combining genetic segments from various individuals may be associated with a geographical region and an ethnic origin. For example, a synthetic genetic dataset representing Native American origin for a Hispanic population from Mexico may be associated with both Mexico (a geographical region) and Native American (an ethnic origin). The reference panel sample store 115 may include another synthetic genetic dataset representing European origin for the same Hispanic population from Mexico. This reference panel may be associated with Mexico and European. Likewise, a synthetic genetic dataset associated with Brazil (a geographical region) and European (ethnic origin) may also be a different reference panel. Put differently, for an admixed population from a particular geographical region, multiple reference panels representing different ethnic origins may be stored.

Haploid Markov Model

The haploid MM store 110 stores a plurality of haploid MMs (Markov Models), each haploid MM corresponding to a window w. The haploid MM module 140 builds the plurality of haploid MMs based on training data (e.g., sequenced haplotypes and/or phased haplotypes). In some embodiments, the haploid MMs may be received from another system (e.g., through a network). Each haploid MM is a probabilistic model of alleles in a respective window w. The haploid MM for a window w is a directed acyclic graph with a finite number of haploid states. Each directed edge between two haploid states in the haploid MM is referred to herein as a "transition" and corresponds to the value of an allele in a haplotype. Therefore, every possible haplotype (e.g., a sequence of alleles) in the window w corresponds to a path (i.e., sequence of haploid states) through the haploid MM corresponding to window w. The states in a haploid MM, the transitions between them, and the probabilities of those transitions are determined by the haploid MM module 140 based on the training data.

FIG. 2 illustrates an example of a haploid MM 200 for a window w, according to one embodiment. FIG. 2 illustrates the haploid MM for window w as a directed graph, where circles represent nodes with each node corresponding to a state, and arrows represent edges with each edge corresponding to a transition between a first state in a d−1th level to a second state in a d-th level. The haploid MM is divided into $D_w+1$ levels (i.e., the haploid MM includes one more level than the number $D_w$ of SNPs in the window w). Each state in the model corresponds to some level $d \in \{0, \ldots, D_w+1\}$. Each level d in the window w includes h states. Each state u in the haploid MM may be referenced by the combination of its level d and an index n (for $n \in \{0, \ldots, h-1\}$), although states may be references with an alternate referencing scheme. In FIG. 2, the index n of each state u is the integer with which the state is labeled. Herein, u(w,d,n) references the nth state at level d in window w. Thus, the start state is $\mathbb{S}_w=u(w,0,0)$, state 202 is u(w,2,2), and the end state is $\mathbb{E}_w=u(w,D_w,0)$.

A haploid MM 200 includes one start state $\mathbb{S}_w$ at level 0 and one end state $\mathbb{E}_w$ at level $D_w$. Besides the end state $\mathbb{E}_w$ at level $D_w$ which is a terminal node, each state at level d can include outgoing transitions to either one or two states at level d+1. The transition between a state at level d−1 to a second state in level d corresponds to the dth allele in window w of a haplotype. In FIG. 2, the allele value of a haplotype corresponding to the transition between two states is illustrated by the number (either 0 or 1) on the arrow between the states. For example, the transition from the start state $\mathbb{S}_w$ to u(w,1,0) (i.e., the state at level 1 with index number n=0) corresponds to an allele of 0 at the first SNP position in window w and the transition from the start state $\mathbb{S}_w$ to u(w,1,1) (i.e., the state at level 1 with index number n=1) may correspond to an allele of 1 at that SNP position. As indicated by FIG. 2, in this example, the transition probability between the start state $\mathbb{S}_w$ and u(w,1,0) is 0.56 and the transition probability between $\mathbb{S}_w$ and u(w,1,1) is 1−0.56=0.44.

In the haploid MM 200, the transition function t(u, a) describes the transition of a haploid state u in a d−1th level to an allele value a in the d-th level, where the allele value a may take a binary value (e.g., $a \in \{0,1\}$). For example, in FIG. 2, t(u(w,2,0),0) describes the transition from u(w,2,0) to u(w,3,0) because u(w,3,0) is the next state that has the allele value 0. Likewise, t(u(w,2,0),1) describes the transition to haploid state u(w,3,1) because u(w,3,1) is the next state that has the allele value 1. When a haploid state u at level d−1 transitions to two distinct states (i.e., when t(u,0) t(u,1)), each of the transitions is mapped to the dth allele in the window w. Herein, p(u, a) refers to the transition probability that state u at level d−1 transition to next state at the d-th SNP that has an allele that takes the value of a. For example, an edge 204, which represents u(w,2,1) transitioning to the next state that has an allele value of 0, corresponds to the transition probability p(u(w,2,1),0)=0.9. Likewise, an edge 206 corresponds to the transitional probability p(u(w,2,1), 1)=0.1. If the state u transitions to only one state v at level d, then the haploid MM may still include a probability distribution for the d-th allele even though the state transition is deterministic. For example, as illustrated in FIG. 2, the transition from state u(w,2,2) to state u(w,3,4) may associate a probability of 0.75 with allele 0 at the third SNP in the window w and a probability of 0.25 for allele 1 at the third SNP in the window w.

Each path through the haploid MM 200 corresponds to one or more possible sequences of alleles (for example, that may occur in the input sample genotype dataset X). The probability of a sequence of alleles is given by the product of the corresponding allele probabilities in the corresponding path. For example, a path that includes the sequence of state ($\mathbb{S}_w$, u(w,1,1), u(w,2,1), u(w,3,3)) corresponds to the sequence of alleles (1,1,1) which has a probability of p($\mathbb{S}_w$,1)×p(u(w,1,1),1)×p(u(w,2,1),1)=0.022. The possible haplotypes (or, equivalently, every possible sequence of alleles) correspond to different paths in the haploid MM. Each path corresponding to a possible haplotype begins at the start state $\mathbb{S}_w$, includes exactly one state for each level d, and ends at the end state $\mathbb{E}_w$.

Diploid Hidden Markov Model

Returning to FIG. 1A, the diploid HMM store 120 stores a plurality of diploid HMMs (hidden Markov Models). Each diploid HMM corresponds to each window w. The diploid HMM module 150 may build these diploid HMMs based on the haploid MMs stored in the haploid MM store 110. Each diploid state in the diploid HMM for window w corresponds to an ordered pair of haploid states (i.e., one haploid state for each of the two haplotypes that constitutes a genome) in the haploid MM 200 for window w. Thus each diploid state $(u_1,u_2)$ in the diploid HMM at level d corresponds to the haploid states $u_1$ and $u_2$, where $u_1$ and $u_2$ are from level d. For example, the start state of the diploid HMM for window w is (u(w,0,0), u(w,0,0))=($\mathbb{S}_w$, $\mathbb{S}_w$). In some embodiments, the haploid states $u_1$ and $u_2$ are phased, meaning $u_1$ is used to represent a first parent haplotype such as a paternal haplotype while $u_2$ is used to represent a second parent haplotype such as a maternal haplotype, or vice versa.

In some embodiments, the diploid HMM store 120 stores a full HMM for each window w. A full diploid HMM for window w includes, for a level d, a diploid state for every ordered pair of haploid states in the haploid MM 200 at level d. Full diploid HMMs may be calculated during a training stage. The diploid HMM store may also include diploid HMMs that correspond to particular genotype datasets. The diploid HMM for a particular genotype dataset G (e.g., an input sample genotype dataset X or a reference panel sample genome for a label k) in window w may include all the possible diploid states that are compatible with the genotype dataset G and the possible transitions for genotype dataset G. Diploid HMMs may be computed for the input sample genotype dataset X by the diploid HMM module 150 during a label assignment stage. Diploid HMMs may be also be computed for the reference panel sample genomes stored in the reference panel sample store 115 during the training stage when calculating the annotations in the annotation store 125. In general, the diploid HMM for window w for a genotype dataset G sometimes includes fewer states than the full diploid HMM for window w, because many diploid states in the full diploid HMM may not be compatible with the genotype G.

In some embodiments, a diploid HMM for a genotype dataset G for a window w is computed based on the full diploid HMM for the window w. In alternate embodiments, the diploid HMM module 150 does not build from full diploid HMMs and no full diploid HMMs are stored in the diploid HMM store 120. Instead, the diploid HMM module may build diploid HMMs for genotype datasets for each window w based on the corresponding haploid MM for window w.

FIG. 3 is an example of a diploid HMM 300 for a window w, according to an embodiment. The diploid HMM illustrated in FIG. 3 is a fully-instantiated diploid HMM. For this reason, the number of diploid states at each level d for window w is equal to the square of the number of states in the corresponding haploid MM 200 at level d (i.e., $h^2$). For a genotype sequence made up of haplotypes that correspond to a diploid state $(u_1,u_2)$ at level d−1, the probability that the d-th alleles in the window w is the ordered pair $(a_1, a_2)$ equals $p(u_1, a_1) \times p(u_2, a_2)$. The number of possible transitions from a diploid state $(u_1,u_2)$ to another state is equal to the number of possible transitions from $u_1$ in the haploid MM to a next state multiplied by the number of possible transitions from $u_2$ to a next state.

FIG. 3 depicts an example diploid HMM 300 that corresponds to the example haploid MM 200 depicted in FIG. 2. In FIG. 3, each node represents a diploid state in the diploid HMM that is labeled with a pair of index numbers (n,m) corresponding to the indices of the corresponding pair of haploid states in the haploid MM 200. For example, the diploid state labeled (1,2) at level 2 in FIG. 3 represents the diploid state (u(w,2,1),u(w,2,2)) where haploid states u(w, 2,1) and u(w,2,2) are from the haploid MM 200 of FIG. 2. In some embodiments, the diploid states are phased so that the order of the two haploid states in a pair of diploid state represents the phase of the haploid states. For example, the diploid state labeled (1,2) represents that the first parent state is in the haploid state 1 while the second parent state is in the haploid state 2 while the diploid state labeled (2,1) represents that the first parent state is in the haploid state 2 while the second parent state is in the haploid state 1, or vice versa if the first state is denoted as the maternal state.

Because every genotype dataset corresponds to two haplotypes, each phased genotype dataset corresponds to a single path through the diploid HMM 300 for window w. However, because the SNPs in unphased genotype datasets do not associate alleles with particular haplotypes, the exact path through the diploid HMM that a genotype dataset traverses may be ambiguous as the genotype dataset will likely include a number of heterozygous SNPs and possibly missing data for SNPs as well. For example, the sequence of unordered allele pairs ((0,1),(0,1)) corresponds to four distinct paths through the first three levels of the example diploid HMM for window w such as the sequence of diploid states (($\mathbb{S}_w$, $\mathbb{S}_w$),(u(w,1,0),u(w,1,1)),(u(w,2,1),u(w,2,2))). In addition, chromosome crossover may occur during meiosis. For various reasons, the phasing of a genotype dataset is not a deterministic process and, thus, there may be errors in phasing and determining a pair of haplotype sequence datasets from a genotype dataset.

The diploid HMM 300 may be used to generate a pair of phased haplotype datasets of an input genotype dataset for each window w. The input genotype dataset can be used with other training datasets to iteratively build the diploid HMM 300 for a predetermined number of iterations or until the diploid HMM 300 converges. For example, the diploid HMM 300 is initially trained with the reference panel samples obtained from the reference panel store 115. The reference panel samples may be unadmixed datasets or synthetic datasets for admixed populations. A different diploid HMM 300 may be computed and trained for each pair of labels using the reference panels associated with the pair of labels. The input genotype dataset may then be used as an input of the trained diploid HMM 300 to determine the Viterbi path of the diploid HMM 300. The Viterbi path may represent a likely outcome of a pair of phased haplotype datasets. The phased haplotype dataset may then be used as one of the training samples to improve the diploid HMM 300. This iteration may be repeated multiple times to improve the Viterbi path calculation and the phasing of the input genotype dataset. For more information on the phasing of an input genotype dataset to generate a pair of phased haplotype datasets, U.S. Patent Application Publication No. 2017/0262577 published Sep. 14, 2017, entitled "Haplotype Phasing Models," is incorporated by reference herein for all purposes.

The diploid HMM 300 may also be used to determine label pair probability distributions and emission probabilities. Such determination process will be discussed with further details below in association with FIG. 5.

Inter Window Hidden Markov Model

After a pair of phased haplotype datasets are generated from an input sample genotype dataset X, the label determination system 100 assigns labels to the input genotype dataset X by using and constructing an inter-window hidden Markov model (inter-window HMM). The genetic data store 130 stores one or more pairs of phased haplotype datasets. The label determination system 100 may assign labels to the input sample genotype dataset X based on the pair of phased haplotype datasets. The inter-window HMM store 135 stores an inter-window HMM corresponding to the input sample genotype dataset X that is used to determine the labels. The inter-window HMM is computed or built by the inter-window HMM module 160. The inter-window HMM includes states for each window w.

FIG. 4 illustrates a simplified example of an inter-window HMM 400, according to an embodiment. The inter-window HMM 400 may be a directed (e.g., in the direction from left to right as shown in FIG. 4) acyclic graph that includes a plurality of node groups. The graph representing the inter-window HMM 400 may also be referred to as a trellis. Graphically, each node group in the trellis may also be referred to as a level, a slot, a graph window, or a layer. Each node group represents a window w that corresponds to a genetic segment such as a set of SNPs. A plurality of nodes (represented by the circles in FIG. 4) are arranged in each node group. Each node represents a possible state of the window w. Each node is associated with an emission probability representing a likelihood of the window is observed as having a particular pair of phased haplotype datasets given the window is having the hidden state (i.e., the window is assigned with a particular pair of labels). In other words, the particular pair of phased haplotype datasets may be an observation in a hidden Markov model while the state that is labeled may be the "hidden" state of the hidden Markov model because the labels are not apparent given only the genotype dataset or the phased haplotype dataset.

The inter-window HMM 400 also includes a plurality of edges. Each edge connects a first node of a first node group to a second node of a second node group. Each edge represents a transition from the first node of the first node group to the second node of the second node group. Each edge is associated with a transition probability that represents a likelihood of transition from the first node to the second node. The determination of the emission probabilities and transition probabilities will be discussed in further details below in association with FIGS. 5 and 6.

A state (represented by a node) in the inter-window HMM 400 includes three different labels. In the particular embodiment shown in FIG. 4, the three labels are orderly presented as a first parent label, a second parent label, and a switch label that represents a switch of the order between the first parent label and the second parent label in the particular window, where the switching may be associated with phasing errors. While the order of presentation in the embodiment shown in FIG. 4 is the first parent label, the second parent label, and the switch label, other orders of presentation are also possible.

Each of the three labels in a state is represented by an integer value. For example, both the first parent label and the second parent label are selected from a set of K possible labels. A label is a classification of genetic data. For example, one possible way to classify genetic data is by ethnic origins of the individual, although other ways to classify genetic data are possible and are not necessarily based on or related to ethnic origins. If ethnic origins are used as classification, the set of K possible labels may be African, Asian, European, etc. or be German, Korean, Mexican, etc., depending on the granularity of the classification. A particular integral value represents one of the labels. For example, 1 may represent European while 2 may represent Asian.

The third label of a node, which is the switch label, may take a binary value (e.g., 1 or 0). The first binary value (e.g., 1) may represent that there is a switching of order of the first parent label and the second parent label while the second binary value (e.g., 0) may represent that there is no switching of order. A switch label represents a switching of order of the first parent label and the second parent label. In other words, a switch label represents that, for a particular state, the order of the first parent label and second parent label in the HMM is switched compared to the actual labels in the sample. Using the examples discussed in this paragraph as an illustration, the first node 402 of Window 1 in FIG. 4, which takes the values (1, 1, 0), may represent the state that Window 1 is labeled as European for both first parent label and second parent label and there is no switching of order between the two labels.

Likewise, the fourth node 404 of Window 1 in FIG. 4, which takes the values of (1, 2, 1), may represent the state that Window 1 is labeled as European for first parent label and Asian for second parent label but there is a switching of order between the two labels. In other words, due to one or more possible, but unobserved reasons such as a phasing error, the fourth node 404 in fact represents that Window 1 has Asian as first parent label and European for second parent label.

Using node 402 as an example to explain the concept of emission probability in the inter-window HMM 400, the emission probabilities here represent the likelihoods that Window 1 is observed in the sample genotype dataset to have a particular pair of phased haplotype datasets given the Window 1 should be labeled as having European origin for both first parent ancestry and second parent ancestry. Likewise, the transition probability from the node 402 to the node 406 represents the likelihood that a first segment of SNPs (corresponding to Window 1), which should be labeled as having European origin for both first and second parent ancestries, transitions to a second segment of SNPs (corresponding to Window 2) that should be labeled as having European origin for the first parent ancestry and European origin for the second parent ancestry, but there is a switching of first parent label and second parent label.

The plurality of nodes in each node group represents permutations of different possible first parent labels, second parent labels, and switch labels that can be assigned to a window. For each window, the inter-window HMM 400 may include a set of states corresponding to every ordered set of labels. Hence, the total number of states (T) can be K*K*2 (first parent labels K* second parent labels K* binary switch labels) for each window. For the particular embodiment shown in FIG. 4, there are three possible values of classification labels (i.e., K=3) and the switch label takes the value of either 1 or 0. Hence, there are 3*3*2=18 possible states (i.e., T=18). For simplicity, only some of the states are shown in FIG. 4 for each window. The states for a window w are denoted as $U_w(p,q,z)$ where p is the value of the first parent label (e.g., $p \in (1, 2, \ldots, K)$), q is the value of the second parent label (e.g., $q \in (1, 2, \ldots, K)$), and z is the value of the switch label (e.g., $z \in (0,1)$). In this way, the set of labels (p,q,z) uniquely refers to each of the possible states T. Although FIG. 4 depicts K=3 labels, the number of labels K can be any natural integers.

The inter-window HMM 400 is a directional graph that represents a transition from a start state to an end state (not shown in FIG. 4) through a plurality of node groups that represent a plurality of windows. The start state 410 transitions to one of the T possible states of window 1 as illustrated by the arrows between the start state 310 and the respective T states of window 1. Each state in window 1 may transition to one of the possible states in window 2. A state $U_w(p,q,z)$ in window w may transition to a state $U_{w+1}(p',q',z')$ in window w+1. The chromosome that corresponds to the window w is denoted as C(w) while the chromosome that corresponds to the window w+1 is denoted as C(w+1). If the window w and the window w+1 correspond to the same chromosome (i.e., C(w)=C(w+1)), then a state $U_w(p,q,z)$ may be more likely to transition to a state $U_{w+1}(p',q',z')$ in window w+1 that corresponds to the same pair of labels (i.e., (p',q')=(p,q)) without switching than to a state in window w+1 that corresponds to a different pair of labels or to a state in window w+1 that corresponds to a switching of labels. This is because it is biologically unlikely that the sequences of SNPs in adjacent windows will correspond to different labels (e.g., correspond to different ancestral origin groups).

In some embodiments, the transition probability $P(U_w(p,q,z), U_{w+1}(p',q',z'))$ from a state $U_w(p,q,z)$ to a state $U_{w+1}(p',q',z')$ is given by equation (1) below:

$$P(U_w(p, q, z) \to U_{w+1}(p', q', z')) = \begin{cases} \frac{\pi_{p'}^m \times \pi_{q'}^f}{2} & \text{if } C(w) \neq C(w+1) \\ (1-\tau^m) \times (1-\tau^f) \times (1-\tau^z) & \text{if } C(w) = C(w+1), p = p', q = q', z = z' \\ (1-\tau^m) \times (1-\tau^f) \times \tau^z & \text{if } C(w) = C(w+1), p = p', q = q', z \neq z' \\ \tau^m \times (1-\tau^f) \times (1-\tau^z) \times \frac{\pi_{p'}^m}{\sum_1^{p'-1} \pi_k^m + \sum_{p'+1}^K \pi_k^m} & \text{if } C(w) = C(w+1), p \neq p', q = q', z = z' \\ \tau^m \times (1-\tau^f) \times \tau^z \times \frac{\pi_{p'}^m}{\sum_1^{p'-1} \pi_k^m + \sum_{p'+1}^K \pi_k^m} & \text{if } C(w) = C(w+1), p \neq p', q = q', z \neq z' \\ (1-\tau^m) \times \tau^f \times (1-\tau^z) \times \frac{\pi_{q'}^m}{\sum_1^{q'-1} \pi_k^f + \sum_{q'+1}^K \pi_k^f} & \text{if } C(w) = C(w+1), p = p', q \neq q', z = z' \\ (1-\tau^m) \times \tau^f \times \tau^z \times \frac{\pi_{q'}^m}{\sum_1^{q'-1} \pi_k^f + \sum_{q'+1}^K \pi_k^f} & \text{if } C(w) = C(w+1), p = p', q \neq q', z \neq z' \\ 0 & \text{if } C(w) = C(w+1), p \neq p', q \neq q' \end{cases}$$

The symbol $\pi_k^m$ represents the label probability distribution of first parent label k over K different labels while $\pi_k^f$ represents the label probability distribution of second parent label k over K different labels. In some embodiments the label probability distributions may each correspond to a genome wide distribution, but in other embodiments the distributions may correspond to a portion of the genome. In some cases, the label probabilities over all different labels sum to unity (i.e., $\Sigma_{k \in K} \pi_k^m = \Sigma_{k \in K} \pi_k^f = 1$). The label probability distributions $\pi_k^m$ and $\pi_k^f$ indicates the preference of parent 1 and parent 2, respectively, for K different labels. For example, $\pi_p^m$, is the probability of first parent label of window w+1 taking the value k=p' over other possible values of labels K. C(w)=C(w+1) represents that the two windows correspond to the same chromosome. The label change probability $\tau^m$ represents the probability that first parent label will transition to a different label from window w to window w+1 (e.g., window w has a label of European while window w+1 has a label of Asian). In the embodiment that uses the equation above, the change of label depends on label probability $\pi_k^m$ and $\pi_f^m$. The label change probability $\tau^f$ represents the probability that second parent label will transition to a different label from window w to window w+1. The label switch probability $\tau^z$ represents the probability that the order of first parent label and the second parent label is switched (i.e. the state will transition to the opposite z assignment between two windows.)

Hence, in the above equation, the first scenario represents that two windows are located in different chromosomes and the transition probability $P(U_w(p,q,z),U_{w+1}(p',q',z'))$ is equal to the first parent label probability of k=p' times the second parent label probability of k=q' divided by 2. The second scenario represents that the two windows are located in the same chromosome and there is no change in label or switch of label order. The transition probability in this scenario is equal to one minus the first parent label change probability $\tau^m$ (because the label either change or does not change) times one minus the second parent label change probability $\tau^f$ times one minus label switch probability $\tau^z$. Other scenarios are modeled similarly in the equation above.

The values of label probabilities ($\pi_k^m$ and $\pi_k^f$), label change probabilities ($\tau^m$ and $\tau^f$), and the label switch probability (T Z) are determined by the training of the inter-window HMM 400 based on a set of training data and, in some embodiments, additionally with the pair of haplotype datasets derived from an input sample genotype dataset X. The values of label probabilities ($\pi_k^m$ and $\pi_k^f$) of different k may be represented in a vector form (also referred to as label probability vector). In some embodiments, the values of the label probability vector and the label change probabilities are calculated with a Baum-Welch algorithm. In some embodiments, it may be assumed that a transition from a state $U_w(p,q,z)$ to another state $U_{w+1}(p',q',z')$ without any of the same labels p, q (i.e., both values of first parent label and second parent label change in a transition) are impossible. Hence, the transition probability for the last scenario in the equation above is zero in some embodiments. By omitting a transition for these low-probability transitions, the complexity of the inter-window HMM 400 may be reduced, thereby producing significant savings in time and computer processing requirements needed to determine labels.

If the window w+1 corresponds to a different chromosome than window w, then the state $U_w(p,q,z)$ may transition to an inter-chromosome state 420, which, in turn, transitions to a state $U_{w+1}(p',q',z')$ in the next window w+1. Thus, if the window w+1 corresponds to a different chromosome than window w, the state $U_w(p,q,z)$ may transition to a state $U_{w+1}(p',q',z')$ with a probability that is independent of the state $U_w(p,q,z)$ at window w (i.e., independent of (p,q)) because of the intervening inter-chromosome state 420.

If window w is the final window (i.e., w=W), then the state $U_w(p,q,z)$ in the window w transitions to an end state (not shown in FIG. 4). Each state $U_w(p,q,z)$ in window w transitions to either a state $U_{w+1}(p',q',z')$ in window w+1, an inter-chromosome state 420, or an end state. FIG. 4 illustrates the possible outgoing transitions for each state $U_w(p,q,z)$ with arrows. For example, in window 2 (and in all windows w in which the window w+1 is on the same chromosome), the state 406 $U_2(1,2,1)$ may transition to the states $U_3(1,1,0)$, $U_3(1,1,1)$, $U_3(1,2,0)$, $U_3(1,2,1)$, etc. However, the state 406 $U_2(1,2,1)$ may not transition to state $U_3(3,3,0)$ because of both the first parent label and second parent label change in the transition. As such, no arrow connects the state 406 $U_2(1,2,1)$ to the state $U_3(3,3,0)$ in FIG. 4.

Annotations and Emission Probability

In FIG. 4, each node (representing a state of a window) is associated with an emission probability that represents a likelihood of the window is observed as having a particular pair of phased haplotype datasets given the window is in the hidden state represented by the node. The determination of the emission probability is based on genotype data of different reference panels and the input genotype dataset X through one or more intermediate steps that may include determinations of annotations, annotation products, and label pair probabilities. The details of the determination of the emission probability is discussed below.

Returning first to FIG. 1A, the reference panel sample store 115 stores a set of reference panel samples of genotype datasets for each of the K labels. A reference panel for kth label is a collection of representative genetic datasets that belong to a community corresponding to kth label. For example, if the kth label represents a community of individual of an Asian reference panel, the reference panel samples in the kth-label reference panel are representative Asian genotype datasets. For more details on how reference panel samples may be identified and/or generated, U.S. Patent Application Publication 2016/0350479 published on Dec. 1, 2016, entitled "Discovering Population Structure from Patterns of Identity-by-Descent," is incorporated by reference herein for all purposes. The set of reference panel samples corresponding to the kth label (for k∈{1, ..., K}) is referred to herein as $R_k$. Each reference panel sample $R \in R_k$ in the store 115 may be phased diploid genotype dataset of L SNPs, $R=(R_1, ..., R_L)$, where each $R_i$ (for i∈{1, ..., L}) is an SNP that is an ordered pair of binary alleles (i.e., (0,0), (0,1), (1,0) or (1,1)). At some sites of SNPs, there may be missing data. The labels may each correspond to a different origin population (e.g., an ethnic group), in which case each reference panel sample R may be a genotype data with a single origin from the kth origin population.

The possible labels may include both unadmixed labels and admixed labels. A collection of reference panel samples may be retrieved. The collection may include a plurality of unadmixed genetic datasets and a plurality of admixed synthetic genetic datasets. An admixed synthetic genetic dataset may be associated with both an ethnic origin and a geographical origin. For an admixed population, the same ethnic origin but with different geographical origins may be regarded as a different label. For labeling an admixed individuals, at least some of the nodes in the inter-window HMM 400 may be labeled with a particular ethnic origin associated with an admixed population from a geographical origin. Other nodes in the inter-window HMM 400 may be labeled with another ethnic origin associated with the admixed population from the geographical origin. For example, in FIG. 4 shown, label 1 may be associated with Mexico-Native American while label 2 may be associated with Mexico-European.

Figure 5:
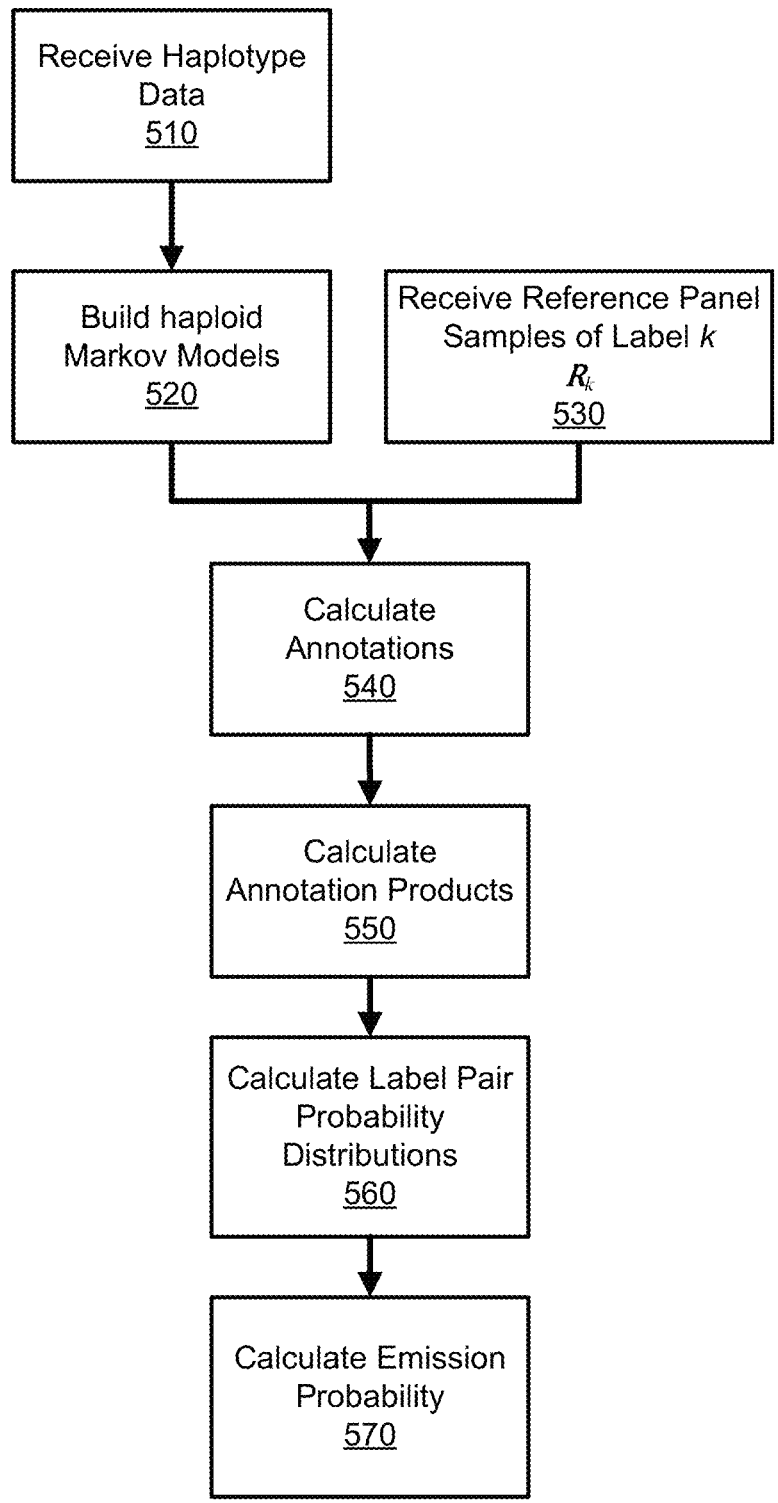
FIG. 5 is a flowchart illustrating a process for calculating emission probability, according to some embodiments.

Now referring to FIG. 5, a flowchart depicting a process for calculating emission probabilities is illustrated, according to some embodiments. The label determination system 100 receives 510 haplotype data of a training set. The haplotype data may be a sequence of alleles corresponding to individuals. Each sequence of haplotype data may include alleles corresponding to the L SNPs of the genotypes stored in the genetic data store 130, or some subset thereof. the reference panel sample store 115 stores a set of reference samples for each of the K labels. The set of reference panel samples corresponding to the kth label (for k∈{1, ..., K}) is referred to herein as $R_k$. Each reference panel sample $R \in R_k$ in the store 115 may be an unphased diploid genotype of L SNPs, $R=(R_1, ..., R_L)$, where each $R_i$ (for i∈{1, ..., L}) is an SNP that is either an unordered pair of binary alleles (i.e., (0,0), (0,1), or (1,1)) or missing data. The labels may each correspond to a different origin (e.g., an ethnic group), in which case each reference panel sample R may be a genotype from the kth origin population.

Some or all of the haplotype data may be phased haplotype data produced by the method described in the PCT application entitled "Haplotype Phasing Modules" (International Publication Number WO 2016/061568 A1) which was filed on Oct. 19, 2015 and which is hereby incorporated by reference in its entirety. In alternate embodiments, some or all of the haplotype data may be phased haplotypes produced by PHASE, BEAGLE, HAPI-UR, SHAPEIT2, IMPUTE2, or some other phase estimation method. Based on the received haplotype data, the label determination system 100 builds 520 haploid MMs 200 for each window w. The haploid MMs may be stored in the haploid MM store 110.

The label determination system 100 also receives 530 a set of reference panel samples $R_k$ for each label k (for $1 \le k \le K$). The set of reference panel samples $R_k$ may be accessed from the reference panel sample store 115. Based on the set of reference panel samples $R_k$ for label k and the haploid MMs for window w, the label determination system 100 calculates 540 a set of annotations $A_w(k,u)$ of every label k and every state u in the window w. The annotations $A_w$ may be stored in the annotation store 125. The label determination system 100 calculates 550 annotation products $L_w(d, p)$ based on the annotations. Based on the annotation products $L_w(d, p)$, the label determination system 100 calculates 560 label probability distributions. Based on the label pair probability distributions $E_{x,w}(p,q)$, the label determination system 100 calculates 570 the emission probability for each node. For an admixed individual, at least some of the nodes in the inter-window HMM 400 may be assigned with probabilities that are calculated based on one or more synthetic genetic datasets.

Annotation Determination

The discussion in this subsection corresponds to element 540 in FIG. 5 regarding calculation of annotation in association with the calculation of emission probabilities. The annotation $A_w(k,u)$ is based on a calculation of the conditional probability of the haploid state u given the SNP sequence in the window w for the reference panel sample R that belongs to the set of reference panel samples $R_k$ of the kth label. The calculation of the probability of the state u given reference panel sample R is based on the haploid MM 200 for window w. For a given window w, label k, and state u, the annotation $A_w(k,u)$ is equal to or positively correlated with the probability that a haplotype corresponding to label k includes the haploid state u in its path through window w. Equivalently, the annotation $A_w(k,u)$ may be or may represent the expected proportion of haplotypes that include haploid state u in their corresponding paths for genotypes datasets selected from the set of reference panel samples $R_k$.

In one embodiment, annotations are determined using a forward-backward algorithm. For a reference panel sample $R \in R_k$, the forward-backward algorithm may be used to calculate a forward function $f_{R,w}$ and a backward function $b_{R,w}$. The forward function $f_{R,w}(u,v)$ may map the diploid state (u,v) at level d to the joint probability of the first d SNPs in window w of the reference panel sample R and the diploid state (u,v). That is, the output of the forward function $f_{R,w}(u,v)$ is the probability, based on the haploid MM for the window w, that a genotype dataset has the first d SNPs of R and that R corresponds to the state (u,v) at level d. Similarly, the backward function $b_{R,w}(u,v)$ may map the diploid state (u,v) at level d to the joint probability of the last (D-d) SNPs in window w of the reference panel sample R and the state (u,v). The forward-backwards product, $f_{R,w}(u,v) \times b_{R,w}(u,v)$, may be the joint probability of all the SNPs of the reference panel sample R in window w and the corresponding state (u,v). In some embodiments, the outputs of the forward function $f_{R,w}$ and the backward function $b_{R,w}$ are proportional, but not necessarily equal to the probabilities of their respective diploid states.

The annotation $A_w(k,u)$ for the label k and state u may be given by:

$$A_w(k, u) = \frac{1}{|R_k|} \sum_{R \in R_k} \frac{1}{b_{R,w}(\mathbb{S}_w, \mathbb{S}_w)} \sum_{v \in StatesInLevel_w(u)} f_{R,w}(u, v) \times b_{R,w}(u, v) \quad (1)$$

where $|R_k|$ denotes the cardinality of the set $R_k$ (i.e., the number of reference panel samples in $R_k$) and where $StatesInLevel_w(u)$ refers to the set of haploid states in the same level as u (i.e., if u is in level d, then $StatesInLevel_w(u)$ is the set of all states at level d). Because ($\mathbb{S}_w, \mathbb{S}_w$) is the start state of the diploid HMM 300 for window w, $b_{R,w}(\mathbb{S}_w, \mathbb{S}_w)$ is equal to the likelihood of the reference panel sample R.

By the definition of the conditional probability, $f_{R,w}(u,v) \times b_{R,w}(u,v)/b_{R,w}(\mathbb{S}_w, \mathbb{S}_w)$ is the diploid state probability, i.e., the conditional probability that the path of a genotype dataset includes the state (u,v) in the diploid HMM 300 for window w given that the genotype dataset is a reference panel sample R. In some embodiments, the forward-backwards product $f_{R,w}(u,v) \times b_{R,w}(u,v)$ and $b_{R,w}(\mathbb{S}_w, \mathbb{S}_w)$ are calculated to be proportional, but not necessarily equivalent, to the likelihood of their respective diploid states. In such an embodiment, the diploid state probability $f_{R,w}(u,v) \times b_{R,w}(u,v)/b_{R,w}(\mathbb{S}_w, \mathbb{S}_w)$ for reference panel sample R is still equivalent to the conditional probability that the path of the genotype includes the state (u,v) in the diploid HMM 300 given the genotype R.

The summation of the diploid state $f_{R,w}(u,v) \times b_{R,w}(u,v)/b_{R,w}(\mathbb{S}_w, \mathbb{S}_w)$ over all haploid states v in level d produces the marginal probability that the first haplotype (e.g., paternal, or maternal) is in haploid state u at level d given the reference panel sample R. The diploid state probabilities for a reference panel sample R may be summed over the set of diploid states that include the haploid state u (i.e., diploid states (u,v) and (v,u) for all haploid states v at the same level as the haploid state u) to produce a probability that the reference panel sample R corresponds to the haploid state u. Finally, the probabilities of u for each reference panel sample R may be combined to produce the annotation $A_w(k,u)$. For example, $A_w(k,u)$ may be the arithmetic average of the probabilities of the haploid state u for each reference panel sample R, therefore representing the expected proportion of reference panel samples in the set of reference panel samples $R_k$ that include the state u in their respective paths. Stated differently, the annotation $A_w(k,u)$ is the probability that the haploid state of a haplotype at a level d is haploid state u given that the haplotype corresponds to label k. In other alternatives, a different mathematical formulation other than arithmetic average may be used.

The annotations in the annotation store 125 may be calculated prior to determining labels for potentially admixed genotype datasets. In some embodiments, the annotations are updated based on labels determined for phased potentially admixed genotype datasets that are input to the system through the process described herein. In some embodiments, the annotations $A_w(k,u)$ for a label k and window w may be iteratively improved by determining a probability that an admixed genotype dataset corresponds to a label k in window w and modifying the annotations $A_w(k,u)$ accordingly.

Annotation Product Determination

Figure 6:
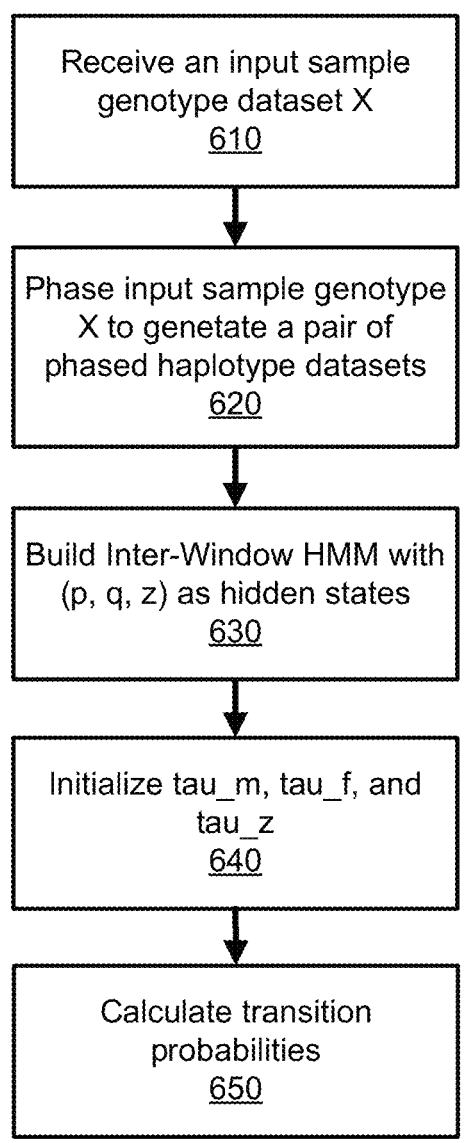
FIG. 6 is a flowchart illustrating a process for computing a hidden Markov model, according to some embodiments.

The discussion in this subsection may correspond to element 550 in FIG. 5 regarding calculation of annotation products in association with the calculation of emission probabilities. FIG. 6 is a flowchart illustrating a method for assigning labels to a genotype, according to some embodiments. The label determination method 600 may be performed by the label determination system 100.

Based on the annotations $A_w(k,u)$ and the input sample genotype dataset X, which is divided into two phased haplotypes, $x_{1,w}$ and $x_{2,w}$ each a sequence of alleles $\in\{0,1\}$ corresponding to the subsequence of SNPs in window w, the haploid MM module 140 may calculate a label probability $E_{x,w}(p)$ for each haplotype $x \in \{x_{1,w}, x_{2,w}\}$, and each label $p \in \{1, 2, \ldots, K\}$, where K is the number of possible labels. If window w is a subsequence of $D_w$ SNPs, the haploid MM module 140 determines a unique set of states $\{u_{x,w,0}, u_{x,w,1}, u_2, \ldots, u_{x,w,Dw}\}$ for a haplotype subsequence x in window w and the label probability for label p for a haplotype x is given by $$E_{x,w}(p) = \frac{1}{D_w} \sum_{d=0}^{D_w} \frac{A_w(p, u_{x,w,d})}{\sum_{k=1}^{K} A_w(k, u_{x,w,d})}$$

The annotation product corresponds to haplotype $x_1$ (one of the phased haplotypes) at window w. $E_{x1,w}(p)$ represents the likelihood that the window w corresponds to label p given that the haplotype is $x_1$. Another annotation product $W_{x2,w}(p)$ is calculated similarly for the other phased haplotype $x_2$.

Based on the label pair probability distributions for each window w, the inter-window HMM module 160 may build an inter-window HMM 400. The transition probabilities between states in the inter-window HMM may be based on the label pair probability distribution. Also, the inter-window HMM module may use the label pair probability distribution as the probability distribution of the states in window w given the SNPs in the window w. That is, the label pair probability distribution may be used in the inter-window HMM as the probability of the state $U_w(p,q,z)$ in window w given the observation (i.e., the sequence of SNPs of the phased datasets in the window w). Computing the inter-window HMM 400 for the phased datasets may include determining a label probability vector and label change probabilities for the inter-window HMM.

In some embodiments, the inter-window HMM module 160 uses the label pair probability distribution to calculate the emission probabilities for states in window w. That is, the label pair probability may be an estimate of the probability of the sequence of SNPs in window w given that the state for window w is $U_w(p,q,z)$. Here $x_1$ and $x_2$ are two phased haplotypes. The emission probability is determined based on the following equation:

$$E_{x,w}(p, q, z) = \begin{cases} E_{x1,w}(p) \times E_{x2,w}(q) & \text{if } z = 0 \\ E_{x1,w}(q) \times E_{x2,w}(p) & \text{if } z = 1 \end{cases}$$

Alternatively, based on the annotations $A_w(k,u)$ and the input sample genotype dataset X, the diploid HMM module 150 may calculate a label pair probability $E_{x,w}(p,q,z)$ as an estimate of the probability of the sequence of SNPs in window w given that the state for window w is $U_w(p,q,z)$ as $$E_{x,w}(p, q, z) = \sum_{d=0}^{D_w} \frac{L_{x,w}(p, q)}{\sum_{p',q'} L_{x,w}(p', q')}$$

where $L_{x,w}(p,q)$ is the expected annotation product given by $$L_{x,w}(p, q) = \sum_{u,v \in \alpha_d} \frac{f_{x,w}(u,v) \times b_{x,w}(u,v)}{b_{x,w}(\mathbb{S}_w, \mathbb{S}_w)} \times \frac{A_w(p,u) \times A_w(q,v) + A_w(q,u) \times A_w(p,v)}{2}$$

And $f_{x,w}(u,v) \times b_{x,w}(u,v)/b_{x,w}(\mathbb{S}_w, \mathbb{S}_w)$ is the diploid state probability, e.g., the conditional probability that the path of a genotype dataset x includes the state (u,v) in the diploid HMM 300 for window w. $\mathbb{S}_w$ is the distinguished started state in the diploid HMM 300, and $\alpha_d$ is the set of states in the diploid HMM 300 at level d. Note that when using the diploid HMM this way to determine the label pair probability, $E_{x,w}(p, q, z)$ does not depend on z.

Computing the Inter-Window HMM

FIG. 6 depicts a process for building and computing an inter-window HMM, in accordance with some embodiments. The label determination system 100 receives 610 an input sample genotype dataset X. The label determination system 100 phases 620 the input sample genotype dataset X to generate a pair of phased haplotype datasets. The pair of phased haplotype datasets may be generated using the diploid HMM 300. The label determination system 100 builds 630 an inter-window HMM with (p, q, z) as labels of the hidden states. The label determination system 100 initializes 640 the label change probabilities $\tau^m$ and $\tau^f$ and the label switch probability $\tau^z$ when computing the inter-window HMM. The label change probabilities and the label switch probability may be initialized to a low value (e.g., between 0.5 to $10^{-4}$) and iteratively updated. After a predetermined number of rounds of iteration and/or after the values of label change probabilities and label switch probability have converged, the label determination system 100 calculates 650 the transition probabilities for different possible transitions.

The calculation of label probability vector, label change probabilities, and label switch probability may be carried through one or more forward-backward algorithms. Computing the inter-window HMM may include calculating a label probability vector and the label change probabilities. The label probability vector may be initialized to a uniform distribution. The label probability vector may be iteratively updated with expectation-maximization (e.g., with the Baum-Welch algorithm). In some embodiments, the inter-window HMM module may perform N iterations of the Baum-Welch algorithm to calculate the label probability vector. The label change probability and the label switch probability may be initialized to a low value (e.g., between 0.5 to $10^{-4}$) and iteratively updated.

In one example, a label pair expectation $E[\pi_{X,(p,q)}]$ is calculated for each of the pair of labels (p,q). The label pair expectation $E[\pi_{X,(p,q)}]$ is the sum of the probabilities of each state $U_{w,(p,q)}$ for each window w and is therefore equal to the expected number of windows w that have a hidden state $U_{w,(p,q)}$ corresponding to the label pair (p,q). Each label probability $\pi_{(p,q)}$ is updated to a new value: the label pair expectation $E[\pi_{X,(p,q)}]$ of the label pair (p,q) divided by the sum of label pair expectations for all label pair probabilities, so that the label probabilities $\pi_{(p,q)}$ sum to unity (i.e., $\Sigma\pi=1$).

In one example, the label change probability $\tau^m$ and $\tau^f$ are each initialized to $10^{-3}$ and then iteratively updated to the expected number of transitions that change label assignments. Put differently, the label change probability is updated to the complement of the expected number of transitions between states that correspond to the same labels (e.g., one minus probability of no change in label) divided by the expected number of all transitions between states. Likewise, the label switch probability $\tau^z$ may also be initialized to a low value then iteratively updated.

Label Assignment

Figure 7:
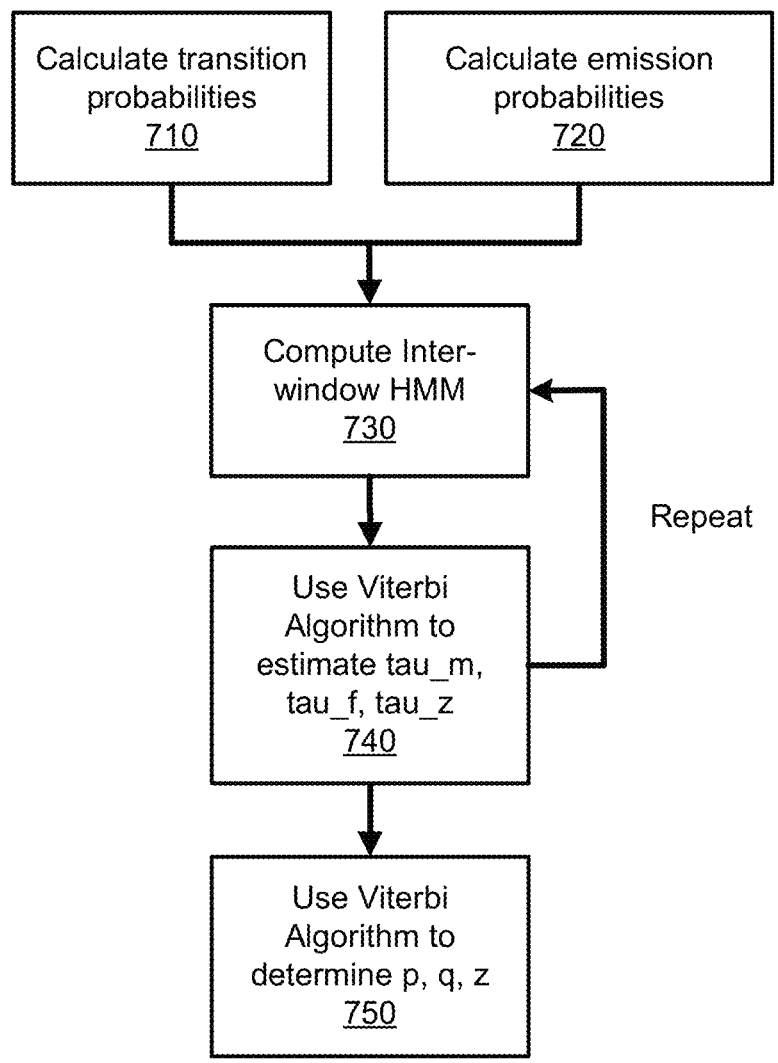
FIG. 7 is a flowchart illustrating a process for assigning labels to a genotype dataset, according to one embodiment.

FIG. 7 illustrates a process of providing a label assignment of an input genotype dataset, in accordance with an embodiment. Using a set of training samples such as those obtained from different reference panels, the label determination system 100 calculates 710 transition probabilities for different possible transitions for an inter-window HMM in the training of the inter-window HMM. The calculation of transition probabilities may correspond to the process shown in FIG. 6. Based on the reference panel samples and the input sample genotype dataset X, the label determination system 100 calculates 720 the emission probabilities for different hidden states in the inter-window HMM. The calculation of the emission probabilities may correspond to the process shown in FIG. 5. The label determination system 100 updates and builds (e.g., computes) 730 an inter-window HMM using the pair of phased haplotype datasets derived from the input sample genotype dataset X. The computation may include generating data representing a directed acyclic graph that may include the structure of the inter-window HMM 400. The label determination system 100 uses 740 Viterbi algorithm to estimate the label change probabilities and the label switch probability in the updated inter-window HMM. Based on the Viterbi path, the labels corresponding to the input sample genotype dataset X are determined. The determined Viterbi path may be used as one of the samples of a new set of training samples (which include the selected training samples from reference panels and the determined Viterbi path as an additional sample) to update and re-build 730 the inter-window HMM. The process of 730 and 740 can be repeated for a predetermined number of iterations (e.g., 10 times) and/or repeated until the label changes probabilities and the label switch probability converge. The label determination system 100 uses 750 the Viterbi algorithm one more time to determine the Viterbi path corresponding to the input sample genotype dataset X to assign the value of labels p, q and z in each window. A final path may be determined after repeating the Viterbi algorithm multiple times. The final path may traverse the directed acyclic path and may represent the a statistically likely path among other possible paths in traversing the directed acyclic graph.

In some embodiments, the label assignment may involve determining a proportion of the input sample genotype dataset X that corresponds to each label. For example, the label assignment module 170 of the label determination system 100 may determine that 25% of the input sample genotype dataset X corresponds to label 1, 0% corresponds to label 2, 50% corresponds to label 3, and 25% corresponds to label 4. The proportion of each label may be based on the states in the Viterbi path, based on the probability of being in each state (e.g., as calculated with the forward-backward algorithm), or otherwise based on the inter-window HMM.

The determination of these proportions may also be based on a weight assigned to each window w. The weight of each window w may be based on the size of the window (e.g., in the number of bases). The weighting of each window w may be adjusted based on portions of the windows w that overlaps with other windows.

In some embodiments, the label assignment module 170 assigns a pair of ordered classification labels to each window w of the input sample genotype dataset X. In some embodiments, the label assignment module 170 determines the Viterbi path through the inter-window HMM 400. In alternate embodiments, the label assignment module 170 computes a number (e.g., 1000) of stochastic paths through the inter-window HMM and determines a range of each label's proportion based on the states taken by the stochastic process. For example, the label assignment module 170 may determine that 18-30% of the input sample genotype dataset X corresponds to a particular label. The range may be based on the maximum and minimum proportion of the genotype dataset X that corresponds to a label in the stochastic paths. Alternately, the range may be based on percentiles of the proportions of the input sample genotype dataset X that corresponds to a label in the stochastic paths. For example, the upper bound of a range for label k may be based on a 95th percentile of the proportions of the states that correspond to label k in the stochastic paths and the lower bound may be based on the 5th percentile. The most probable path or one of 95th percentile (or another suitable percentile) likely stochastic paths among other possible paths in traversing the directed acyclic graph may be referred to as a statistically likely path. Further details regarding determining different paths and range are discussed with reference to the Section below entitled "Range Determination."

In some embodiments, the label assignment module 170 assigns labels to specific portions of the input sample genotype dataset X. The label assignment module 170 may specifically assign labels to a portion of the input sample genotype dataset X that corresponds to one or more overlapping regions with a second genotype. For example, if the input sample genotype and the second genotype dataset are the genotypes of related individuals (e.g., first cousins), then the one or more overlapping regions are the regions of genetic information that correspond to one or more shared ancestors (e.g., a grandmother and a grandfather shared by the cousins). If, in an overlapping region, there is only one haplotype (in each genotype) that overlaps between the input sample genotype dataset X and the second genotype dataset, the label assignment module 170 may assign labels specifically to the overlapping haplotype.

For an admixed individual, the label determination and assignment may be similar but each label may include an ethnic origin and a geographical region. For example, a label for a particular window may be labeled with the ethnic origin Native America and with the geographical region of Mexico. A genetic segment that includes one or more consecutive windows may be assigned with the same label having the same ethnic-origin-geographical-region pair. The genetic segment may be added to one of the synthetic genetic datasets as part of a reference panel sample for an admixed population.

Providing Information on Ethnic Origin

Figure 8:
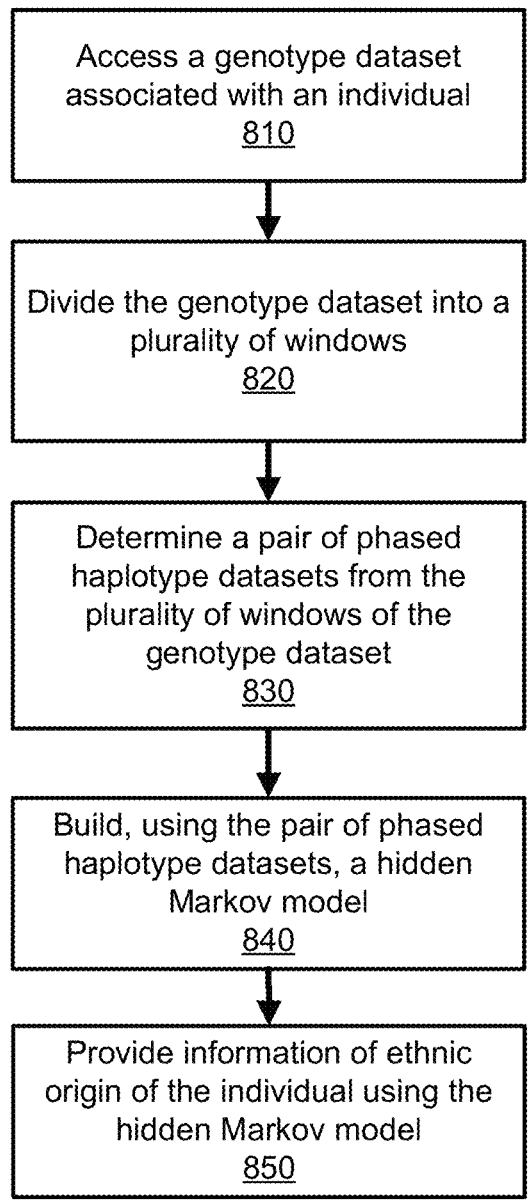
FIG. 8 is a flowchart illustrating a process for providing information of ethnic origin of an individual based on the individual's genotype dataset, according to one embodiment.

FIG. 8 depicts a process of providing information on ethnic origin for an individual such as an end user, in accordance with an embodiment. The label determination system 100 accesses 810 a genotype dataset associated with an individual. The genotype dataset may be stored in a data store after the biological sample (such as blood or saliva sample) of the individual to is analyzed to generate the genotype dataset sample. The label determination system 100 divides 820 the genotype dataset into a plurality of windows. Each window comprises a plurality of SNPs. The label determination system 100 determines 830 a pair of phased haplotype datasets from the plurality of windows of the genotype dataset. The label determination system 100 builds 840 a hidden Markov model using the pair of phased haplotype datasets. The HMM may be an inter-window HMM. Using the HMM computed and trained, the label determination system 100 assign labels to each window correspond to the genotype dataset based on the Viterbi path of the HMM. The nodes traversed by the Viterbi path each is associated with a first parent label and a second parent label. The statistic of the plurality of labels of the nodes can be determined. For example, the distribution of each label in terms of percentage may be determined. The label determination system 100 then provides 850 information of the ethnic origin of the individual using the results of the label assignment of the HMM. The label determination system 100 may provide a front-end user graphical interface for the presentation and display of the information of the ethnic origin of the individual, who may be an end user of the label determination system 100.

The information on the ethnic origin of the individual may take different forms. In a first example, the information may simply be the most likely ethnical origin of the individual. The label determination system 100 may simply inform the individual that he/she is of a certain origin. In a second example, the information may include paternal origin and maternal origin. In a third example, the information may include the statistic and/or the detailed proportions of genetic origins. For instance, the label determination system 100 may inform the individual that, on one parental side, 80% of the genes of the individual are inherited from European ancestors (e.g., based on 80% of first parent labels being European), while 15% of the genes are inherited from Asian ancestors, etc. In a fourth example, the information may take the form of a visualization of the individual's ancestry composition by chromosome painting. For example, an end user may want to know what parts of his DNA come from his African ancestors. The label determination system 100 may highlight portions of the chromosomes that correspond to windows that are labeled as African. In a fifth example, the information may take the form that is specifically related to a trait or phenotype. For example, an end user may select a question regarding from whom ancestor she received her blue eyes. The label determination system 100 may provide an answer to this type of questions such as in the form of "You inherit X trait from Y ancestor." In a sixth example, the information may take the form that is related to an ancestor. For instance, the label determination system 100 may provide that the end user share 60% of DNA when compared to a particular ancestor. In a seventh example, the information may take the form that compares the similarity and differences of the genotypes between the individual's father and mother (or paternal ancestors and maternal ancestors). In an eighth example, the information may take the form that focuses on other people who are genetically related to the individual. For instance, the label determination system 100 may provide the percentage of people of a certain ethnicity at trait loci has blue eyes. Other forms of information of ethnic origin of the individual are also possible.

For a target admixed individual, the information of ethnic origins of the individual may include information of genetic composition of the individual having a particular ethnic origin. For example, after a statistically likely path is determined based on the result of the HMM, the number of nodes that are labeled with a particular ethnic origin and a particular geographical region and that are included in the path may be calculated and compared to the total numbers of windows to determine the percentage of the particular ethnic origin of the target admixed individual. In one embodiment, in providing the genetic composition of a particular ethnic origin of an admixed individual, the label determination system 100 may distinguish the particular ethnic origin from two different geographical regions. For example, the label determination system 100 may report that the target admixed individual has 20% Native American genetic segments from Mexican ancestors and 15% Native American genetic segments from Brazilian ancestors. In another embodiment, the label determination system 100 may distinguish the geographical regions when assigning labels, but combine the same ethnic origin from different geographical origins together when reporting the result. For example, the label determination system 100 may report that the target admixed individual has in total 35% Native American origin, regardless of whether the genetic segments are labeled with Mexico or Brazil.

Figure 9:
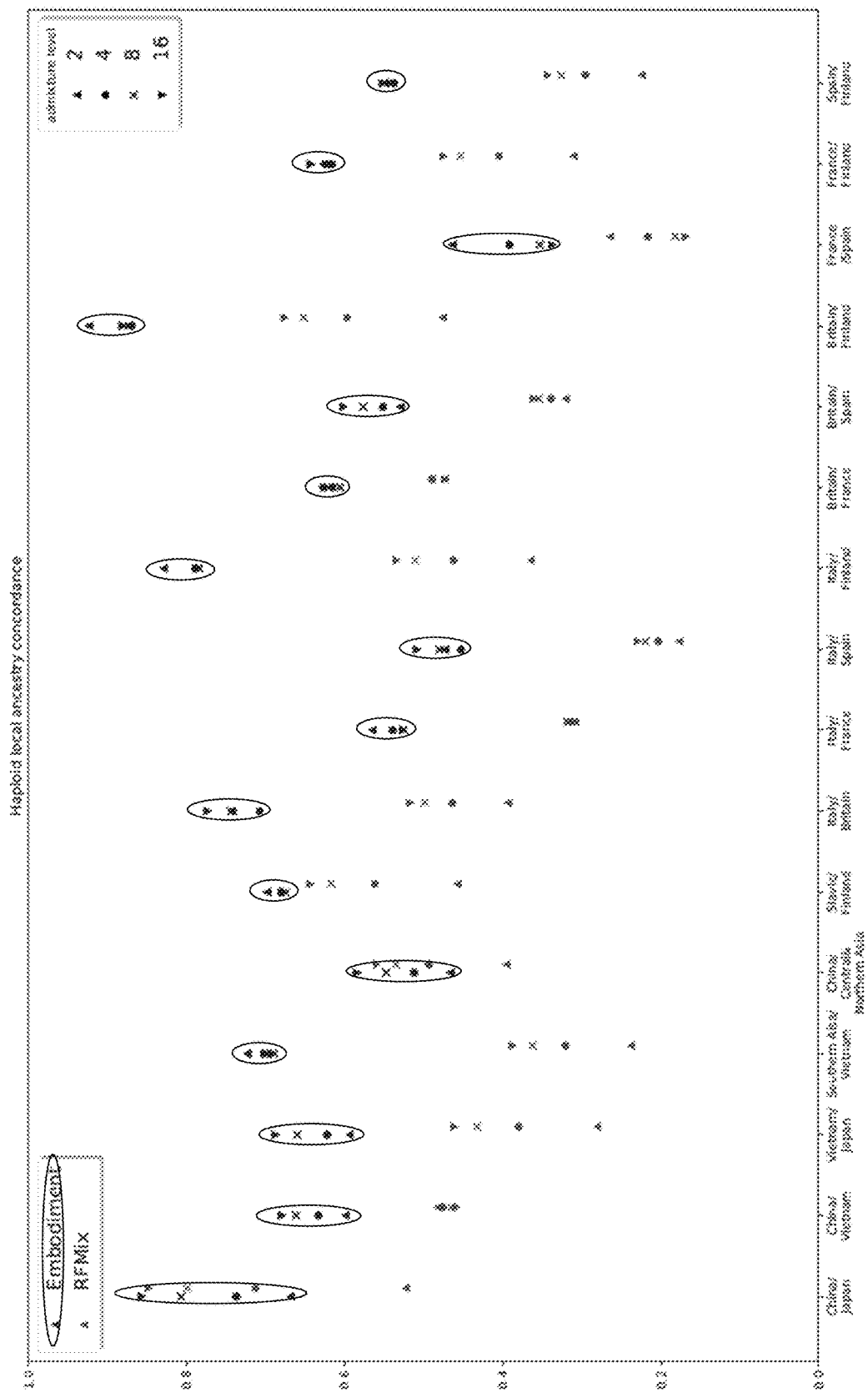
FIG. 9 is a plot of example experimental results of admixed individuals comparing accuracy of an embodiment described herein to a conventional ancestry determination method RFMix.

FIG. 9 is a plot of example experimental results of admixed individuals comparing the accuracy of an embodiment described herein to a conventional ancestry determination method RFMix. An experiment is conducted using an example inter-window HMM 400 described herein on simulated admixed individuals. Sixteen (16) different pairings of ethnicities are considered and the accuracy of ancestry assignments are measured. The haploid accuracy results are compared to ancestry assignments using a conventional method RFMix described in the article "RFMix: A Discriminative Modeling Approach for Rapid and Robust Local Ancestry Inference" by Brian K Maples et al. In FIG. 9, the plots for the example inter-window HMM 400 are circled. As shown, the inter-winder HMM 400 consistently outperforms the RFMix method among different admixed populations.

Figure 10:
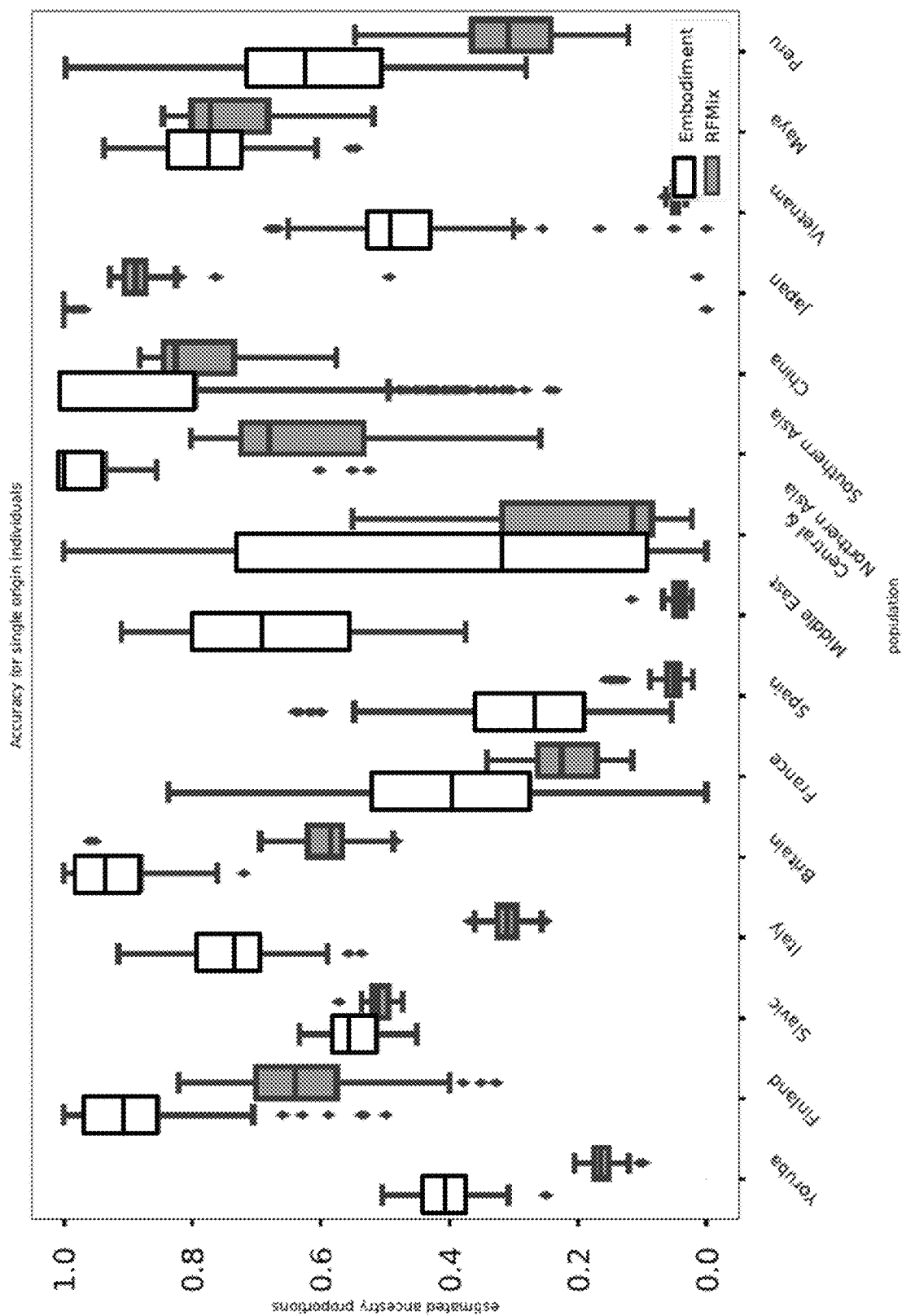
FIG. 10 a plot of example experimental results of unadmixed individuals comparing accuracy of an embodiment described herein to RFMix.

FIG. 10 a plot of example experimental results of unadmixed individuals comparing the accuracy of an embodiment described herein to RFMix. In this example experiment, the performance of an example inter-window HMM 400 on unadmixed (single-origin) individuals from 1000 genomes and HGDP (Human Genome Diversity Project) is studied. Fifteen (15) regions using a reference panel that is built from research consented individuals who represent thirty one (31) ethnicities is tested. The results are again compared to those using the RFMix method. As shown in FIG. 10, each population has two results. The left one is the result using the example inter-window HMM 400 while the right one is the result using the RFMix method. FIG. 10 shows that the example inter-window HMM 400 also consistently outperforms the RFMix method among different unadmixed individuals.

Figure 11A:
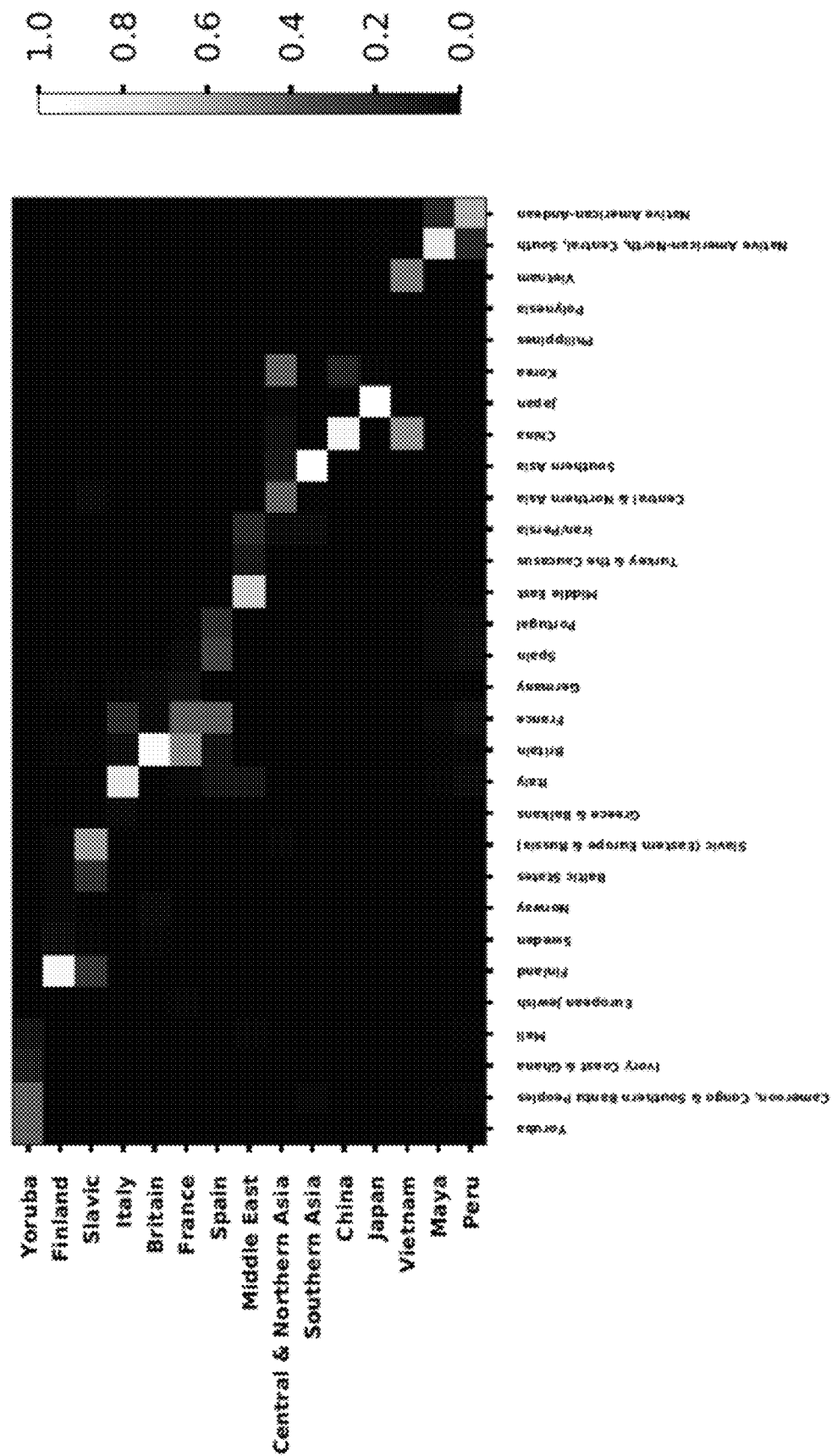
FIG. 11A is a plot of example results of an experiment that estimates ethnicities of single-origin individuals using an embodiment described herein.
Figure 11B:
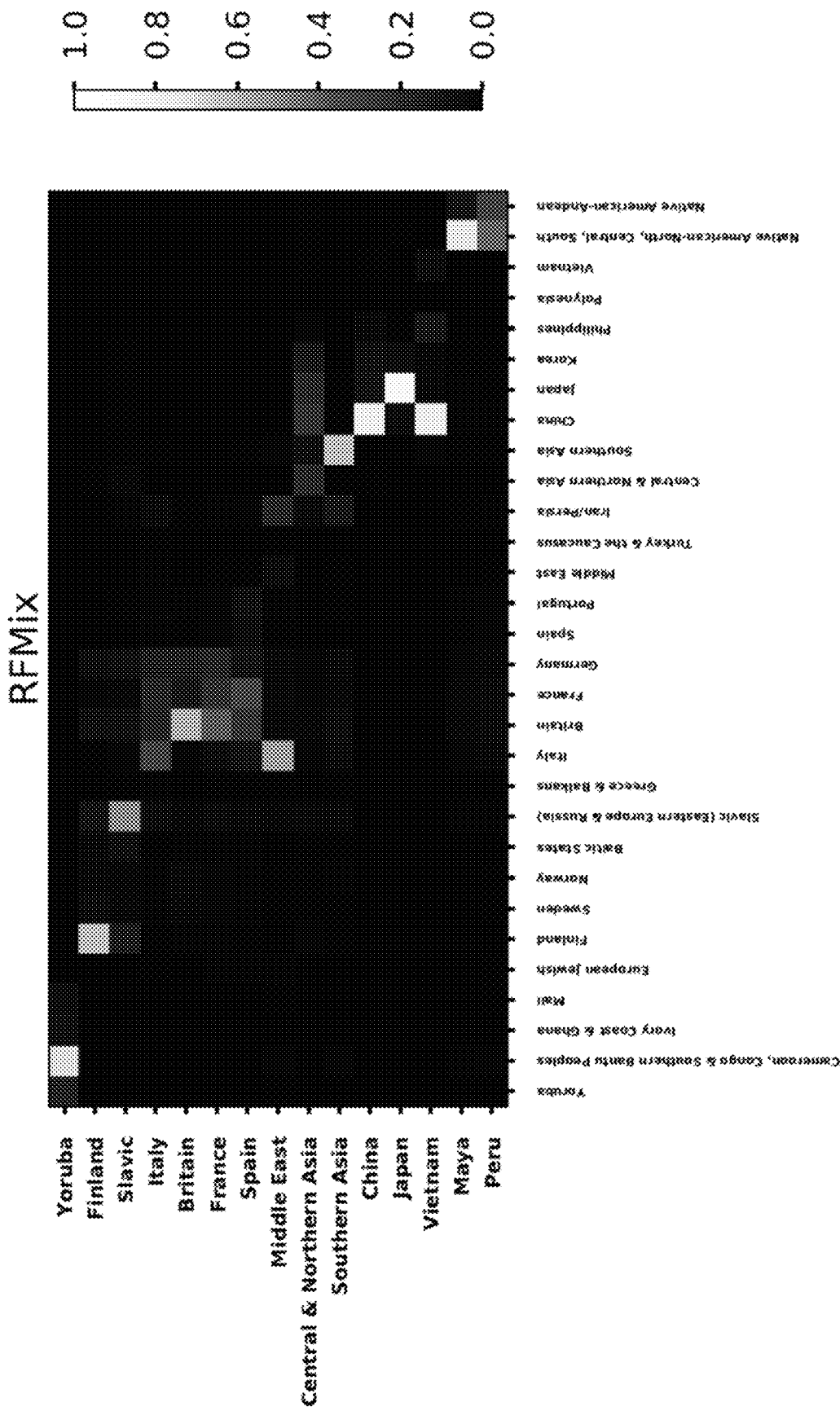
FIG. 11B is a plot of an experiment similar to that of FIG. 11A using RFMix.

FIG. 11A is a plot of example results of an experiment that estimates ethnicities of single-origin individuals using an embodiment described herein. FIG. 11B is a plot of the result of an experiment similar to that of FIG. 11A using RFMix. In those experiments, the ethnicities for single-origin from different populations are estimated using either an example inter-window HMM 400 or RFMix. In both figures, the rows represent single origin individuals from fifteen (15) regions. The columns represent thirty one (31) ethnicities to which the single-origin individuals might be assigned. By comparing FIG. 11A to FIG. 11B, the results again show the example inter-window HMM 400 outperforms RFMix. The example inter-window HMM 400 shows better accuracy for different ethnicities. The plot in FIG. 11A also forms a better diagonal line, indicating the assignments are improved over RFMix.

Figure 12:
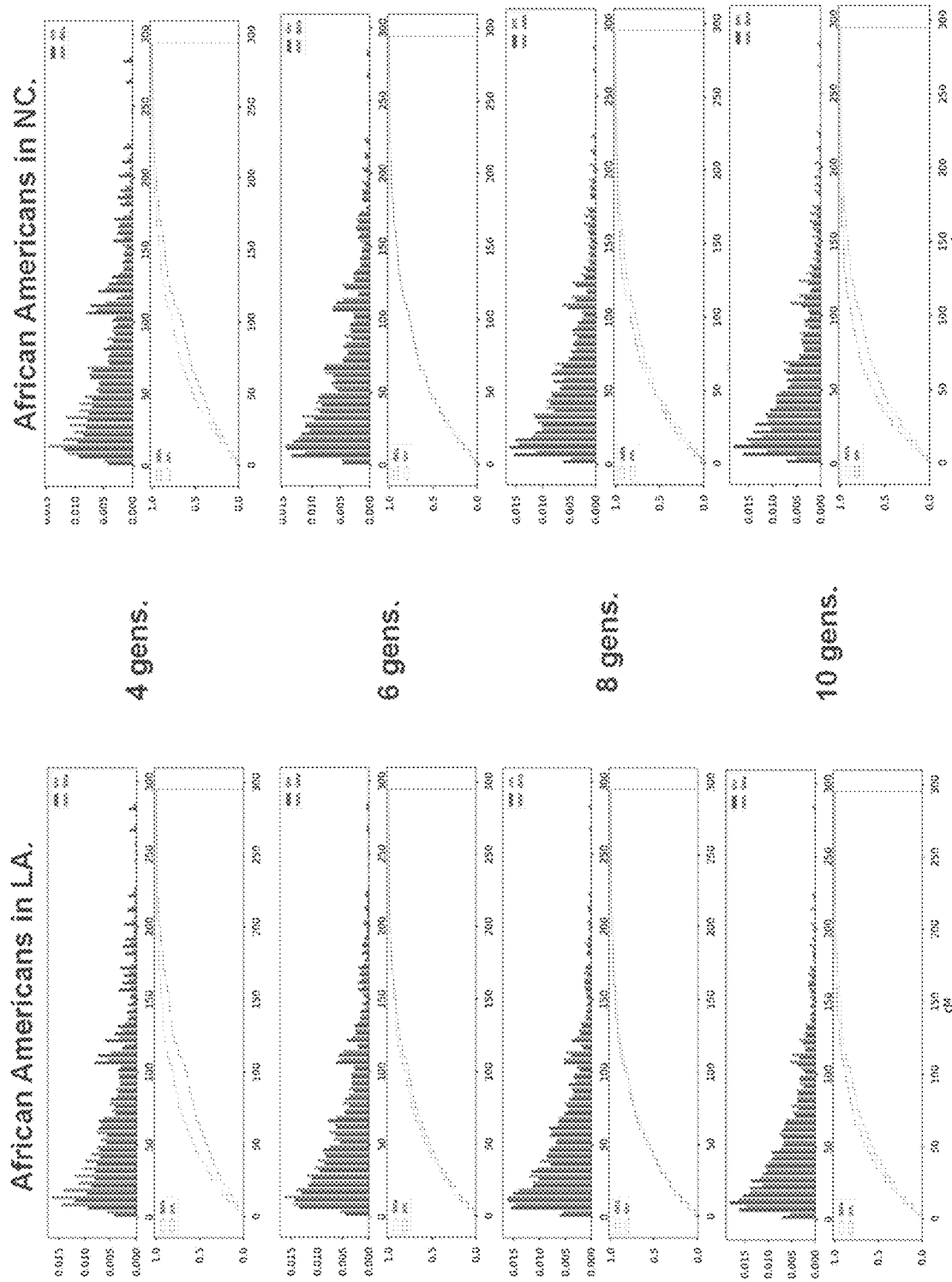
FIG. 12 are plots that compare the length distributions from real and simulated data for tracts of African origin using an embodiment described herein.

FIG. 12 are plots that compare the length distributions from real and simulated data for tracts of African origin using an embodiment described herein. In this experiment, an example inter-window HMM 400 is used for individuals belonging to African American communities. FIG. 12 is a comparison of the length distributions from real and simulated data for tracts of African origin. The result shown in FIG. 12 suggests that, under a single-pulse model, those communities likely began admixing in about 6-8 generations ago.

Admixed Reference Panel Generation

Figure 13:
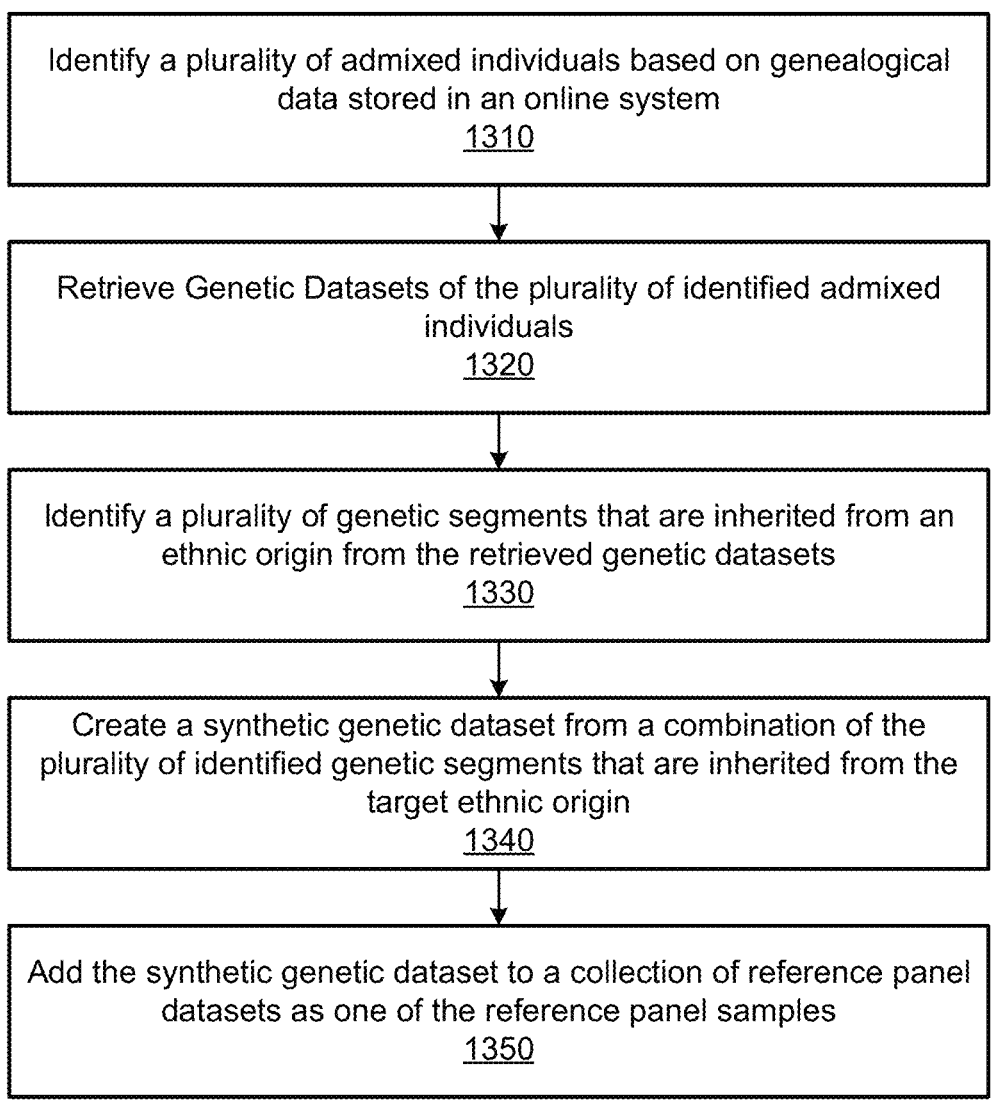
FIG. 13 is a flowchart depicting an example process of generating a synthetic genetic dataset, in accordance with an embodiment.

FIG. 13 is a flowchart depicting an example process of generating an admixed reference panel sample, which may be a synthetic genetic dataset, in accordance with an embodiment. An online system, such as the label determination system 100, may identify 1310 a plurality of admixed individuals. The identification of admixed individuals may be based on genealogical data stored in the online system. As indicated by the genealogical data, each identified admixed individual may commonly have at least one ancestor originated from a target geographical region. For example, the target geographical region may be Mexico. The identified admixed individual may each have at least one ancestor from Mexico. The genealogical data may be any suitable identification information that indicates the born location or nationality of the ancestors. For example, the genealogical data may include a pedigree of one of the identified admixed individuals with geographical location input by the individual. The genealogical data may also be census data or birth data of the ancestors. Genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

The online system may retrieve 1320 genetic datasets of the plurality of identified admixed individuals. The genetic datasets may be a genotype dataset or a haplotype dataset. The online system may also phase a genotype dataset into a pair of haplotype datasets. For an admixed individual who is identified, the genetic dataset may include a plurality of SNP sites of the admixed individual. The online system may divide the genetic dataset into a plurality of windows. Each window may correspond to a genetic locus or may include one or more SNP sites.

The online system may identify 1330 a plurality of genetic segments that are inherited from an ethnic origin from the retrieved genetic datasets. The identification of the plurality of genetic segments may include one or more sub-steps. For example, for each retrieved genetic dataset, the online system may input the genetic dataset into an HMM, such as the inter-window HMM 400, to generate labels for each of the window in the genetic dataset. While not all identified admixed individuals may have any genetic segment that is inherited from an ethnic origin, a subset of the identified admixed individuals may include some of the windows that are labeled with the ethnic origin. The online system may identify one or more genetic segments that are inherited from the ethnic origin based on the labels. For example, there might be a set of consecutive windows that are labeled with a target ethnic origin and the target geographical region. The online system may combine those windows and treated it as a genetic segment. A genetic segment may include a single window or a plurality of windows.

In one embodiment, the identification of genetic segments that belong to a target ethnic origin may include the use of the process that is described further detail in FIG. 4 through FIG. 8, including the use of one or more HMMs. For example, for each genetic dataset, the online system may generate data representing a directed acyclic graph that include a plurality of node groups. The directed acyclic graph may represent a trellis of an HMM. Each node griyo of the graph may represent a window that corresponds to a genetic segment of the identified admixed individual. Each of most of the windows (e.g., except windows representing inter-chromosome states) may be represented by a plurality of nodes. Each node may include a pair of labels that corresponds to the pair of haplotypes. Each label may represent one of the possible ethnic origins. The possible ethnic origins including the target ethnic origin and other ethnic origins. The online system may determine a path traversing the directed acyclic graph. The path may represent a statistically likely path among other possible paths in traversing the directed acyclic graph. For example, a statistically likely path may be the most probable path or a path that is more probable than 95% (or another suitable threshold) than other possible paths. A statistically likely path may also be an average of a selection of multiple probable paths. The online system may identify one or more nodes included in the path that has at least a label of the target ethnic origin. The genetic segments that correspond to the identified nodes may be identified as the genetic segments that are inherited from the target ethnic origin.

The online system may identify genetic segments inherited from the target ethnic origin from different admixed individuals. The genetic dataset of each admixed individual may contribute to a different genetic segment. For example, at least a first genetic segment identified from a first admixed individual and a second genetic segment identified from a second admixed individual may be among the identified genetic segments that are inherited from the target ethnic origin. The first and second genetic segments are different segments and may be located at different genetic loci.

The online system may create 1340 a synthetic genetic dataset from a combination of the plurality of identified genetic segments that are inherited from the target ethnic origin. The synthetic genetic dataset may be divided into a plurality of windows. Each window may be associated with a genetic sequence that is determined from the genetic data of a different admixed individual. The synthetic genetic dataset may serve as a representative of the target ethnic origin in the target geographical region. For example, the synthetic genetic data may serve as a reference panel sample for the ethnic origin Native American for the admixed population in Mexico. The online system may create a second synthetic genetic dataset that includes a second combination of genetic segments that are inherited from the same target ethnic origin (e.g., Native American), but for a second geographical region (e.g., Brazil) different from the target geographical region.

After the synthetic genetic dataset is created, the online system may add 1350 the synthetic genetic dataset to a collection of reference panel datasets as one of the reference panel samples. The collection of reference panel datasets may be used to provide possible ethnic origin labels to other genetic datasets of other individuals. The collection of reference panel datasets may include the synthetic genetic dataset and genetic datasets of unadmixed individuals. The collection of reference panel datasets may be used for the annotation process in connection with the inter-window HMM 400.

Determination of Ancestors of Admixed Individuals

Figure 14:
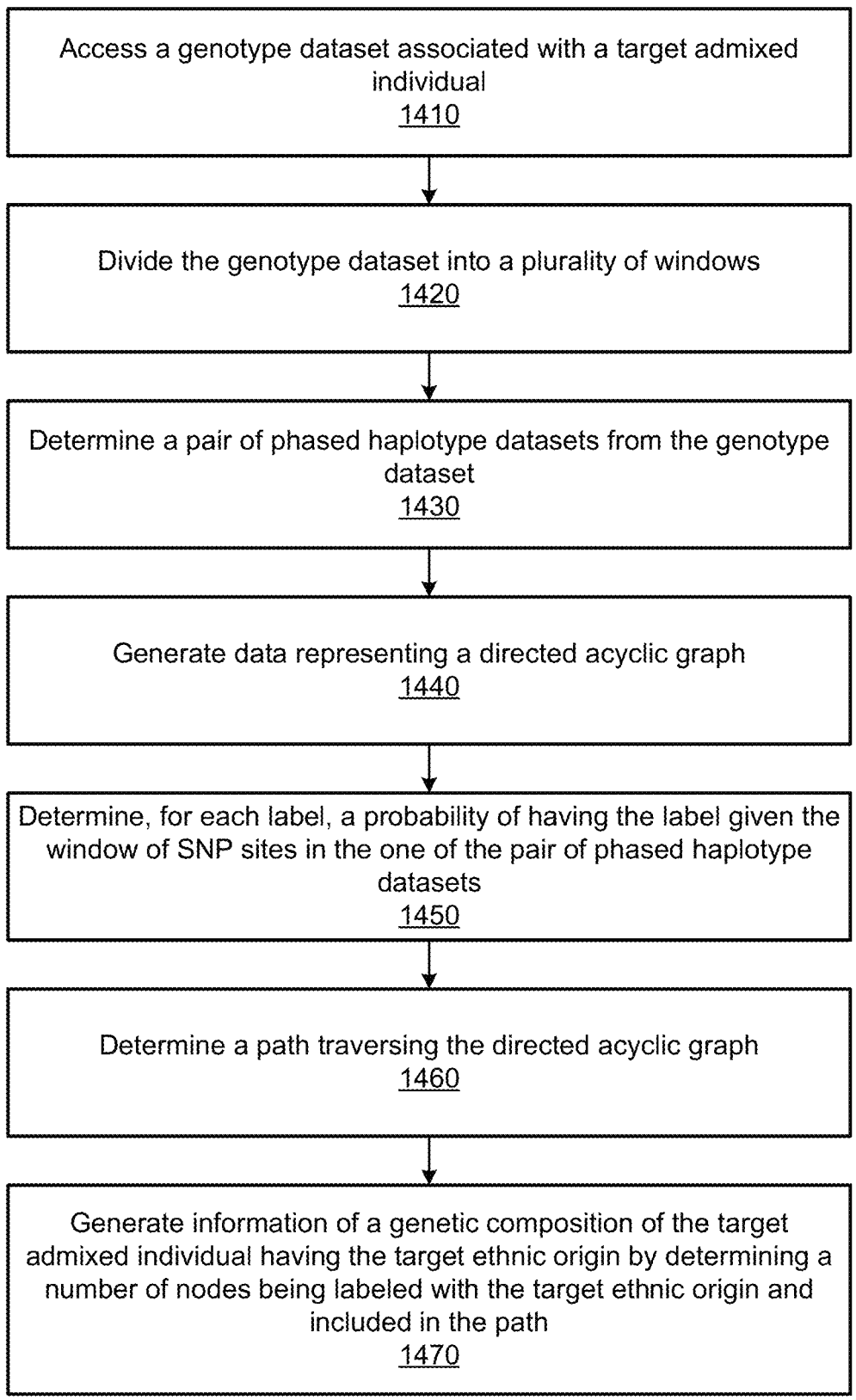
FIG. 14 is a flowchart depicting an example process of determining ethnic origin composition of an admixed individual, in accordance with an embodiment.

FIG. 14 is a flowchart depicting an example process of determining ethnic origin composition of an admixed individual, in accordance with an embodiment. The process may be similar to the process of using an inter-window HMM 400 as discussed in FIG. 4 through FIG. 8. An online system may access 1410 a genotype dataset associated with a target admixed individual. The online system may divide 1420 the genotype dataset into a plurality of windows. Each window may include a set of SNP sites. The online system may determine 1430 a pair of phased haplotype datasets from the genotype dataset. Each phased haplotype dataset may also be divided into the plurality of windows. The online system may retrieve a collection of reference panel datasets. The collection of reference panel datasets may include one or more synthetic genetic datasets, each of which corresponds to a target ethnic origin association with an admixed population from a geographical region.

The online system may generate 1440 data representing a directed acyclic graph. For example, the directed acyclic graph may represent a trellis of an inter-window HMM 400. The graph may include a plurality of node groups and a plurality of nodes. Each node may include a pair of labels representing a pair of possible ethnic origins for a first parent and a second parent. Each node may additionally include a switch label representing a switch of the order of the first parent label and the second parent label. Various labels may include different ethnic origins of the same admixed population from the same geographical region. For example, for an admixed Hispanic individual from Mexico, various labels may include Native American, European, African, etc.

The online system may determine 1450, for each label, a probability of having the label given the window of SNP sites in the one of the pair of phased haplotype datasets. The determination may be based on comparing the windows of SNP sites to the collection of reference panel datasets. The probability of labels associated with admixed ethnic origin may be assigned based on the one or more synthetic genetic datasets. The online system may determine 1460 a path traversing the directed acyclic graph. The path may represent a statistically likely path among other possible paths in traversing the directed acyclic graph. The online system may generate 1470 information of genetic composition of the target admixed individual having the target ethnic origin by determining the number of nodes being labeled with the target ethnic origin and included in the path. The genetic segments that are identified as being inherited from the target ethnic origin may be fed back to the synthetic genetic datasets to reinforce or improve the synthetic genetic datasets.

Range Determination

In an embodiment, the labeling model 190 outputs for each sample, a maximum likelihood estimate based on a reference path, such as the Viterbi path, of a directed acyclic graph such as the inter-window Hidden Markov Model (HMM) 400, together with a set of sampled estimates (e.g., 1,000 sampled estimates), each derived from a sampled path sampled from the HMM randomly or at least partially randomly based on certain criteria such as transition probabilities. The range module 145 analyzes these sampled estimates subsequently to estimate a range surrounding a reference estimate derived from the reference path. In some cases, the reference estimate may also be referred to as a Viterbi estimate. In one embodiment, the range module 145 uses the lowest and highest sampled estimates to define the lower and upper bound of the reference estimate. Experiments suggest that such approach tends to underestimate the uncertainty associated with the reference estimate. In another embodiment, the range module 145 estimates an interval surrounding the reference estimate. The range module 145 maximizes the probability that the reported range contains the true ancestry proportion (recall), while also maintaining a reasonably narrow range size.

A reference path may be any statistically likely path that traverses the directed acyclic graph (e.g., a path that is statically more likely than 95% of all possible paths traversing the directed acyclic graph). In one embodiment, the reference path is the single most likely path among all possible paths, which may also be referred to as the Viterbi path. For a directed acyclic graph, such as the trellis representing the inter-window HMM 400, the probability of any given path is determined based on the transition probability and the emission probability associated with the nodes that are traversed by the path. For example, referring to FIG. 4, a path that traverses the start state 410, the node 404, the node 406, will have an overall probability value equal to the emission probability of the node 404 multiplied by the transition probability of a transition from node 404 to node 406 multiplied by the emission probability of the node 406. As the path further extends to window 3, additional terms of transition probability and emission probability will be multiplied to the overall probability value of the path. The mostly likely path has the highest overall probability value among all possible paths. A statistically likely path has overall probability that is higher than a predetermined percentage (e.g., 95%) of all possible paths. In determining the mostly likely path, a Viterbi algorithm may be used to prune unlikely paths to reduce the amount of calculation.

In one embodiment, a path may also be sampled from the directed acyclic graph. A sampled path may also be referred to as a stochastic path. The sampling of paths may be performed based on different approaches in various embodiments. For example, A predetermined percentage threshold may be defined. Paths that have a probability value that is higher than the predetermined percentage threshold of all possible paths may be randomly selected as sampled paths. In one embodiment, let CHOOSE be an operator that chooses an argument with a probability relative to an expression so that $$\underset{x \in D}{\text{CHOOSE}} f(x)$$

returns x with probability $$\frac{f(x)}{\Sigma_{x' \in D} f(x')}.$$

The domain for p, q in $$\underset{p,q}{\text{CHOOSE}}$$

is all ordered pairs of populations (i.e., all p, q such that 1<=p<=K and 1<=q<=K for K populations). Then a stochastic path Q for a genetic sequence x is defined over a set of windows 1≤w≤W as follows. For windows that are last in a chromosome, c, $$Q_{x,C(c+1)-1} = \underset{p,q}{\text{CHOOSE}} F_x(S_{C(c+1)-1,p,q})$$

For other windows w, $$Q_{x,w} = \underset{p,q}{\text{CHOOSE}} F_x(S_{w,p,q}) \times P_x(S_{w,p,q} \to S_{w+1,Q_{x,w+1}}) \times E_{x,w+1}(Q_{x,w+1})$$

In these equations, $F_x(S)$ denotes the forward probability, i.e., the sum of probability of all paths through the HMM that start in the start state and end in state S (including the emission of state S); $S_{w,p,q}$ denotes the state of window w, where p, q is the two ethnicity assignment at window w; $S_{C(c+1)-1,p,q}$ denotes the last state in a chromosome c; $P_X(S)$ denotes the transition probability, and $E_{x,w+1}(S)$ is the emission probability at window w+1.

The range module 145 uses the mean and standard deviation of the set of sampled estimates (e.g., 1,000 sampled estimates) to calculate an interval surrounding the reference estimate. The approach also accounts for the reference estimate, and the population for which range is calculated. Accordingly, the range module 145 obtains the lower and upper bounds of the interval by linearly scaling the standard deviation of the sampled estimates (e.g., 1,000 sampled estimates) with factors that are specific to both population and Viterbi value (lower and upper bound factors can be different to reflect upward or downward bias of the estimate).

The range module 145 takes the set of sampled estimates, referred to as P, and computes the standard deviation, S, and mean, M, of P using equation (1).

$$S=sd(P); M=\text{mean}(P) \quad (1)$$

The range module 145 also identifies the scaling factors and $\lambda_1$ and $\lambda_2$ for the upper and lower bounds of the range respectively. The range module 145 determines the reported confidence interval as $[M-S*\lambda_1, M+S*\lambda_2]$, where, $\lambda_1$ and $\lambda_2$ are specific for population, and to the bin that the reference estimate falls into. In the event that the Viterbi estimate falls outside of this confidence interval, the interval may be adjusted to include the Viterbi estimate as the upper or lower bound.

The values for λ1 and λ2 are determined using a set of simulated individuals with known ethnicity proportions. Training for the values of λ1 and λ2 is done by performing an exhaustive joint search over a 2-dimensional grid in 0.5 increments of λ1 and λ2 and finding the combination of values that maximizes the following statistic F as determined by equation (2).

$$F=\text{recall}-K*(S*\lambda_1+S*\lambda_2) \quad (2)$$

In equation (2), K is a value that adjusts the importance placed on reporting a narrow range (higher K increases the emphasis on narrower range). Different values of K can be used to adjust the trade off between higher recall and narrower range size. Performance of this approach may be evaluated by measuring recall with the optimized lambda values on an independent set of simulated admixed individuals In one embodiment, the label determination system 100 may transmit the determination results to the end user for display at a graphical user interface. The percentage reported to a user may be the most likely percentage within a range of percentages. For example, the label determination system 100 might report an end user as 40% England and Wales with a confidence range of 30-60%. This can be interpreted by the end user that he/she is most likely 40% England and Wales but that he/she could be anywhere between 30 and 60% England and Wales.

The label determination system 100 runs a reference estimate on a user's DNA sample (e.g., a genome wide estimate) and reports that back as the user's most likely ethnicity estimate. The range is based on a set of randomly sampled paths (e.g., 1000 sampled paths). For example, if a window has an 80% chance of being from England and Wales, then it has a 20% chance of being from some other region. The confidence interval captures these sorts of lower chances across a user's DNA.

The label determination system 100 uses a set of sampled estimates, to estimate the confidence interval surrounding the reference estimate that is reported to the user. The system maximizes the probability that the reported range contains the true ancestry proportion (recall), while also maximizing precision by maintaining a fairly narrow range.

The label determination system 100 takes the mean and standard deviation of the 1000 sampled estimates and uses this to calculate a confidence range surrounding the reference estimate. When calculating this range, the label determination system 100 takes into account the value of the Viterbi estimate, and the population for which the range is calculated.

In an embodiment, the process is tested using the same synthetic admixed individuals used for the cross validation studies to determine how often it correctly gets the known ethnicity percentage within the range. In other words, how often does the range overlap the known ethnicity. The process performs very well for some populations and less well for others. Since the true ethnicity is known, the system incorporates correction factors specific for each population to maximize the probability that the true ethnicity falls within the confidence level.

Confidence Module

Confidence, in this context, may be referred to the likelihood an individual truly inherits DNA from ancestor(s) of a certain population. In an embodiment, the confidence module 155 implements a machine learning approach, such as a random forest approach, to assign a confidence level, categorized as a set of predetermined levels (e.g., low, medium or high) for each estimated population.

In one embodiment, the machine learning model may be a random forest model. The random forest model comprises a list of binary classifiers, with each classifier taking a subset of input features and voting between binary values, for example, 1 indicating "yes, this individual inherits DNA from this population" and 0 indicating "no, this individual does not inherit DNA from this population". Features used by these classifiers include quantiles calculated from the set of sampled estimates and the reference estimate passing from the labeling model 190.

Feature vector F is defined by equation (3).

$$F = [\text{Viterbi estimate}, 5\%, 10\%, 15\%, \ldots, 95\% \text{ quantile of the set of samples estimates}] \quad (3)$$

The binary classifiers are trained using a set of simulated individuals with known ancestry proportions. Training for classifiers is done using a random forest algorithm. In an embodiment, a random forest model is trained separately for each population.

For each estimated population, the percentage of binary classifications supporting ancestry from that population is convert into a score between 0 and 1. A set of simulated data with known ancestry proportions is used as validation set to calibrate between Random Forest score and the confidence. As an example, random forest score thresholds for assigning low, medium, high confidence are selected using the following rules in table I below.

TABLE I

Categories of confidence classification and the corresponding validation set confidence

| Confidence level | Random Forest score threshold |
| --- | --- |
| High | 95% confidence on the validation set |
| Medium | 60-95% confidence on the validation set |
| Low | Below 60% confidence on the validation set |

Figure 15A:
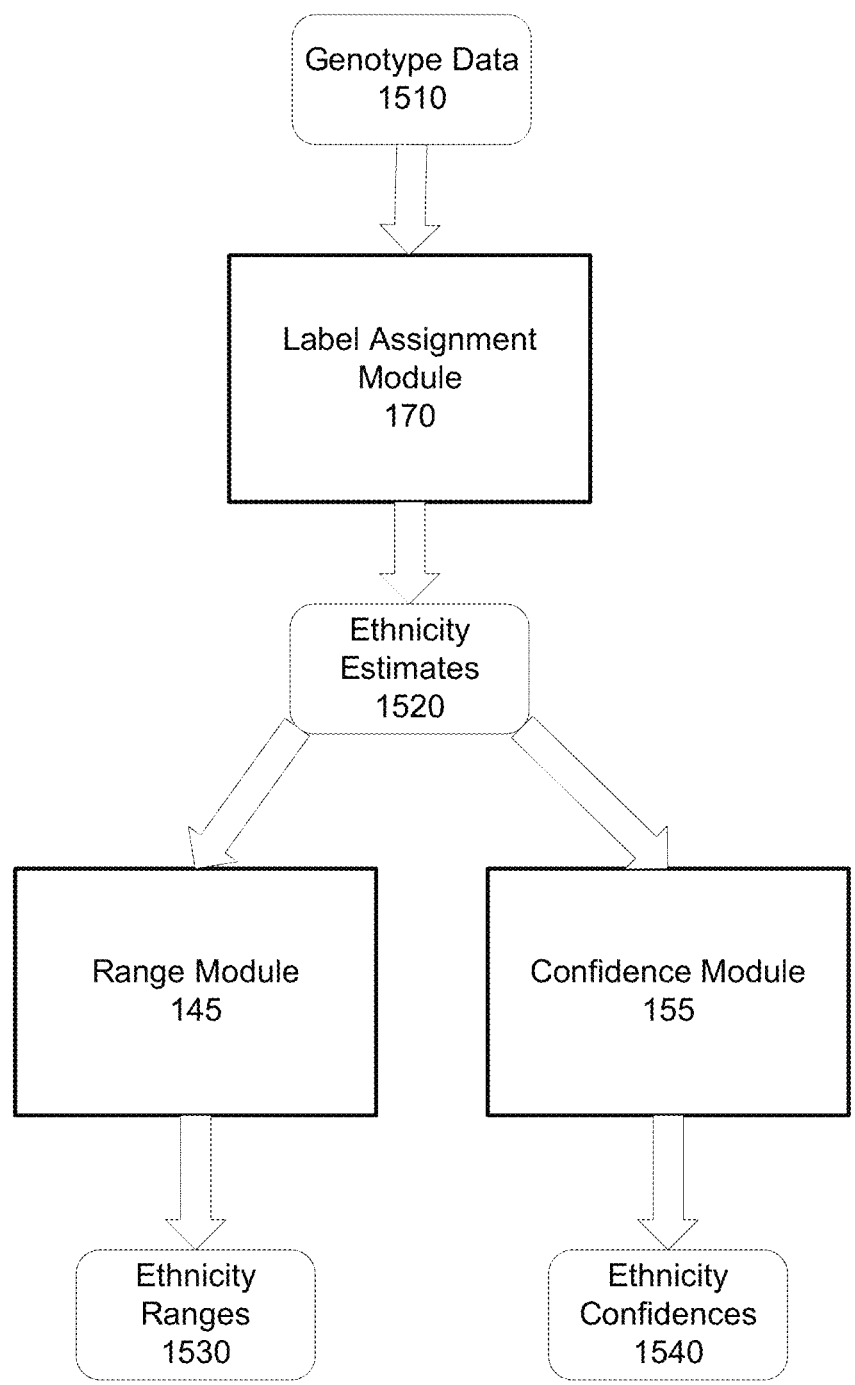
FIG. 15A is the overall process of generating ethnicity ranges and ethnicity confidences, in accordance with an embodiment.

FIG. 15A shows the overall process of generating ethnicity ranges and ethnicity confidences, in accordance with an embodiment. As shown in FIG. 15A, the labeling model 190 receives genotype data 1510 as input and generates ethnicity estimates 1520. The range module 145 receives the ethnicity estimates 1520 generated by the labeling model 190 and generates ethnicity ranges 1530 based on the ethnicity estimates 1520. The confidence module 155 receives the ethnicity estimates 1520 generated by the labeling model 190 and generates ethnicity confidences 1540 based on the ethnicity estimates 1520.

Polygon Module

Figure 15B:
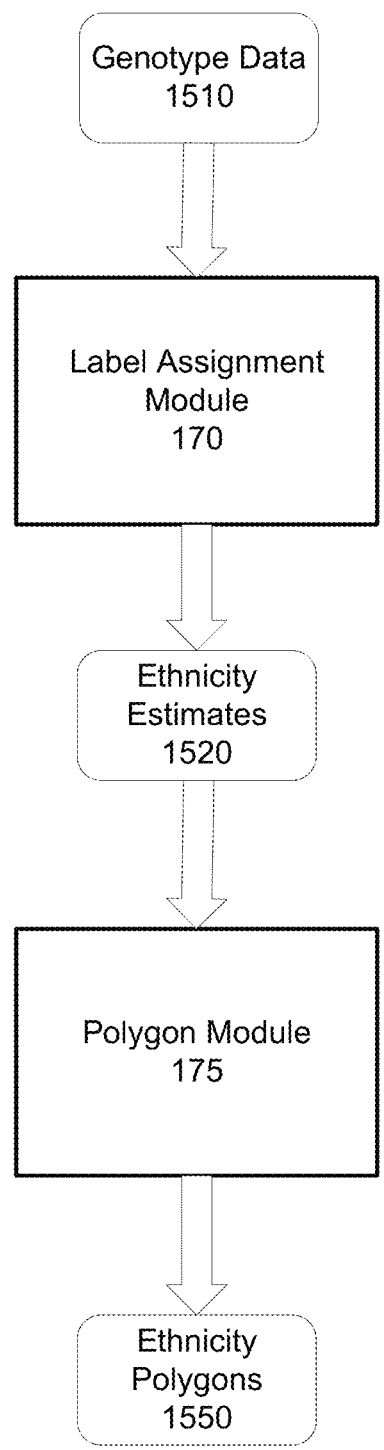
FIG. 15B is the overall process of generating ethnicity polygons, in accordance with an embodiment.

The polygon module 175 creates ethnicity polygons for displaying via a user interface. FIG. 15B shows the overall process of generating ethnicity polygons, in accordance with an embodiment Similar to the process shown in FIG. 15A, the labeling model 190 receives genotype data 1510 as input and generates ethnicity estimates 1520. The polygon module 175 receives the ethnicity estimates 1520 generated by the labeling model 190 and generates ethnicity polygons 1550 based on the ethnicity estimates 1520.

Figure 16:
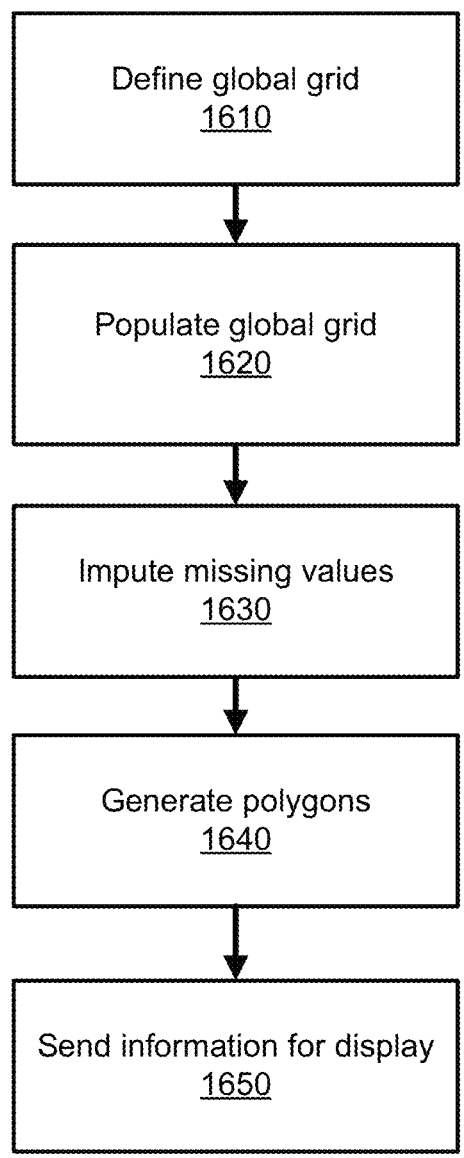
FIG. 16 shows the detailed process of generating ethnicity polygons, in accordance with an embodiment.

FIG. 16 shows the detailed process of generating ethnicity polygons, in accordance with an embodiment.

The polygon module 175 defines 1610 a global grid by dividing a representation of a geographical area such as the world into grids. In an embodiment, polygon module 175 divides the representation of the geographical area into two grids: one with each square one degree (latitude and longitude) per side and one with half-degree sides. The polygon module 175 repeats the following steps independently for both the one- and half-degree grids. The choice between one- and half-degree grid depends on the availability of data with finer scale geographic resolution. The polygon module 175 identifies grids overlapping with land by checking the center of the grid square as well as the 4 vertices and 4 edge midpoints. If any of the 9 points overlap with land, the grid square is flagged as containing land. The polygon module 175 assigns a country to the grid square if that country is covered by a majority of the 9 points.

The polygon module 175 populates 1620 the global grid using the following steps. For each grid square, the polygon module 175 calculates a sum of fractional assignments for each population by summing the contributions from all individuals in a training set that have ancestors from a location within the grid square. In one embodiment, the training set includes a mixture of the reference panel and customers with trees from a single country.

The polygon module 175 identifies grid squares that were not previously flagged as land that have assignments and subsequently flags them as being land to account for squares overlapping small islands and complicated coastlines.

The polygon module 175 determines contributions of an individual's ethnicity estimates to a grid square in several ways.

(i) For users, the polygon module 175 uses people where the terminal nodes in their family trees were born in the same country. The polygon module 175 then focuses on the grid squares containing the birth locations for each of the terminal nodes in their tree. The polygon module 175 calculates the fraction of their ethnicity estimate associated with each grid square with the following formula: (proportion of ancestry from the tree for the square) X (proportion of the ethnicity estimate for the ethnicity region).

(ii) For countries for which the label determination system 100 does not have enough samples to adequately cover most of the country, the polygon module 175 distributes evenly, a person's ethnicity estimate assignments across all of the grid squares overlapping that country in a process referred to as country filling.

(iii) For countries for which the label determination system 100 does not have many users with tree data, the polygon module 175 performs country filling using users who were born in that country.

(iv) For customers in the reference panel, the polygon module 175 performs steps i, ii, or iii, but using their ethnicity estimates from the cross validation process.

(v) For third party datasets, the polygon module 175 assigns a person's ethnicity estimates to a grid square when latitude and longitude information is present.

(vi) For third party datasets where latitude and longitude information is not present, the polygon module 175 either performs country filling, or for some populations, fills a predefined regional polygon representing the location of the given population instead of the entire country.

For each grid square, the polygon module 175 calculates a percentage for each ethnicity region by dividing the sum of fractional ethnicity assignments for that ethnicity region by the total of all sums for that grid square. This percentage represents that average amount of assignment for that ethnicity region for the given grid square.

The polygon module 175 imputes 1630 missing values as follows. The polygon module 175 imputes missing for grid squares for each ethnicity region that is present in nearby squares. The polygon module 175 performs imputation only for squares that are not from countries that are country filled, overlap land, of the 8 adjacent squares one step away 3 or more have a nonzero value, or of the 24 squares two steps away 5 or more have a nonzero value. Additionally, at least one of the 4 squares sharing an edge with the imputed square must have a nonzero value.

The polygon module 175 calculates the imputed value using inverse distance weighting with p=4. Inverse distance weighting (IDW) is a type of deterministic method for multivariate interpolation with a known scattered set of points. The assigned values to unknown points are calculated with a weighted average of the values available at the known points. A general form of finding an interpolated value u at a given point x based on samples $u_i=u(x_i)$, for i=1, 2, ..., N using IDW is an interpolating function, for example, $$u(x) = \begin{cases} \dfrac{\sum_{i=1}^{N} w_i(x) u_i}{\sum_{i=1}^{N} w_i(x)}, & \text{if } d(x, x_i) \neq 0 \text{ for all } i, \\ u_i, & \text{if } d(x, x_i) = 0 \text{ for some } i, \end{cases}$$

where $$w_i(x) = \dfrac{1}{d(x, x_i)^p}$$

In this equation x denotes an interpolated (arbitrary) point, $x_i$ is an interpolating (known) point, d is a given distance (metric operator) from the known point $x_i$ to the unknown point x, N is the total number of known points used in interpolation and p is a positive real number, called the power parameter. Here weight decreases as distance increases from the interpolated points. Greater values of p assign greater influence to values closest to the interpolated point, with the result turning into a mosaic of tiles (a Voronoi diagram) with nearly constant interpolated value for large values of p.

The imputation method is also applied to squares with nonzero percentages to help smear or even out the assignments. After imputation, the polygon module 175 renormalizes the percentages for each grid square to ensure the sum of percentages equals 100% for each grid square.

In an embodiment, the polygon module 175 performs smearing of grid values similar to the imputation step, except for the following differences: (1) Only the 8 adjacent squares are used, and only 2 adjacent squares need nonzero values; (2) p=2 for inverse distance weighting.

The polygon module 175 generates 1640 polygons separately for each ethnicity region. In an embodiment, the polygon module 175 creates polygons using weighted kernel density polygons using two-dimensional kernel density estimation, for example, using the kde2d.weighted ( ) function from the ggtern library in R. They represent the geographic regions where assignments to an EV region are strongest but do not contain information on what the assignments are.

In another embodiment, the polygon module 175 generates splined, grid-based polygons. The grid based polygons are directly based on the grid values and represent regions where the average assignment for an ethnicity region falls within a specific range: 0.5-5%, 5-25%, 25-50%, 50-75%, 75-95%, 95-100%. Separate polygons are created for each of these ranges. The polygon module 175 defines initial polygons by simply tracing the borders of the contiguous grid squares that fall within the given range. The polygon module 175 applies a splining step, so polygon edges are smoother and not blocky. The polygon module 175 performs splining independently for each polygon edge that is not a coastline and is, therefore, comprised of straight lines meeting at right angles using a smoothing function, for example, using the smooth.spline( ) function in R with the smoothing parameter equal to lambda.

The polygon module 175 sends 1650 information describing the resulting polygons for a given ethnicity region for display on a map using a user interface with a separate color used to represent each range.

Figure 17:
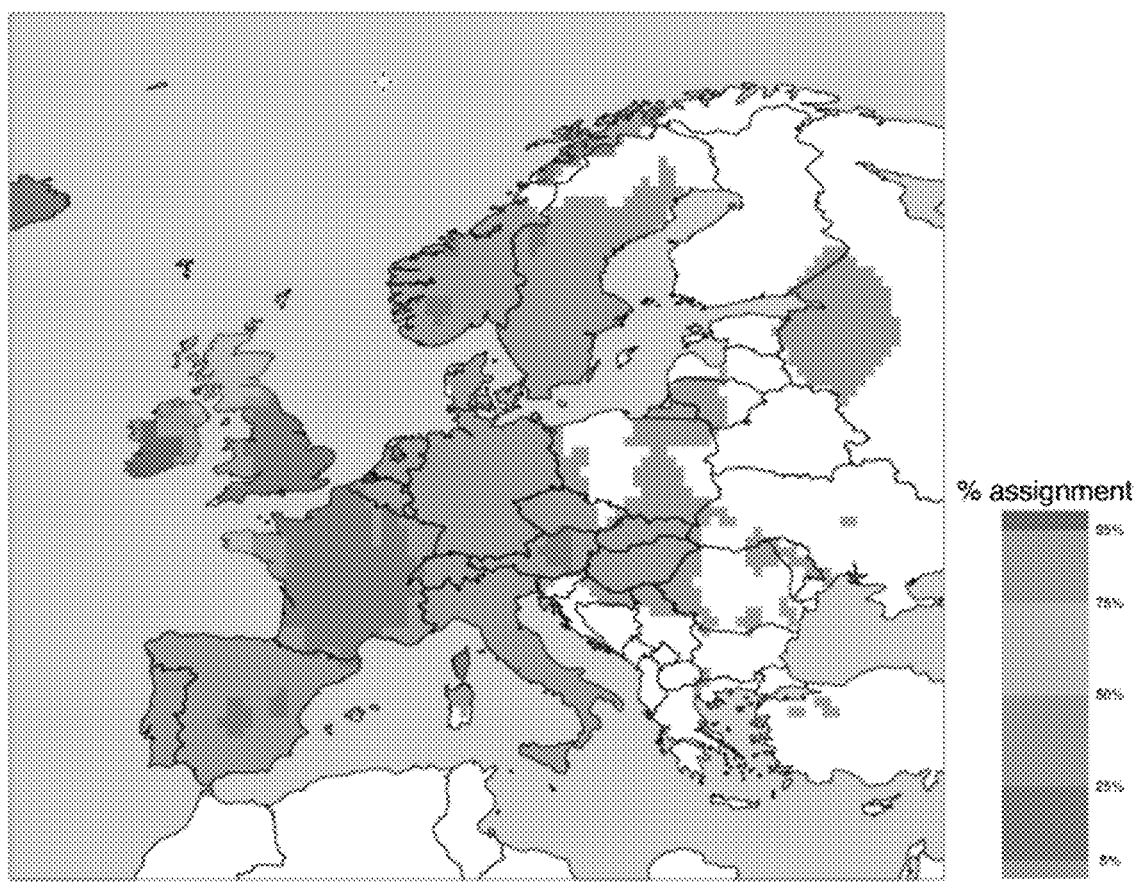
FIG. 17 shows a screenshot of a user interface showing map of estimates for an example country (Ireland & Scotland), in accordance with an embodiment.

FIG. 17 shows a screenshot of a user interface showing map of estimates for an example country (Ireland & Scotland), in accordance with an embodiment. High estimates outside of Ireland in Scotland, Wales, and Brittany likely reflect historic migrations of Celtic people. The label determination system 100 uses maps similar to that shown in FIG. 17 to show ethnicity estimates geographically. The geographic distribution of ethnicity estimates within a country help make sense of results. For example, as shown in FIG. 17, there is a high level of Ireland & Scotland ancestry in the Brittany region of France. This makes sense as the Ireland & Scotland assignment is the result of the Celtic peoples who lived there and the Celtic peoples migrated to the Brittany area of France. The Celtic language Breton is traditionally spoken there. Higher Ireland & Scotland estimates in Wales also likely reflect the history of Celtic migration in the region.

Because label determination system 100 uses 43 populations in the reference panel, the label determination system 100 divides the globe into 43 overlapping geographic regions/groups. Each region represents a population with a unique genetic profile. Where possible, the label determination system 100 uses the known geographic locations of the samples to guide where the regional boundaries should be.

Figure 18A:
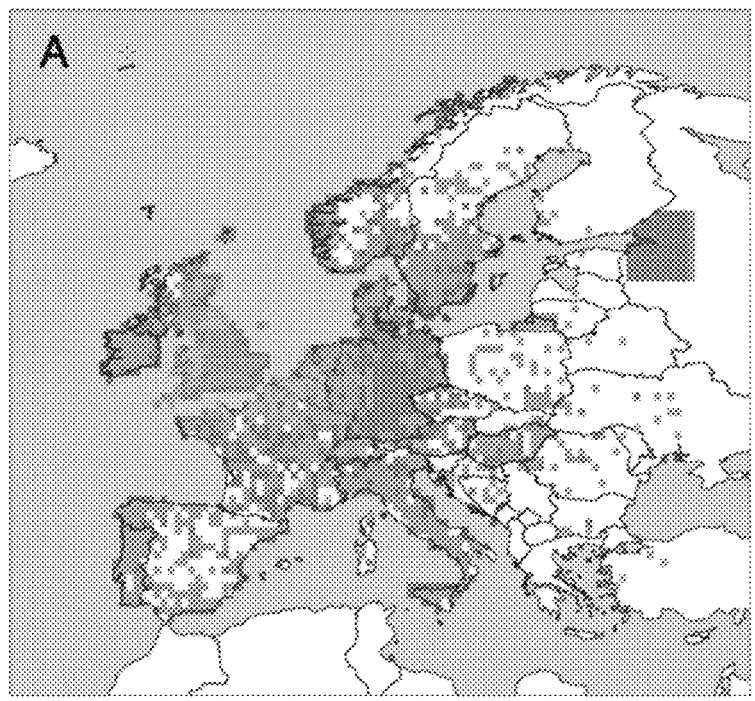
FIGS. 18A-C show screenshots of a user interface showing regional polygons using geographical sample locations, in accordance with an embodiment.
Figure 18B:
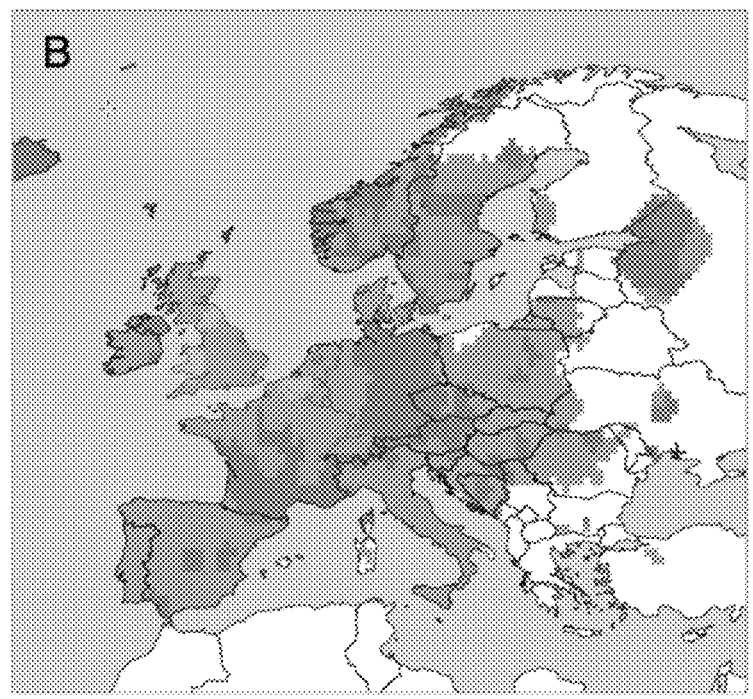
Figure 18C:
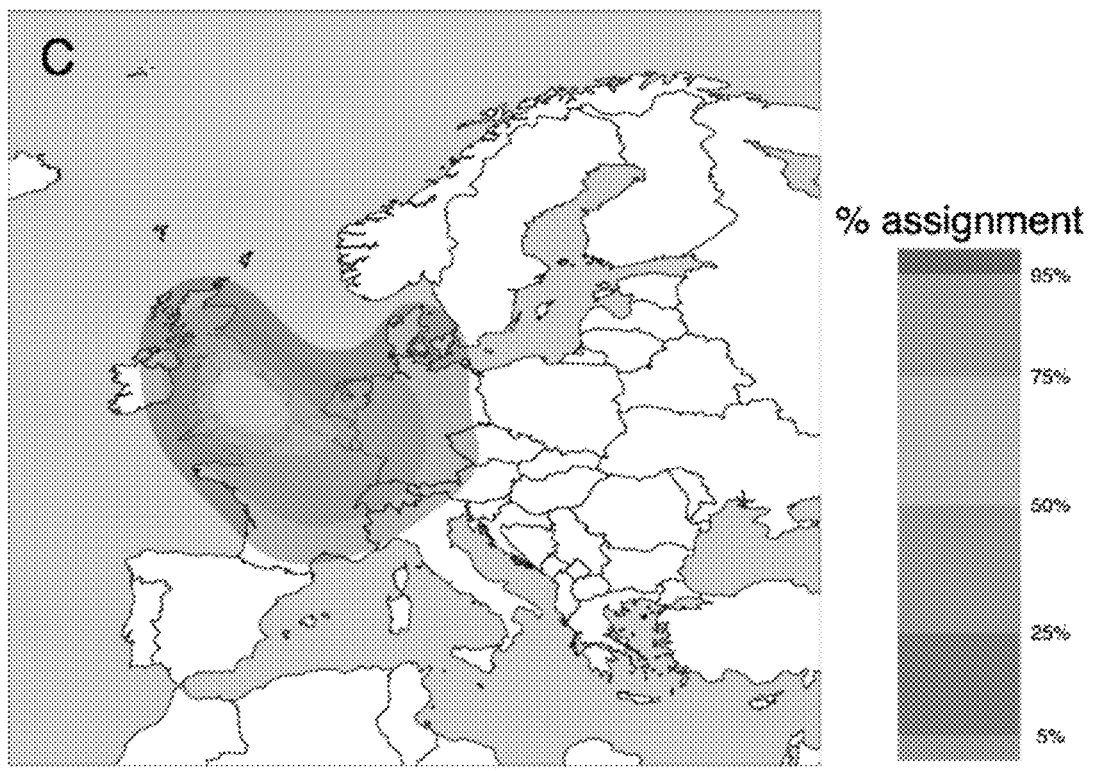

FIGS. 18A-C show screenshots of a user interface showing regional polygons using geographical sample locations, in accordance with an embodiment. FIG. 18A shows the distribution of the England & Wales ethnicity predicted for a set of samples with geographic information. Samples are assigned to grids of 0.5 degrees longitude by 0.5 degrees latitude based on the average birth location of their ancestors' grandparents. The color of each grid square point on the map represents the average England and Wales ethnicity of samples from each grid. FIG. 18B shows the maps after filling in missing regions and smoothing the results. Accordingly, FIG. 18B shows the results after imputing values to fill in gaps and applying smoothing methods to make the plot less 'spotty'. The information is processed with kernel smoothing to create the outlines representing the ancestry regions shown to users, as shown in FIG. 18C.

As illustrated by the plot shown in FIG. 18C, there is a gradient of ethnicity in this region that is centered in England that quickly tapers off in surrounding regions. For example, the next level of concentration, is in areas surrounding England such as Wales, France, and Belgium. The ethnicity gradient continues to diminish as represented in purple with the borders reaching as far away as Italy, Switzerland, Sweden, and Ireland. Where possible, this information is applied directly to the drawing of regional boundaries (FIG. 18C) that appear on the maps presented by the label determination system 100.

These polygons appear as nested regions with increasing depth of shading. The regions with the highest average assignments are the most likely physical locations of a given user's ancestors. The regions with lower average levels represent other possible locations of origin that are less likely. Each polygon is accompanied by a detailed account of the history of the region.

Computing Machine Architecture

Figure 19:
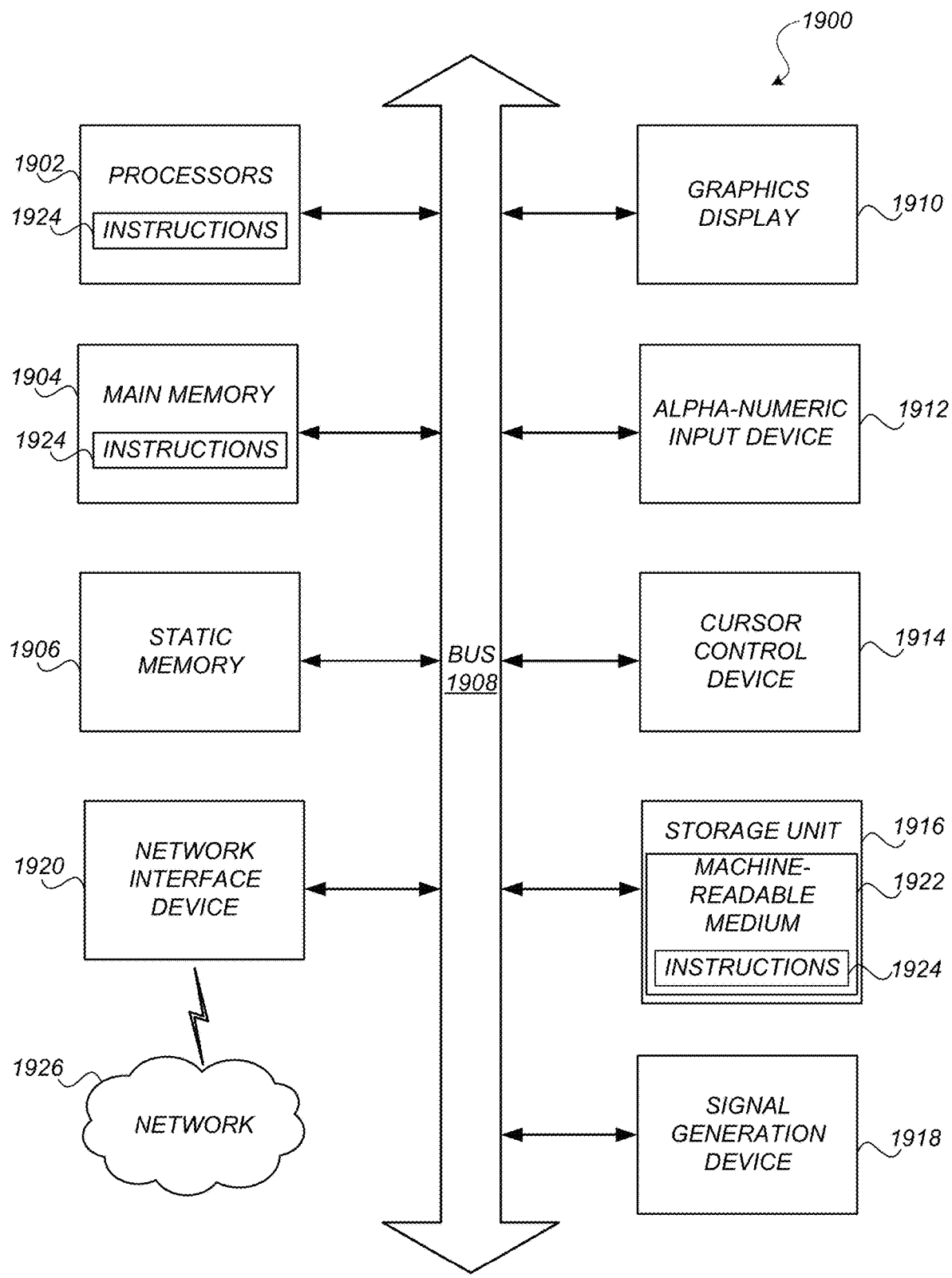
FIG. 19 is a block diagram illustrating an example computer architecture, in accordance with an embodiment.

FIG. 19 is a block diagram illustrating components of an example computing machine that is capable of reading instructions from a computer-readable medium and execute them in a processor (or controller). A computer described herein may include a single computing machine shown in FIG. 19, a virtual machine, a distributed computing system that includes multiples nodes of computing machines shown in FIG. 19, or any other suitable arrangement of computing devices.

By way of example, FIG. 19 shows a diagrammatic representation of a computing machine in the example form of a computer system 1900 within which instructions 1924 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 19 may correspond to any software, hardware, or combined components shown in FIG. 1A, including but not limited to, the label determination system 100, various computing devices engines, interfaces, terminals, and machines. While FIG. 19 shows various hardware and software elements, each of the components described herein may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1924 that specify actions to be taken by that machine. Further, while only a single machine is illustrated, the term "machine" and "computer" may also be taken to include any collection of machines that individually or jointly execute instructions 1924 to perform any one or more of the methodologies discussed herein.

The example computer system 1900 includes one or more processors 1902 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1900 may also include a memory 1904 that store computer code including instructions 1924 that may cause the processors 1902 to perform certain actions when the instructions are executed, directly or indirectly by the processors 1902. Instructions can be any directions, commands, or orders that may be stored in different forms, such as equipment-readable instructions, programming instructions including source code, and other communication signals and orders. Instructions may be used in a general sense and are not limited to machine-readable codes.

One and more methods described herein improve the operation speed of the processors 1902 and reduces the space required for the memory 1904. For example, the machine learning methods described herein reduces the complexity of the computation of the processors 1902 by applying one or more novel techniques that simplify the steps in training, reaching convergence, and generating results of the processors 1902. The algorithms described herein also reduces the size of the models and datasets to reduce the storage space requirement for memory 1904.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1900 may include a main memory 1904, and a static memory 1906, which are configured to communicate with each other via a bus 1908. The computer system 1900 may further include a graphics display unit 1910 (e.g., a plasma display panel (PDP), a liquid crystal display (LCD), a projector, or a cathode ray tube (CRT)). The graphics display unit 1910, controlled by the processors 1902, displays a graphical user interface (GUI) to display one or more results and data generated by the processes described herein. The computer system 1900 may also include alphanumeric input device 1912 (e.g., a keyboard), a cursor control device 1914 (e.g., a mouse, a trackball, a joystick, a motion sensor, or other pointing instrument), a storage unit 1916 (a hard drive, a solid state drive, a hybrid drive, a memory disk, etc.), a signal generation device 1918 (e.g., a speaker), and a network interface device 1920, which also are configured to communicate via the bus 1908.

The storage unit 1916 includes a computer-readable medium 1922 on which is stored instructions 1924 embodying any one or more of the methodologies or functions described herein. The instructions 1924 may also reside, completely or at least partially, within the main memory 1904 or within the processor 1902 (e.g., within a processor's cache memory) during execution thereof by the computer system 1900, the main memory 1904 and the processor 1902 also constituting computer-readable media. The instructions 1924 may be transmitted or received over a network 1926 via the network interface device 1920.

While computer-readable medium 1922 is shown in an example embodiment to be a single medium, the term "computer-readable medium" should be taken to include a single medium or multiple media (e.g., a centralized or distributed database, or associated caches and servers) able to store instructions (e.g., instructions 1924). The computer-readable medium may include any medium that is capable of storing instructions (e.g., instructions 1924) for execution by the processors (e.g., processors 1902) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The embodiments described herein create reference samples from extracted segments of ethnicity from admixed samples. This can be used to enhance admixed reference panel. The embodiments described herein can also be used to further break down ethnicity regions to identify potential new sub-regions, or refined ancestry estimation. For example, new regions can be made for certain admixed reference panel. The embodiments described herein can also perform admixture mapping to discover ethnicities that correlate with traits in admixed individuals and to study the time of admixture events. For example, the length of ethnicity segments can provide insight on when the admixture happened.

The label determination system 100 comprises one or more processors and one or more non-transitory computer readable storage mediums. The one or more processors may implement the functions attributed above to modules. The modules may be hardware modules (i.e., computer hardware specially configured to perform specific functions), software modules, or some combination thereof. The non-transitory computer readable mediums may store computer instructions that, when executed, perform the methods described herein. In some embodiments, the label determination system 100 is a single computing system. In alternate embodiments, the label determination system 100 may be a distributed system including spatially-separated databases and computing systems (e.g., servers) that communicate via a network.

The label determination system 100 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1A. In some embodiments, a distributed computing architecture is used to implement the described features. One example of such a distributed computing platform is the Apache Hadoop project available from the Apache Software Foundation.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

We claim:

1. A computer implemented method comprising:
   accessing a genotype dataset associated with an individual;
   dividing the genotype dataset into a plurality of windows, each window comprising a set of a plurality of single nucleotide polymorphisms (SNPs);
   determining a pair of phased haplotype datasets from the plurality of windows of genotype dataset;
   generating, using one or more processors and the pair of phased haplotype datasets, an inter-window hidden Markov model (HMM) that comprises:
      (i) a plurality of node groups, each node group representing one of the windows that comprises a set of SNPs, each node group comprising a plurality of nodes, each node representing a state of the window represented by the node group, the state comprising:
         (1) a first parent label, and
         (2) a second parent label, and
      (ii) a plurality of edges, at least one edge connecting a first node to a second node and representing a transition from the first node to the second node,
      and wherein the inter-window HMM is trained by:
         receiving phased haplotype datasets corresponding to sequences of alleles of individuals;
         building per-window models for the plurality of windows;
         receiving a set of reference panel samples; and
         training the per-window models using the set of reference panel samples to generate an emission probability for each node of each window in the inter-window HMI; and
   generating information on the individual using the inter-window HMM.

2. The computer implemented method of claim 1, wherein the information on the individual comprises one or more of: a set of possible ethnic origins of the individual and percentage compositions of the set of the possible ethnic origins, a set of possible paternal origins and percentage compositions of the set of possible paternal origins, or a set of possible maternal origins and percentage compositions of the set of possible maternal origins.

3. The computer implemented method of claim 1, wherein the information on the individual comprises one or more of: a visualization of the individual's ancestry composition by chromosome painting, information about a particular trait of the individual, a percentage of DNA shared with a relative of the individual, a set of similarities and differences in a first genotype dataset of a first parent of the individual and a second genotype dataset of a second parent of the individual, or information on individuals genetically related to the individual.

4. The computer implemented method of claim 1, wherein the plurality of nodes in each node group represents permutations of different first parent labels and second parent labels.

5. The computer implemented method of claim 1, wherein a switching of order of the first parent label and the second parent label corresponds to a switching of the first and second parent labels from one node group to a next node group.

6. The computer implemented method of claim 1, wherein generating the inter-window HMM further comprises:
   initiating label probabilities, each label probability for a particular label representing a probability distribution of the particular label among other possible labels;
   initiating label change probabilities, each label change probability representing a likelihood of a change of label from one window to another window;
   initiating a label switch probability representing a likelihood of a switching of order of the first parent label and the second parent label from one window to another window;
   adjusting the label probabilities, label change probabilities, and the label switch probability through iterations;
   determining transition probabilities based on the label probabilities, the label change probabilities, and the label switch probability, each transition probability associated with a particular edge and representing a likelihood of the first node connected by the particular edge from one node group transitioning to the second node connected by the particular edge from another node group; and
   connecting the nodes with edges, each edge corresponding to a determined transition probability.

7. The computer implemented method of claim 1, wherein each node is associated with the emission probability based on the pair of phased haplotype datasets.

8. A non-transitory computer-readable storage medium storing executable computer program instructions, the computer program instructions, when executed by one or more processors, cause the one or more processors to perform steps comprising:
   accessing a genotype dataset associated with an individual;
   dividing the genotype dataset into a plurality of windows, each window comprising a set of a plurality of single nucleotide polymorphisms (SNPs);
   determining a pair of phased haplotype datasets from the plurality of windows of genotype dataset;
   generating, using one or more processors and the pair of phased haplotype datasets, an inter-window hidden Markov model (HMM) that comprises:
      (i) a plurality of node groups, each node group representing one of the windows that comprises a set of SNPs, each node group comprising a plurality of nodes, each node representing a state of the window represented by the node group, the state comprising:
         (1) a first parent label, and
         (2) a second parent label, and
      (ii) a plurality of edges, at least one edge connecting a first node to a second node and representing a transition from the first node to the second node,
      and wherein the inter-window HMI is trained by:
         receiving phased haplotype datasets corresponding to sequences of alleles of individuals;
         building per-window models for the plurality of windows;
         receiving a set of reference panel samples; and
         training the per-window models using the set of reference panel samples to generate an emission probability for each node of each window in the inter-window HMM; and
   generating information on the individual using the inter-window HMM.

9. The non-transitory computer-readable storage medium of claim 8, wherein the information on the individual comprises one or more of: a set of possible ethnic origins of the individual and percentage compositions of the set of the possible ethnic origins, a set of possible paternal origins and percentage compositions of the set of possible paternal origins, or a set of possible maternal origins and percentage compositions of the set of possible maternal origins.

10. The non-transitory computer-readable storage medium of claim 8, wherein the information on the individual comprises one or more of: a visualization of the individual's ancestry composition by chromosome painting, information about a particular trait of the individual, a percentage of DNA shared with a relative of the individual, a set of similarities and differences in a first genotype dataset of a first parent of the individual and a second genotype dataset of a second parent of the individual, or information on individuals genetically related to the individual.

11. The non-transitory computer-readable storage medium of claim 8, wherein the plurality of nodes in each node group represents permutations of different first parent labels and second parent labels.

12. The non-transitory computer-readable storage medium of claim 8, wherein a switching of order of the first parent label and the second parent label corresponds to a switching of the first and second parent labels from one node group to a next node group.

13. The non-transitory computer-readable storage medium of claim 8, wherein generating the inter-window HMM further comprises:
   initiating label probabilities, each label probability for a particular label representing a probability distribution of the particular label among other possible labels;
   initiating label change probabilities, each label change probability representing a likelihood of a change of label from one window to another window;
   initiating a label switch probability representing a likelihood of a switching of order of the first parent label and the second parent label from one window to another window;
   adjusting the label probabilities, label change probabilities, and the label switch probability through iterations;
   determining transition probabilities based on the label probabilities, the label change probabilities, and the label switch probability, each transition probability associated with a particular edge and representing a likelihood of the first node connected by the particular edge from one node group transitioning to the second node connected by the particular edge from another node group; and
   connecting the nodes with edges, each edge corresponding to a determined transition probability.

14. The non-transitory computer-readable storage medium of claim 8, wherein each node is associated with the emission probability.

15. A system comprising:
   one or more computer processors; and
   memory storing executable computer program instructions, the computer program instructions, when executed by the one or more computer processors, cause the one or more computer processors to perform steps comprising:

accessing a genotype dataset associated with an individual;

dividing the genotype dataset into a plurality of windows, each window comprising a set of a plurality of single nucleotide polymorphisms (SNPs);

determining a pair of phased haplotype datasets from the plurality of windows of genotype dataset;

generating, using one or more processors and the pair of phased haplotype datasets, an inter-window hidden Markov model (HMM) that comprises:

(i) a plurality of node groups, each node group representing one of the windows that comprises a set of SNPs, each node group comprising a plurality of nodes, each node representing a state of the window represented by the node group, the state comprising:

(1) a first parent label, and (2) a second parent label, and (ii) a plurality of edges, at least one edge connecting a first node to a second node and representing a transition from the first node to the second node, and wherein the inter-window HMM is trained by:

receiving phased haplotype datasets corresponding to sequences of alleles of individuals;

building per-window models for the plurality of windows;

receiving a set of reference panel samples; and training the per-window models using the set of reference panel samples to generate an emission probability for each node of each window in the inter-window HMI; and generating information on the individual using the inter-window HMM; and a graphical interface configured to display the information.

16. The system of claim 15, wherein the information on the individual comprises one or more of: a set of possible ethnic origins of the individual and percentage compositions of the set of the possible ethnic origins, a set of possible paternal origins and percentage compositions of the set of possible paternal origins, or a set of possible maternal origins and percentage compositions of the set of possible maternal origins.

17. The system of claim 15, wherein the information on the individual comprises one or more of: a visualization of the individual's ancestry composition by chromosome painting, information about a particular trait of the individual, a percentage of DNA shared with a relative of the individual, a set of similarities and differences in a first genotype dataset of a first parent of the individual and a second genotype dataset of a second parent of the individual, or information on individuals genetically related to the individual.

18. The system of claim 15, wherein the plurality of nodes in each node group represents permutations of different first parent labels and second parent labels.

19. The system of claim 15, wherein a switching of order of the first parent label and the second parent label corresponds to a switching of the first and second parent labels from one node group to a next node group.

20. The system of claim 15, wherein generating the inter-window HMM further comprises:

initiating label probabilities, each label probability for a particular label representing a probability distribution of the particular label among other possible labels;

initiating label change probabilities, each label change probability representing a likelihood of a change of label from one window to another window;

initiating a label switch probability representing a likelihood of a switching of order of the first parent label and the second parent label from one window to another window;

adjusting the label probabilities, label change probabilities, and the label switch probability through iterations;

determining transition probabilities based on the label probabilities, the label change probabilities, and the label switch probability, each transition probability associated with a particular edge and representing a likelihood of the first node connected by the particular edge from one node group transitioning to the second node connected by the particular edge from another node group; and connecting the nodes with edges, each edge corresponding to a determined transition probability.

* * * * *